US010577607B2

(12) United States Patent
Monia et al.

(10) Patent No.: US 10,577,607 B2
(45) Date of Patent: Mar. 3, 2020

(54) MODULATION OF DYRK1B EXPRESSION

(71) Applicant: Ionis Pharmaceuticals, Inc., Carlsbad, CA (US)

(72) Inventors: Brett P. Monia, Encinitas, CA (US); Shuling Guo, Carlsbad, CA (US); Susan F. Murray, Poway, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 16/085,140

(22) PCT Filed: Mar. 16, 2017

(86) PCT No.: PCT/US2017/022782
§ 371 (c)(1),
(2) Date: Sep. 14, 2018

(87) PCT Pub. No.: WO2017/161168
PCT Pub. Date: Sep. 21, 2017

(65) Prior Publication Data
US 2019/0071678 A1  Mar. 7, 2019

Related U.S. Application Data

(60) Provisional application No. 62/309,192, filed on Mar. 16, 2016.

(51) Int. Cl.
| | | |
|---|---|---|
| *C12N 15/113* | (2010.01) | |
| *A61K 31/7125* | (2006.01) | |
| *A61P 3/04* | (2006.01) | |
| *A61K 31/712* | (2006.01) | |
| *A61K 31/7115* | (2006.01) | |
| *A61K 9/00* | (2006.01) | |
| *A61K 31/7088* | (2006.01) | |
| *A61K 31/713* | (2006.01) | |
| *A61K 45/06* | (2006.01) | |

(52) U.S. Cl.
CPC ........ *C12N 15/1137* (2013.01); *A61K 9/0019* (2013.01); *A61K 9/0029* (2013.01); *A61K 31/7088* (2013.01); *A61K 31/712* (2013.01); *A61K 31/713* (2013.01); *A61K 31/7115* (2013.01); *A61K 31/7125* (2013.01); *A61K 45/06* (2013.01); *A61P 3/04* (2018.01); *C12N 2310/11* (2013.01); *C12N 2310/315* (2013.01); *C12N 2310/321* (2013.01); *C12N 2310/3341* (2013.01); *C12N 2310/341* (2013.01); *C12N 2310/346* (2013.01); *C12N 2320/31* (2013.01); *C12Y 207/01* (2013.01)

(58) Field of Classification Search
None
See application file for complete search history.

(56) References Cited

U.S. PATENT DOCUMENTS

| | | |
|---|---|---|
| 3,687,808 A | 8/1972 | Merigan et al. |
| 4,415,732 A | 11/1983 | Caruthers et al. |
| 4,458,066 A | 7/1984 | Caruthers et al. |
| 4,469,863 A | 9/1984 | Ts'o et al. |
| 4,476,301 A | 10/1984 | Imbach et al. |
| 4,500,707 A | 2/1985 | Caruthers et al. |
| 4,668,777 A | 5/1987 | Caruthers et al. |
| 4,725,677 A | 2/1988 | Koster et al. |
| 4,845,205 A | 7/1989 | Huynh Dinh et al. |
| 4,973,679 A | 11/1990 | Caruthers et al. |
| 4,981,957 A | 1/1991 | Lebleu et al. |
| 5,013,830 A | 5/1991 | Ohutsuka et al. |
| 5,023,243 A | 6/1991 | Tullis |
| 5,034,506 A | 7/1991 | Summerton et al. |
| 5,118,800 A | 6/1992 | Smith et al. |
| 5,130,302 A | 7/1992 | Spielvogel et al. |
| 5,132,418 A | 7/1992 | Caruthers et al. |
| 5,134,066 A | 7/1992 | Rogers et al. |
| RE34,036 E | 8/1992 | McGeehan |
| 5,149,797 A | 9/1992 | Pederson et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,177,198 A | 1/1993 | Spielvogel et al. |
| 5,188,897 A | 2/1993 | Suhadolnik et al. |
| 5,194,599 A | 3/1993 | Froehler et al. |
| 5,214,134 A | 5/1993 | Weis et al. |
| 5,216,141 A | 6/1993 | Benner |
| 5,220,007 A | 6/1993 | Pederson et al. |
| 5,223,618 A | 6/1993 | Cook et al. |
| 5,235,033 A | 8/1993 | Summerton et al. |
| 5,256,775 A | 10/1993 | Froehler |
| 5,264,423 A | 11/1993 | Cohen et al. |
| 5,264,562 A | 11/1993 | Matteucci |
| 5,264,564 A | 11/1993 | Matteucci |

(Continued)

FOREIGN PATENT DOCUMENTS

WO   WO 2015/196068   12/2015

OTHER PUBLICATIONS

Bennett et al Biochimica Aacta vol. 1489:19-30, 1999.*

(Continued)

*Primary Examiner* — Sean McGarry
(74) *Attorney, Agent, or Firm* — Grant IP

(57) ABSTRACT

Provided herein are methods, compounds, and compositions for reducing expression of DYRKIB in an animal. Such methods, compounds, and compositions are useful to treat, prevent, delay, or ameliorate a metabolic disease or disorder in an individual in need.

13 Claims, No Drawings

Specification includes a Sequence Listing.

(56) References Cited

U.S. PATENT DOCUMENTS

| | | |
|---|---|---|
| 5,185,444 A | 12/1993 | Summerton et al. |
| 5,276,019 A | 1/1994 | Cohen et al. |
| 5,278,302 A | 1/1994 | Caruthers et al. |
| 5,286,717 A | 2/1994 | Cohen et al. |
| 5,319,080 A | 6/1994 | Leumann |
| 5,321,131 A | 6/1994 | Agrawal et al. |
| 5,359,044 A | 10/1994 | Cook et al. |
| 5,366,878 A | 11/1994 | Pederson et al. |
| 5,367,066 A | 11/1994 | Urdea et al. |
| 5,378,825 A | 1/1995 | Cook et al. |
| 5,386,023 A | 1/1995 | Sanghvi et al. |
| 5,393,878 A | 2/1995 | Leumann |
| 5,399,676 A | 3/1995 | Froehler |
| 5,403,711 A | 4/1995 | Walder et al. |
| 5,405,938 A | 4/1995 | Sumerton et al. |
| 5,405,939 A | 4/1995 | Suhadolnik et al. |
| 5,432,272 A | 7/1995 | Benner |
| 5,434,257 A | 7/1995 | Matteucci |
| 5,446,137 A | 8/1995 | Maag et al. |
| 5,453,496 A | 9/1995 | Caruthers et al. |
| 5,455,233 A | 10/1995 | Spielvogel et al. |
| 5,457,187 A | 10/1995 | Gmelner et al. |
| 5,457,191 A | 10/1995 | Cook et al. |
| 5,459,255 A | 10/1995 | Cook et al. |
| 5,466,677 A | 11/1995 | Baxter et al. |
| 5,466,786 A | 11/1995 | Burh et al. |
| 5,470,967 A | 11/1995 | Huie et al. |
| 5,476,925 A | 12/1995 | Letsinger et al. |
| 5,484,908 A | 1/1996 | Froehler et al. |
| 5,489,677 A | 2/1996 | Sanghvi et al. |
| 5,491,133 A | 2/1996 | Walder et al. |
| 5,502,177 A | 3/1996 | Matteucci et al. |
| 5,508,270 A | 4/1996 | Baxter et al. |
| 5,514,785 A | 5/1996 | Van Ness et al. |
| 5,519,126 A | 5/1996 | Hecht |
| 5,519,134 A | 5/1996 | Acevedo et al. |
| 5,525,711 A | 6/1996 | Hawkins et al. |
| 5,527,899 A | 6/1996 | Froehler |
| 5,536,821 A | 7/1996 | Agrawal et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,552,540 A | 9/1996 | Haralambidis |
| 5,561,225 A | 10/1996 | Maddry et al. |
| 5,563,253 A | 10/1996 | Agrawal et al. |
| 5,565,350 A | 10/1996 | Kmiec |
| 5,565,555 A | 10/1996 | Froehler et al. |
| 5,567,811 A | 10/1996 | Mistura et al. |
| 5,571,799 A | 11/1996 | Tkachuk et al. |
| 5,576,427 A | 11/1996 | Cook et al. |
| 5,587,361 A | 12/1996 | Cook et al. |
| 5,587,469 A | 12/1996 | Cook et al. |
| 5,587,470 A | 12/1996 | Cook et al. |
| 5,591,722 A | 1/1997 | Montgomery et al. |
| 5,594,121 A | 1/1997 | Froehler et al. |
| 5,596,086 A | 1/1997 | Matteucci |
| 5,596,091 A | 1/1997 | Switzer |
| 5,597,909 A | 1/1997 | Urdea et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bishofberger et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci |
| 5,652,355 A | 7/1997 | Metelev et al. |
| 5,652,356 A | 7/1997 | Agrawal |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,681,941 A | 10/1997 | Cook et al. |
| 5,698,685 A | 12/1997 | Summerton et al. |
| 5,700,920 A | 12/1997 | Altmann et al. |
| 5,700,922 A | 12/1997 | Cook |
| 5,721,218 A | 2/1998 | Froehler |
| 5,750,692 A | 5/1998 | Cook et al. |
| 5,763,588 A | 6/1998 | Matteucci et al. |
| 5,792,608 A | 8/1998 | Swaminathan et al. |
| 5,792,847 A | 8/1998 | Burh et al. |
| 5,801,154 A | 9/1998 | Baracchini et al. |
| 5,808,027 A | 9/1998 | Cook et al. |
| 5,830,653 A | 11/1998 | Froehler et al. |
| 5,859,221 A | 1/1999 | Cook et al. |
| 5,948,903 A | 9/1999 | Cook et al. |
| 5,994,517 A | 11/1999 | Ts'O |
| 6,005,087 A | 12/1999 | Cook et al. |
| 6,005,096 A | 12/1999 | Matteucci et al. |
| 6,166,199 A | 12/2000 | Cook et al. |
| 6,268,490 B1 | 7/2001 | Imanishi et al. |
| 6,300,319 B1 | 10/2001 | Manoharan |
| 6,426,220 B1 | 7/2002 | Bennett et al. |
| 6,525,191 B1 | 2/2003 | Ramasamy |
| 6,531,584 B1 | 3/2003 | Cook et al. |
| 6,582,908 B2 | 6/2003 | Fodor et al. |
| 6,600,032 B1 | 7/2003 | Manoharan et al. |
| 6,660,720 B2 | 12/2003 | Manoharan |
| 6,670,461 B1 | 12/2003 | Wengel et al. |
| 6,770,748 B2 | 8/2004 | Imanishi et al. |
| 6,794,499 B2 | 9/2004 | Wengel et al. |
| 6,906,182 B2 | 6/2005 | Ts'o et al. |
| 7,015,315 B1 | 3/2006 | Cook et al. |
| 7,034,133 B2 | 4/2006 | Wengel et al. |
| 7,053,207 B2 | 5/2006 | Wengel et al. |
| 7,101,993 B1 | 9/2006 | Cook et al. |
| 7,262,177 B2 | 8/2007 | Ts'o et al. |
| 7,399,845 B2 | 7/2008 | Seth et al. |
| 7,427,672 B2 | 9/2008 | Imanishi et al. |
| 7,491,805 B2 | 2/2009 | Vargeese et al. |
| 7,547,684 B2 | 6/2009 | Seth et al. |
| 7,569,686 B1 | 8/2009 | Bhat et al. |
| 7,572,582 B2 | 8/2009 | Wengel et al. |
| 7,666,854 B2 | 2/2010 | Seth et al. |
| 7,696,345 B2 | 4/2010 | Allerson et al. |
| 7,723,509 B2 | 5/2010 | Manoharan et al. |
| 7,741,457 B2 | 6/2010 | Swayze et al. |
| 7,750,131 B2 | 7/2010 | Seth et al. |
| 7,875,733 B2 | 1/2011 | Bhat et al. |
| 7,939,677 B2 | 5/2011 | Bhat et al. |
| 8,022,193 B2 | 9/2011 | Swayze et al. |
| 8,030,467 B2 | 10/2011 | Seth et al. |
| 8,034,909 B2 | 10/2011 | Wengel et al. |
| 8,080,644 B2 | 12/2011 | Wengel et al. |
| 8,088,746 B2 | 1/2012 | Seth et al. |
| 8,088,904 B2 | 1/2012 | Swayze et al. |
| 8,106,022 B2 | 1/2012 | Manoharan et al. |
| 8,124,745 B2 | 2/2012 | Allerson et al. |
| 8,153,365 B2 | 4/2012 | Wengel et al. |
| 8,268,980 B2 | 9/2012 | Seth et al. |
| 8,278,283 B2 | 10/2012 | Seth et al. |
| 8,278,425 B2 | 10/2012 | Prakash et al. |
| 8,278,426 B2 | 10/2012 | Seth et al. |
| 8,440,803 B2 | 5/2013 | Swayze et al. |
| 8,501,805 B2 | 8/2013 | Seth et al. |
| 8,530,640 B2 | 9/2013 | Seth et al. |
| 8,546,556 B2 | 10/2013 | Seth et al. |
| RE44,779 E | 2/2014 | Imanishi et al. |
| 8,828,956 B2 | 9/2014 | Manoharan et al. |
| 9,005,906 B2 | 4/2015 | Swayze et al. |
| 9,012,421 B2 | 4/2015 | Migawa et al. |
| 9,127,276 B2 | 8/2015 | Prakash et al. |
| 9,290,760 B2 | 3/2016 | Rajeev et al. |
| 2001/0053519 A1 | 12/2001 | Fodor et al. |
| 2003/0082807 A1 | 5/2003 | Wengel |
| 2003/0158403 A1 | 8/2003 | Manoharan et al. |

(56) References Cited

U.S. PATENT DOCUMENTS

| | | |
|---|---|---|
| 2003/0175906 A1 | 9/2003 | Manoharan et al. |
| 2003/0207841 A1 | 11/2003 | Kaneko et al. |
| 2003/0224377 A1 | 12/2003 | Wengel et al. |
| 2003/0228597 A1 | 12/2003 | Cowsert et al. |
| 2004/0143114 A1 | 7/2004 | Imanishi et al. |
| 2004/0171570 A1 | 9/2004 | Allerson et al. |
| 2004/0192918 A1 | 9/2004 | Imanishi et al. |
| 2005/0130923 A1 | 6/2005 | Bhat et al. |
| 2006/0148740 A1 | 7/2006 | Platenburg |
| 2007/0031844 A1 | 2/2007 | Khvorova et al. |
| 2008/0039618 A1 | 2/2008 | Allerson et al. |
| 2010/0190837 A1 | 7/2010 | Migawa et al. |
| 2010/0197762 A1 | 8/2010 | Swayze et al. |
| 2011/0123520 A1 | 5/2011 | Manoharan et al. |
| 2013/0130378 A1 | 5/2013 | Manoharan et al. |
| 2013/0203836 A1 | 8/2013 | Rajeev et al. |
| 2014/0107330 A1 | 4/2014 | Freier et al. |
| 2014/0371251 A1 | 12/2014 | Aberger et al. |
| 2015/0018540 A1 | 1/2015 | Prakash et al. |
| 2015/0184153 A1 | 7/2015 | Freier et al. |
| 2015/0191727 A1 | 7/2015 | Migawa et al. |
| 2015/0246913 A1 | 9/2015 | Gray et al. |
| 2015/0267195 A1 | 9/2015 | Seth et al. |
| 2015/0275212 A1 | 10/2015 | Albaek et al. |

OTHER PUBLICATIONS

Ashford et al., "A Novel DYRK1B Inhibitor AZ191 Demonstrates that DYRK1B Acts Independently of GSK3β to Phosphorylate Cyclin D1 at Thr286, not Thr288" Biochem J (2014) 457: 43-56.

Branch et al., "A good antisense molecule is hard to find," TIBS (1998) 23:45-50.

Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.

Cho et al., "A genome-wide association study of COPD identifies a susceptibility locus on chromosome 19q13" Hum Mol Genet (2012) 21(4): 947-957.

Crooke et al., "Basic Principles of Antisense Therapeutics" Antisense Research and Application (1998) Chapter 1:1-50.

Crooke, ST., et al., "Antisense Drug Technology" Second Edition, CRC Press (2008) Chapters 1-28.

Egli, et al., "Synthesis, improved antisense activity and structural rationale for the divergent RNA affinities of 3'-fluoro hexitol nucleic acid (FHNA and Ara-FHNA) modified oligonucleotides." J Am Chem (2011) 133(41):16642-16649.

Gautschi et al., "Activity of a novel bcl-2/bcl-xLbispecific antisense oligonucleotide against tumors of diverse histologic origins" J. Natl. Cancer Inst. (2001) 93:463-471.

Keramati et al., "A Form of the Metabolic Syndrome Associated with Mutations in DYRK1B" The New England Journal of Medicine (2014) 370(20): 1909-1919.

Maher et al., "Comparative hybrid arrest by tandem antisense oligodeoxyribonucleotides or oligodeoxyribonucleoside methylpbosphonates in a cell-free system" Nucl. Acid. Res. (1988) 16(8):3341-3358.

New England Biolabs 1998/99 Catalog (cover page and pp. 121 and 284).

Reynolds et al., "Rational siRNA design for RNA interference" Nature Biotechnology (2004) 22(3):326-330.

Sanghvi et al., "Heterocyclic Base Modifications in Nucleic Acids and Their Applications in Antisense Oligonucleotides" Antisense Research and Applications (1993) pp. 273-288.

Seth et al., "Short Antisense Oligonucleotides with Novel 2'-4' Conformationally Restricted Nucleoside Analogues Show Improved Potency Without Increased Toxicity in Animals " J Med Chem (2009) 52:10-13.

Sim et al., "Transferability of type 2 diabetes implicated loci in multi-ethnic cohorts from Southeast Asia" PLoS Genet (2011) 7(4): e1001363.

Woolf et al., "Specificity of antisense oligonucleotides in vivo" PNAS (1992) 89: 7305-7309.

* cited by examiner

MODULATION OF DYRK1B EXPRESSION

SEQUENCE LISTING

The present application is being filed along with a Sequence Listing in electronic format. The Sequence Listing is provided as a file entitled BIOL0292USASEQ_ST25.txt, created on Sep. 13, 2018 which is 68 MB in size. The information in the electronic format of the sequence listing is incorporated herein by reference in its entirety.

FIELD OF THE INVENTION

Provided herein are methods, compounds, and compositions useful for reducing expression of dual-specificity tyrosine-(Y)-phosphorylation regulated kinase 1B (hereinafter referred to as DYRK1B) in an animal. Also, provided herein are methods, compounds, and compositions comprising DYRK1B inhibitors, which can be useful in reducing DYRK1B-related diseases or conditions in an animal. Such methods, compounds, and compositions can be useful, for example, to treat, prevent, delay or ameliorate metabolic disease in an animal.

BACKGROUND

The metabolic abnormalities such as high glucose, blood lipids, blood pressure and obesity have caused severe health threats. Recently, a genetic analysis study has identified the dual specificity tyrosine phosphorylation regulated kinase 1B (DYRK1B) as a causative mutation for metabolic diseases. DYRK1B is a dual-specificity kinases that possesses both serine/threonine and tyrosin kinase activities. The substituting cysteine for arginine at position 102 (R102C) mutation in DYRK1B showed gain-of-function activities and association with metabolic disease (Keramati et al, New Engl. J. Med. 370: 1909-1919, 2014). In another finding, L28P variant in DYRK1B, assumed loss-of-function mutation, showed significant protective effects against type 2 diabetes as well as hypertension. GWAS studies of the DYRK1B locus has been linked to Type 2 diabetes (Sim et al., PLoS Genet. 7: e1001363, 2011 and Cho et al., Hum. Mol. Genet. 21: 947-957, 2012).

SUMMARY

Provided herein are compositions, compounds and methods for modulating expression of DYRK1B associated with metabolic diseases or disorders. In certain embodiments, these compositions, compounds and methods are for modulating the expression of DYRK1B. In certain embodiments, the DYRK1B modulator is a DYRK1B-specific inhibitor. In certain embodiments, the DYRK1B-specific inhibitor decreases expression of a DYRK1B. In certain embodiments, DYRK1B-specific inhibitors include nucleic acids, proteins and small molecules. In certain embodiments, the DYRK1B-specific inhibitor is a nucleic acid. In certain embodiments, the nucleic acid is a compound. In certain embodiments, the compound comprises a modified oligonucleotide. In certain embodiments, the modified oligonucleotide can be single stranded or double stranded.

Certain embodiments are directed to DYRK1B inhibitors useful for inhibiting a DYRK1B, which can be useful for treating, ameliorating, or slowing progression of a metabolic disease or disorder. Certain embodiments relate to the novel findings of antisense inhibition of DYRK1B resulting in several metabolic endpoint lowering. Certain embodiments are directed to DYRK1B inhibitors useful in improving glucose tolerance. Certain embodiments are directed to DYRK1B inhibitors useful in reducing hyperglycemia. Certain embodiments are directed to DYRK1B inhibitors useful in improving insulin sensitivity. Certain embodiments are directed to DYRK1B inhibitors useful in improving glucose homeostasis. Certain embodiments are directed to DYRK1B inhibitors useful in reducing hypertension. In certain embodiments, the DYRK1B inhibitor is specific to DYRK1B and does not inhibit DYRK1A expression. In certain embodiments, it is desirable to inhibit DYRK1B expression without inhibiting DYRK1A expression.

DETAILED DESCRIPTION OF THE INVENTION

It is to be understood that both the foregoing general description and the following detailed description are exemplary and explanatory only and are not restrictive of the embodiments, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting.

The section headings used herein are for organizational purposes only and are not to be construed as limiting the subject matter described. All documents, or portions of documents, cited in this application, including, but not limited to, patents, patent applications, articles, books, treatises, and GenBank and NCBI reference sequence records are hereby expressly incorporated by reference for the portions of the document discussed herein, as well as in their entirety.

It is understood that the sequence set forth in each SEQ ID NO in the examples contained herein is independent of any modification to a sugar moiety, an internucleoside linkage, or a nucleobase. As such, compounds defined by a SEQ ID NO may comprise, independently, one or more modifications to a sugar moiety, an internucleoside linkage, or a nucleobase. Compounds described by ISIS number (ISIS #) indicate a combination of nucleobase sequence, chemical modification, and motif.

Unless otherwise indicated, the following terms have the following meanings:

"2'-deoxynucleoside" means a nucleoside comprising 2'-H(H) furanosyl sugar moiety, as found in naturally occurring deoxyribonucleic acids (DNA). In certain embodiments, a 2'-deoxynucleoside may comprise a modified nucleobase or may comprise an RNA nucleobase (uracil).

"2'-O-methoxyethyl" (also 2'-MOE and 2'-O(CH$_2$)$_2$—OCH$_3$) refers to an O-methoxy-ethyl modification at the 2' position of a furanosyl ring. A 2'-O-methoxyethyl modified sugar is a modified sugar.

"2'-MOE nucleoside" (also 2'-O-methoxyethyl nucleoside) means a nucleoside comprising a 2'-MOE modified sugar moiety.

"2'-substituted nucleoside" or "2-modified nucleoside" means a nucleoside comprising a 2'-substituted or 2'-modified sugar moiety. As used herein, "2'-substituted" or "2-modified" in reference to a sugar moiety means a sugar moiety comprising at least one 2'-substituent group other than H or OH.

"3' target site" refers to the nucleotide of a target nucleic acid which is complementary to the 3'-most nucleotide of a particular compound.

"5' target site" refers to the nucleotide of a target nucleic acid which is complementary to the 5'-most nucleotide of a particular compound.

"5-methylcytosine" means a cytosine with a methyl group attached to the 5 position.

"About" means within ±10% of a value. For example, if it is stated, "the compounds affected about 70% inhibition of a DYRK1B", it is implied that DYRK1B levels are inhibited within a range of 60% and 80%.

"Administration" or "administering" refers to routes of introducing a compound or composition provided herein to an individual to perform its intended function. An example of a route of administration that can be used includes, but is not limited to parenteral administration, such as subcutaneous, intravenous, or intramuscular injection or infusion.

"Administered concomitantly" or "co-administration" means administration of two or more compounds in any manner in which the pharmacological effects of both are manifest in the patient. Concomitant administration does not require that both compounds be administered in a single pharmaceutical composition, in the same dosage form, by the same route of administration, or at the same time. The effects of both compounds need not manifest themselves at the same time. The effects need only be overlapping for a period of time and need not be coextensive. Concomitant administration or co-administration encompasses administration in parallel or sequentially.

"Amelioration" refers to an improvement or lessening of at least one indicator, sign, or symptom of an associated disease, disorder, or condition. In certain embodiments, amelioration includes a delay or slowing in the progression or severity of one or more indicators of a condition or disease. The progression or severity of indicators may be determined by subjective or objective measures, which are known to those skilled in the art.

"Animal" refers to a human or non-human animal, including, but not limited to, mice, rats, rabbits, dogs, cats, pigs, and non-human primates, including, but not limited to, monkeys and chimpanzees.

"Antisense activity" means any detectable and/or measurable activity attributable to the hybridization of an antisense compound to its target nucleic acid. In certain embodiments, antisense activity is a decrease in the amount or expression of a target nucleic acid or protein encoded by such target nucleic acid compared to target nucleic acid levels or target protein levels in the absence of the antisense compound to the target.

"Antisense compound" means a compound comprising an oligonucleotide and optionally one or more additional features, such as a conjugate group or terminal group. Examples of antisense compounds include single-stranded and double-stranded compounds, such as, oligonucleotides, ribozymes, siRNAs, shRNAs, ssRNAs, and occupancy-based compounds.

"Antisense inhibition" means reduction of target nucleic acid levels in the presence of an antisense compound complementary to a target nucleic acid compared to target nucleic acid levels in the absence of the antisense compound.

"Antisense mechanisms" are all those mechanisms involving hybridization of a compound with target nucleic acid, wherein the outcome or effect of the hybridization is either target degradation or target occupancy with concomitant stalling of the cellular machinery involving, for example, transcription or splicing.

"Antisense oligonucleotide" means an oligonucleotide having a nucleobase sequence that is complementary to a target nucleic acid or region or segment thereof. In certain embodiments, an antisense oligonucleotide is specifically hybridizable to a target nucleic acid or region or segment thereof.

"Bicyclic nucleoside" or "BNA" means a nucleoside comprising a bicyclic sugar moiety. "Bicyclic sugar" or "bicyclic sugar moiety" means a modified sugar moiety comprising two rings, wherein the second ring is formed via a bridge connecting two of the atoms in the first ring thereby forming a bicyclic structure. In certain embodiments, the first ring of the bicyclic sugar moiety is a furanosyl moiety. In certain embodiments, the bicyclic sugar moiety does not comprise a furanosyl moiety.

"Branching group" means a group of atoms having at least 3 positions that are capable of forming covalent linkages to at least 3 groups. In certain embodiments, a branching group provides a plurality of reactive sites for connecting tethered ligands to an oligonucleotide via a conjugate linker and/or a cleavable moiety.

"Cardiovascular disease" or "cardiovascular disorder" refers to a group of conditions related to the heart, blood vessels, or the circulation.

"Chemical modification" in a compound describes the substitutions or changes through chemical reaction, of any of the units in the compound. "Modified nucleoside" means a nucleoside having, independently, a modified sugar moiety and/or modified nucleobase. "Modified oligonucleotide" means an oligonucleotide comprising at least one modified internucleoside linkage, a modified sugar, and/or a modified nucleobase.

"Chemically distinct region" refers to a region of a compound that is in some way chemically different than another region of the same compound. For example, a region having 2'-O-methoxyethyl nucleotides is chemically distinct from a region having nucleotides without 2'-O-methoxyethyl modifications.

"Chimeric antisense compounds" means antisense compounds that have at least 2 chemically distinct regions, each position having a plurality of subunits.

"Cholesterol" is a sterol molecule found in the cell membranes of all animal tissues. Cholesterol may be transported in an animal's blood plasma by lipoproteins including very low density lipoprotein (VLDL), intermediate density lipoprotein (IDL), low density lipoprotein (LDL), and high density lipoprotein (HDL). "Plasma cholesterol" refers to cholesterol present in the plasma.

"Cleavable bond" means any chemical bond capable of being split. In certain embodiments, a cleavable bond is selected from among: an amide, a polyamide, an ester, an ether, one or both esters of a phosphodiester, a phosphate ester, a carbamate, a di-sulfide, or a peptide.

"Cleavable moiety" means a bond or group of atoms that is cleaved under physiological conditions, for example, inside a cell, an animal, or a human.

"Complementary" in reference to an oligonucleotide means the nucleobase sequence of such oligonucleotide or one or more regions thereof matches the nucleobase sequence of another oligonucleotide or nucleic acid or one or more regions thereof when the two nucleobase sequences are aligned in opposing directions. Nucleobase matches or complementary nucleobases, as described herein, are limited to the following pairs: adenine (A) and thymine (T), adenine (A) and uracil (U), cytosine (C) and guanine (G), and 5-methyl cytosine ($^m$C) and guanine (G) unless otherwise specified. Complementary oligonucleotides and/or nucleic acids need not have nucleobase complementarity at each nucleoside and may include one or more nucleobase mismatches. By contrast, "fully complementary" or "100% complementary" in reference to oligonucleotides means that such oligonucleotides have nucleobase matches at each nucleoside without any nucleobase mismatches.

"Contiguous" in the context of an oligonucleotide refers to nucleosides, nucleobases, sugar moieties, or internucleoside linkages that are immediately adjacent to each other. For example, "contiguous nucleobases" means nucleobases that are immediately adjacent to each other in a sequence.

"Designing" or "Designed to" refer to the process of designing a compound that specifically hybridizes with a selected nucleic acid molecule.

"Diabetes mellitus" or "diabetes" is a syndrome characterized by disordered metabolism and abnormally high blood sugar (hyperglycemia) resulting from insufficient levels of insulin or reduced insulin sensitivity. The characteristic symptoms are excessive urine production (polyuria) due to high blood glucose levels, excessive thirst and increased fluid intake (polydipsia) attempting to compensate for increased urination, blurred vision due to high blood glucose effects on the eye's optics, unexplained weight loss, and lethargy.

"Diabetic dyslipidemia" or "type II diabetes with dyslipidemia" means a condition characterized by Type II diabetes, reduced HDL-C, elevated triglycerides, and elevated small, dense LDL particles.

"Diluent" means an ingredient in a composition that lacks pharmacological activity, but is pharmaceutically necessary or desirable. For example, the diluent in an injected composition can be a liquid, e.g. saline solution.

"Differently modified" mean chemical modifications or chemical substituents that are different from one another, including absence of modifications. Thus, for example, a MOE nucleoside and an unmodified DNA nucleoside are "differently modified," even though the DNA nucleoside is unmodified. Likewise, DNA and RNA are "differently modified," even though both are naturally-occurring unmodified nucleosides. Nucleosides that are the same but for comprising different nucleobases are not differently modified. For example, a nucleoside comprising a 2'-OMe modified sugar and an unmodified adenine nucleobase and a nucleoside comprising a 2'-OMe modified sugar and an unmodified thymine nucleobase are not differently modified.

"Dose" means a specified quantity of a compound or pharmaceutical agent provided in a single administration, or in a specified time period. In certain embodiments, a dose may be administered in two or more boluses, tablets, or injections. For example, in certain embodiments, where subcutaneous administration is desired, the desired dose may require a volume not easily accommodated by a single injection. In such embodiments, two or more injections may be used to achieve the desired dose. In certain embodiments, a dose may be administered in two or more injections to minimize injection site reaction in an individual. In other embodiments, the compound or pharmaceutical agent is administered by infusion over an extended period of time or continuously. Doses may be stated as the amount of pharmaceutical agent per hour, day, week or month.

"Dosing regimen" is a combination of doses designed to achieve one or more desired effects.

"Double-stranded compound" means a compound comprising two oligomeric compounds that are complementary to each other and form a duplex, and wherein one of the two said oligomeric compounds comprises an oligonucleotide.

"DYRK1B" means dual specificity tyrosine phosphorylation regulated kinase 1B and refers to any nucleic acid of DYRK1B. For example, in certain embodiments, DYRK1B includes a DNA sequence encoding the DYRK1B, an RNA sequence transcribed from DNA encoding the DYRK1B (including genomic DNA comprising introns and exons). The target may be referred to in either upper or lower case.

"DYRK1B-specific inhibitor" refers to any agent capable of specifically inhibiting DYRK1B expression or activity at the molecular level. For example, DYRK1B-specific inhibitors include nucleic acids (including antisense compounds), peptides, antibodies, small molecules, and other agents capable of inhibiting the expression of DYRK1B.

"Dyslipidemia" refers to a disorder of lipid and/or lipoprotein metabolism, including lipid and/or lipoprotein overproduction or deficiency. Dyslipidemias may be manifested by elevation of lipids such as cholesterol and triglycerides as well as lipoproteins such as low-density lipoprotein (LDL) cholesterol.

"Effective amount" means the amount of compound sufficient to effectuate a desired physiological outcome in an individual in need of the compound. The effective amount may vary among individuals depending on the health and physical condition of the individual to be treated, the taxonomic group of the individuals to be treated, the formulation of the composition, assessment of the individual's medical condition, and other relevant factors.

"Efficacy" means the ability to produce a desired effect.

"Elevated cholesterol" means cholesterol at a concentration in a subject at which lipid-lowering therapy is recommended, and includes, without limitation, elevated LDL-C", "elevated VLDL-C," "elevated IDL-C" and "elevated non-HDL-C." In certain embodiments, cholesterol concentrations of less than 200 mg/dL, 200-239 mg/dL, and greater than 240 mg/dL are considered desirable, borderline high, and high, respectively. In certain embodiments, LDL-C concentrations of 100 mg/dL, 100-129 mg/dL, 130-159 mg/dL, 160-189 mg/dL, and greater than 190 mg/dL are considered optimal, near optimal/above optimal, borderline high, high, and very high, respectively.

"Elevated triglyceride" means a concentration of triglyceride in the serum or liver at which lipid-lowering therapy is recommended, and includes "elevated triglyceride" and "elevated liver triglyceride." In certain embodiments, triglyceride concentration of 150-199 mg/dL, 200-499 mg/dL, and greater than or equal to 500 mg/dL is considered borderline high, high, and very high, respectively.

"Ensembl ID" is an identification number consisting of letters and numbers assigned to a gene sequence by Ensembl, which is a joint project between EMBL-EBI and the Wellcome Trust Sanger Institute to develop a software system that produces and maintans automatic annotation of selected eukaryotic genomes. Ensembl annotation helps identify a gene location in a particular genome and can be used to configure the equivalent gene on another species' genome.

"Expression" includes all the functions by which a gene's coded information is converted into structures present and operating in a cell. Such structures include, but are not limited to the products of transcription and translation.

"Gapmer" means an oligonucleotide comprising an internal region having a plurality of nucleosides that support RNase H cleavage positioned between external regions having one or more nucleosides, wherein the nucleosides comprising the internal region are chemically distinct from the nucleoside or nucleosides comprising the external regions. The internal region may be referred to as the "gap" and the external regions may be referred to as the "wings."

"Glucose" is a monosaccharide used by cells as a source of energy and metabolic intermediate. "Plasma glucose" refers to glucose present in the plasma or serum "Glucose tolerance test" in medical practice is defined as the administration of glucose to determine how quickly it is cleared from the blood. The test is usually used to test for diabetes, insulin resistance, and sometimes reactive hypoglycemia. The glucose is most often given orally so the common test is technically an oral glucose tolerance test (OGTT).

"Hybridization" means annealing of oligonucleotides and/or nucleic acids. While not limited to a particular mechanism, the most common mechanism of hybridization involves hydrogen bonding, which may be Watson-Crick, Hoogsteen or reversed Hoogsteen hydrogen bonding, between complementary nucleobases. In certain embodiments, complementary nucleic acid molecules include, but are not limited to, an antisense compound and a nucleic acid target. In certain embodiments, complementary nucleic acid molecules include, but are not limited to, an oligonucleotide and a nucleic acid target.

"Hyperglycemia" means a condition characterized by elevated serum glucose levels and/or circulating (plasma) glucose levels.

"Hyperlipidemia" means a condition characterized by elevated serum lipid levels and/or circulating (plasma) lipid levels.

"Hypertriglyceridemia" means a condition characterized by elevated triglyceride or circulating (plasma) triglyceride levels.

"Immediately adjacent" means there are no intervening elements between the immediately adjacent elements of the same kind (e.g. no intervening nucleobases between the immediately adjacent nucleobases).

"Individual" means a human or non-human animal selected for treatment or therapy.

"Inhibiting the expression or activity" refers to a reduction or blockade of the expression or activity relative to the expression of activity in an untreated or control sample and does not necessarily indicate a total elimination of expression or activity.

"Insulin resistance" is defined as the condition in which normal amounts of insulin are inadequate to produce a normal insulin response from fat, muscle and liver cells. Insulin resistance in fat cells results in hydrolysis of stored triglycerides, which elevates free fatty acids in the blood plasma. Insulin resistance in muscle reduces glucose uptake whereas insulin resistance in liver reduces glucose storage, with both effects serving to elevate blood glucose. High plasma levels of insulin and glucose due to insulin resistance often leads to metabolic syndrome and type 2 diabetes.

"Insulin sensitivity" is a measure of how effectively an individual processes glucose. An individual having high insulin sensitivity effectively processes glucose whereas an individual with low insulin sensitivity does not effectively process glucose.

"Internucleoside linkage" means a group or bond that forms a covalent linkage between adjacent nucleosides in an oligonucleotide. "Modified internucleoside linkage" means any internucleoside linkage other than a naturally occurring, phosphate internucleoside linkage. Non-phosphate linkages are referred to herein as modified internucleoside linkages.

"Intraperitoneal administration" means administration through infusion or injection into the peritoneum.

"Intravenous administration" means administration into a vein.

"IPGTT" or "Intraperitoneal Glucose Tolerance Testing" in medical practice is defined as the administration of glucose through intraperitoneal injection to determine how quickly it is cleared from the blood. The test is usually used to test for diabetes, insulin resistance, and sometimes reactive hypoglycemia.

"ITT" or "Insulin Tolerance Test" in medical practice is defined as a test to measure insulin sensitivity through the hormone response to the stress of a low blood sugar level. The test is usually used to test for diabetes, insulin resistance, and sometimes reactive hypoglycemia.

"Lengthened oligonucleotides" are those that have one or more additional nucleosides relative to an oligonucleotide disclosed herein, e.g. a parent oligonucleotide.

"Linked nucleosides" means adjacent nucleosides linked together by an internucleoside linkage.

"Metabolic disorder" refers to a condition characterized by an alteration or disturbance in metabolic function. Metabolic disorders include, but are not limited to, hyperglycemia, prediabetes, diabetes (type I and type II), obesity, insulin resistance and metabolic syndrome.

"Metabolic syndrome" is defined as a clustering of lipid and non-lipid cardiovascular risk factors of metabolic origin.

"Mismatch" or "non-complementary" means a nucleobase of a first oligonucleotide that is not complementary to the corresponding nucleobase of a second oligonucleotide or target nucleic acid when the first and second oligonucleotides are aligned. For example, nucleobases including but not limited to a universal nucleobase, inosine, and hypoxanthine, are capable of hybridizing with at least one nucleobase but are still mismatched or non-complementary with respect to nucleobase to which it hybridized. As another example, a nucleobase of a first oligonucleotide that is not capable of hybridizing to the corresponding nucleobase of a second oligonucleotide or target nucleic acid when the first and second oligonucleotides are aligned is a mismatch or non-complementary nucleobase.

"Modulating" refers to changing or adjusting a feature in a cell, tissue, organ or organism. For example, modulating a DYRK1B can mean to increase or decrease the level of the DYRK1B in a cell, tissue, organ or organism. A "modulator" effects the change in the cell, tissue, organ or organism. For example, a compound can be a modulator of DYRK1B that decreases the amount of DYRK1B in a cell, tissue, organ or organism.

"MOE" means methoxyethyl.

"Monomer" refers to a single unit of an oligomer. Monomers include, but are not limited to, nucleosides and nucleotides.

"Motif" means the pattern of unmodified and/or modified sugar moieties, nucleobases, and/or internucleoside linkages, in an oligonucleotide.

"Natural" or "naturally occurring" means found in nature.

"Non-bicyclic modified sugar" or "non-bicyclic modified sugar moiety" means a modified sugar moiety that comprises a modification, such as a substituent, that does not form a bridge between two atoms of the sugar to form a second ring.

"Nucleic acid" refers to molecules composed of monomeric nucleotides. A nucleic acid includes, but is not limited to, ribonucleic acids (RNA), deoxyribonucleic acids (DNA), single-stranded nucleic acids, and double-stranded nucleic acids.

"Nucleobase" means a heterocyclic moiety capable of pairing with a base of another nucleic acid. As used herein a "naturally occurring nucleobase" is adenine (A), thymine (T), cytosine (C), uracil (U), and guanine (G). A "modified nucleobase" is a naturally occurring nucleobase that is chemically modified. A "universal base" or "universal nucleobase" is a nucleobase other than a naturally occurring nucleobase and modified nucleobase, and is capable of pairing with any nucleobase.

"Nucleobase sequence" means the order of contiguous nucleobases in a nucleic acid or oligonucleotide independent of any sugar or internucleoside linkage.

"Nucleoside" means a compound comprising a nucleobase and a sugar moiety. The nucleobase and sugar moiety are each, independently, unmodified or modified. "Modified nucleoside" means a nucleoside comprising a modified nucleobase and/or a modified sugar moiety. Modified nucleosides include abasic nucleosides, which lack a nucleobase.

"Obesity" means an excessively high amount of body fat or adipose tissue in relation to lean body mass. The amount of body fat (or adiposity) includes concern for both the distribution of fat throughout the body and the size of the adipose tissue deposits. Body fat distribution can be estimated by skin-fold measures, waist-to-hip circumference ratios, or techniques such as ultrasound, computed tomography, or magnetic resonance imaging. According to the Center for Disease Control and Prevention, individuals with a body mass index (BMI) of 30 or more are considered obese.

"Oligomeric compound" means a compound comprising a single oligonucleotide and optionally one or more additional features, such as a conjugate group or terminal group.

"Oligonucleotide" means a polymer of linked nucleosides each of which can be modified or unmodified, independent one from another. Unless otherwise indicated, oligonucleotides consist of 8-80 linked nucleosides. "Modified oligonucleotide" means an oligonucleotide, wherein at least one sugar, nucleobase, or internucleoside linkage is modified. "Unmodified oligonucleotide" means an oligonucleotide that does not comprise any sugar, nucleobase, or internucleoside modification.

"Parent oligonucleotide" means an oligonucleotide whose sequence is used as the basis of design for more oligonucleotides of similar sequence but with different lengths, motifs, and/or chemistries. The newly designed oligonucleotides may have the same or overlapping sequence as the parent oligonucleotide.

"Parenteral administration" means administration through injection or infusion. Parenteral administration includes subcutaneous administration, intravenous administration, intramuscular administration, intraarterial administration, intraperitoneal administration, or intracranial administration, e.g. intrathecal or intracerebroventricular administration.

"Pharmaceutically acceptable carrier or diluent" means any substance suitable for use in administering to an animal. For example, a pharmaceutically acceptable carrier can be a sterile aqueous solution, such as PBS or water-for-injection.

"Pharmaceutically acceptable salts" means physiologically and pharmaceutically acceptable salts of compounds, such as oligomeric compounds or oligonucleotides, i.e., salts that retain the desired biological activity of the parent compound and do not impart undesired toxicological effects thereto.

"Pharmaceutical agent" means a compound that provides a therapeutic benefit when administered to an individual.

"Pharmaceutical composition" means a mixture of substances suitable for administering to an individual. For example, a pharmaceutical composition may comprise one or more compounds or salt thereof and a sterile aqueous solution.

"Phosphorothioate linkage" means a modified phosphate linkage in which one of the non-bridging oxygen atoms is replaced with a sulfur atom. A phosphorothioate internucleoside linkage is a modified internucleoside linkage.

"Phosphorus moiety" means a group of atoms comprising a phosphorus atom. In certain embodiments, a phosphorus moiety comprises a mono-, di-, or tri-phosphate, or phosphorothioate.

"Portion" means a defined number of contiguous (i.e., linked) nucleobases of a nucleic acid. In certain embodiments, a portion is a defined number of contiguous nucleobases of a target nucleic acid. In certain embodiments, a portion is a defined number of contiguous nucleobases of an oligomeric compound.

"Prevent" refers to delaying or forestalling the onset, development or progression of a disease, disorder, or condition for a period of time from minutes to indefinitely.

"Prodrug" means a compound in a form outside the body which, when administered to an individual, is metabolized to another form within the body or cells thereof. In certain embodiments, the metabolized form is the active, or more active, form of the compound (e.g., drug). Typically conversion of a prodrug within the body is facilitated by the action of an enzyme(s) (e.g., endogenous or viral enzyme) or chemical(s) present in cells or tissues, and/or by physiologic conditions.

"Reduce" means to bring down to a smaller extent, size, amount, or number.

"RefSeq No." is a unique combination of letters and numbers assigned to a sequence to indicate the sequence is for a particular target transcript (e.g., target gene). Such sequence and information about the target gene (collectively, the gene record) can be found in a genetic sequence database. Genetic sequence databases include the NCBI Reference Sequence database, GenBank, the European Nucleotide Archive, and the DNA Data Bank of Japan (the latter three forming the International Nucleotide Sequence Database Collaboration or INSDC).

"Region" is defined as a portion of the target nucleic acid having at least one identifiable structure, function, or characteristic.

"RNAi compound" means an antisense compound that acts, at least in part, through RISC or Ago2, but not through RNase H, to modulate a target nucleic acid and/or protein encoded by a target nucleic acid. RNAi compounds include, but are not limited to double-stranded siRNA, single-stranded RNA (ssRNA), and microRNA, including microRNA mimics.

"Segments" are defined as smaller or sub-portions of regions within a nucleic acid.

"Side effects" means physiological disease and/or conditions attributable to a treatment other than the desired effects. In certain embodiments, side effects include injection site reactions, liver function test abnormalities, renal function abnormalities, liver toxicity, renal toxicity, central nervous system abnormalities, myopathies, and malaise. For example, increased aminotransferase levels in serum may indicate liver toxicity or liver function abnormality. For example, increased bilirubin may indicate liver toxicity or liver function abnormality.

"Single-stranded" in reference to a compound means the compound has only one oligonucleotide. "Self-complementary" means an oligonucleotide that at least partially hybridizes to itself. A compound consisting of one oligonucleotide, wherein the oligonucleotide of the compound is self-complementary, is a single-stranded compound. A single-stranded compound may be capable of binding to a complementary compound to form a duplex.

"Sites," are defined as unique nucleobase positions within a target nucleic acid.

"Specifically hybridizable" refers to an oligonucleotide having a sufficient degree of complementarity between the oligonucleotide and a target nucleic acid to induce a desired effect, while exhibiting minimal or no effects on non-target nucleic acids. In certain embodiments, specific hybridization occurs under physiological conditions.

"Specifically inhibit" a target nucleic acid means to reduce or block expression of the target nucleic acid while exhibiting fewer, minimal, or no effects on non-target nucleic acids reduction and does not necessarily indicate a total elimination of the target nucleic acid's expression.

"Standard cell assay" means assay(s) described in the Examples and reasonable variations thereof "Standard in vivo experiment" means the procedure(s) described in the Example(s) and reasonable variations thereof.

"Sugar moiety" means an unmodified sugar moiety or a modified sugar moiety. "Unmodified sugar moiety" or "unmodified sugar" means a 2'-OH(H) furanosyl moiety, as found in RNA (an "unmodified RNA sugar moiety"), or a 2'-H(H) moiety, as found in DNA (an "unmodified DNA sugar moiety"). Unmodified sugar moieties have one hydrogen at each of the 1', 3', and 4' positions, an oxygen at the 3' position, and two hydrogens at the 5' position. "Modified sugar moiety" or "modified sugar" means a modified furanosyl sugar moiety or a sugar surrogate. "Modified furanosyl sugar moiety" means a furanosyl sugar comprising a non-hydrogen substituent in place of at least one hydrogen of an unmodified sugar moiety. In certain embodiments, a modified furanosyl sugar moiety is a 2'-substituted sugar moiety. Such modified furanosyl sugar moieties include bicyclic sugars and non-bicyclic sugars.

"Sugar surrogate" means a modified sugar moiety having other than a furanosyl moiety that can link a nucleobase to another group, such as an internucleoside linkage, conjugate group, or terminal group in an oligonucleotide. Modified nucleosides comprising sugar surrogates can be incorporated into one or more positions within an oligonucleotide and such oligonucleotides are capable of hybridizing to complementary oligomeric compounds or nucleic acids.

"Subcutaneous administration" means administration just below the skin.

"Target gene" refers to a gene encoding a target.

"Targeting" means specific hybridization of a compound that to a target nucleic acid in order to induce a desired effect.

"Target nucleic acid," "target RNA," "target RNA transcript" and "nucleic acid target" all mean a nucleic acid capable of being targeted by compounds described herein.

"Target region" means a portion of a target nucleic acid to which one or more compounds is targeted.

"Target segment" means the sequence of nucleotides of a target nucleic acid to which a compound described herein is targeted. "5' target site" refers to the 5'-most nucleotide of a target segment. "3' target site" refers to the 3'-most nucleotide of a target segment.

"Terminal group" means a chemical group or group of atoms that is covalently linked to a terminus of an oligonucleotide.

"Therapeutically effective amount" means an amount of a compound, pharmaceutical agent, or composition that provides a therapeutic benefit to an individual.

"Total cholesterol" means all types of cholesterol, including, but not limited to, LDL-C, HDL-C, IDL-C and VLDL-C. Concentration of total cholesterol in serum (or plasma) is typically quantified in mg/dL or nmol/L.

"Treat" refers to administering a compound or pharmaceutical composition to an animal in order to effect an alteration or improvement of a disease, disorder, or condition in the animal.

"Triglycerides" means lipids that are the triesters of glycerol.

"Type I diabetes" (also known as insulin-dependent diabetes mellitus or IDDM—strikes people under age 35, typically appearing suddenly between the ages of 10 and 16. In this form of the illness, which affects 10 percent of diabetics, a virus or autoimmune reaction probably destroys the insulin-producing cells. Insulin normally enables sugar to pass from the blood into the body's cells. Since a person with type I diabetes has completely stopped producing insulin, lifelong treatment means taking insulin several times daily.

"Type 2 diabetes," (also known as "type 2 diabetes mellitus" or "diabetes mellitus, type 2", and formerly called "diabetes mellitus type II", "non-insulin-dependent diabetes (NIDDM)", "obesity related diabetes", or "adult-onset diabetes") is a metabolic disorder that is primarily characterized by insulin resistance, relative insulin deficiency, and hyperglycemia.

"White Adipose Tissue" or WAT refers to one of the two types of adipose tissue found in mammals. In humans, white adipose tissue composes as much as 20% of the body weight in men and 25% of the body weight in women. The white adipose tissue is used as a store of energy and also acts as a thermal insulator, helping to maintain body temperature.

Certain Embodiments

Certain embodiments provide methods, compounds, and compositions for modulating a metabolic condition, or a symptom thereof, in an animal or individual by administering a therapeutically effective amount of the compound or composition to the animal or individual, wherein the compound or composition comprises a DYRK1B modulator. Modulation of DYRK1B can lead to a decrease of DYRK1B level or expression in order to treat, prevent, ameliorate or delay a metabolic disease or disorder, or a symptom thereof. In certain embodiments, the DYRK1B modulator is a DYRK1B-specific inhibitor. In certain embodiments, DYRK1B-specific inhibitors are nucleic acids (including antisense compounds), peptides, antibodies, small molecules, and other agents capable of inhibiting the expression of DYRK1B. In certain embodiments, DYRK-1B-specific inhibitors do not inhibit DYRK1A. In certain embodiments, the animal or individual is human.

Certain embodiments disclosed herein provide a method of treating, preventing, delaying or ameliorating a metabolic disease or disorder in an animal or individual comprising administering to the animal or individual a compound or composition comprising a DYRK1B-specific inhibitor. In certain embodiments, the DYRK1B-specific inhibitor is a nucleic acid, peptide, antibody, small molecule or other agent capable of inhibiting the expression of DYRK1B. In certain embodiments, the DYRK1B-specific inhibitor comprises a compound described herein. In certain embodiments, the compound comprises an antisense compound or an oligomeric compound. In certain embodiments, the compound comprises a modified oligonucleotide. In certain embodiments, the modified oligonucleotide consists of 10 to 30 linked nucleosides. In certain embodiments, the animal or individual is human. In certain embodiments, the metabolic disease or disorder is diabetes mellitus, hyperglycemia, obesity, metabolic syndrome, essential hypertension, disorders of lipid metabolism, hypertensive heart disease, myocardial infarction, pulmonary heart disease, heart failure, and other symptoms involving the cardiovascular system. In certain embodiments, the animal or individual is human.

Certain embodiments disclosed herein provide a method of treating an animal or individual at risk for a metabolic disease or disorder comprising administering to the animal or individual a compound or composition comprising a DYRK1B-specific inhibitor. In certain embodiments, the DYRK1B-specific inhibitor is a nucleic acid, peptide, antibody, small molecule or other agent capable of inhibiting the expression of DYRK1B. In certain embodiments, the DYRK1B-specific inhibitor comprises a compound. In certain embodiments, the compound comprises an antisense compound or an oligomeric compound. In certain embodiments, the compound comprises a modified oligonucleotide. In certain embodiments, the metabolic disease or disorder is diabetes mellitus, hyperglycemia, obesity, metabolic syndrome, essential hypertension, disorders of lipid metabolism, hypertensive heart disease, myocardial infarction, pulmonary heart disease, heart failure, and other symptoms involving the cardiovascular system. In certain embodiments, the animal or individual is human.

Certain embodiments disclosed herein provide compounds or compositions comprising a DYRK1B modulator. In certain embodiments, the DYRK1B modulator is a DYRK1B-specific inhibitor. In certain embodiments, the DYRK1B-specific inhibitor is a nucleic acid, polypeptide, antibody, small molecules, or other agent capable of inhibiting the expression of DYRK1B. In certain embodiments, the nucleic acid is a compound or composition targeting DYRK1B. In certain embodiments, the compound or composition is single stranded. In certain embodiments, the compound or composition is double stranded. In certain embodiments, the compound is an antisense compound. In any of the foregoing embodiments, the compound can be an oligomeric compound. In certain embodiments, the compound or composition targeting DYRK1B comprises an oligonucleotide. In certain embodiments, the oligonucleotide is single stranded. In certain embodiments, the compound comprises deoxyribonucleotides. In certain embodiments, the compound is double-stranded and comprises ribonucleotides. In certain embodiments, the oligonucleotide is a modified oligonucleotide. In certain embodiments, the modified oligonucleotide is single stranded.

In any of the foregoing embodiments, the compound can comprise a modified oligonucleotide consisting of 8 to 80, 10 to 30, 12 to 50, 13 to 30, 13 to 50, 14 to 30, 14 to 50, 15 to 30, 15 to 50, 16 to 30, 16 to 50, 17 to 30, 17 to 50, 18 to 22, 18 to 24, 18 to 30, 18 to 50, 19 to 22, 19 to 30, 19 to 50, or 20 to 30 linked nucleosides. In certain embodiments, these compounds are oligonucleotides.

In certain embodiments, at least one internucleoside linkage of said modified oligonucleotide is a modified internucleoside linkage. In certain embodiments, at least one internucleoside linkage is a phosphorothioate internucleoside linkage. In certain embodiments, the internucleoside linkages are phosphorothioate linkages and phosphodiester linkages. In certain embodiments, each internucleoside linkage is a phosphorothioate internucleoside linkage.

In certain embodiments, any of the foregoing oligonucleotides comprises at least one modified sugar. In certain embodiments, at least one modified sugar comprises a 2'-O-methoxyethyl group. In certain embodiments, at least one modified sugar is a bicyclic sugar, such as a 4'-CH (CH$_3$)—O-2' group, a 4'-CH$_2$—O-2' group, or a 4'-(CH$_2$)$_2$—O-2' group.

In certain embodiments, at least one nucleoside of said modified oligonucleotide comprises a modified nucleobase. In certain embodiments, the modified nucleobase is a 5-methylcytosine.

Certain embodiments disclosed herein provide a compound or composition comprising a modified oligonucleotide with: a) a gap segment consisting of linked deoxynucleosides; b) a 5' wing segment consisting of linked nucleosides; and c) a 3' wing segment consisting of linked nucleosides. The gap segment is positioned between the 5' wing segment and the 3' wing segment and each nucleoside of each wing segment comprises a modified sugar. In certain embodiments, at least one internucleoside linkage is a phosphorothioate linkage. In certain embodiments, and at least one cytosine is a 5-methylcytosine.

In certain embodiments, the compounds or compositions disclosed herein further comprise a pharmaceutically acceptable carrier or diluent.

In certain embodiments, the compound or composition is co-administered with a second agent. In certain embodiments, the compound or composition and the second agent are administered concomitantly.

Certain embodiments provide uses of the compounds and compositions described herein for inhibiting DYRK1B expression. In certain embodiments, the compounds or compositions inhibit DYRK1B expression by at least 5%, at least 10%, at least 20%, at least 30%, at least 35%, at least 40%, at least 45%, at least 50%, at least 55%, at least 60%, at least 65%, at least 70%, at least 75%, at least 80%, at least 85%, or at least 90%. In certain embodiments, the compounds or compositions do not inhibit DYRK1A more than 30%, more than 25%, more than 20%, more than 15%, more than 10%, more than 5%. In certain embodiments, the compounds or compositions do not inhibit DYRK1A.

Certain embodiments provide uses of the compounds and compositions described herein for use in therapy. In certain embodiments, the therapy is used in treating, preventing, delaying the onset or slowing progression of a disease related to elevated expression of DYRK1B. In certain embodiments, the disease is a metabolic disease or disorder. In certain embodiments, the disease is a cardiovascular disease or disorder. In certain embodiments, the metabolic disease or disorder is diabetes mellitus. In certain embodiments, the metabolic disease or disorder is hyperglycemia. In certain embodiments, the metabolic disease or disorder is obesity. In certain embodiments, the metabolic disease or disorder is metabolic syndrome. In certain embodiments, the metabolic disease or disorder is essential hypertension. In certain embodiments, the metabolic disease or disorder is disorders of lipid metabolism. In certain embodiments, the metabolic disease or disorder is hypertensive heart disease. In certain embodiments, the metabolic disease or disorder is myocardial infarction. In certain embodiments, the metabolic disease or disorder is pulmonary heart disease. In certain embodiments, the metabolic disease or disorder is heart failure. In certain embodiments, the compound or composition comprises a modified oligonucleotide 8 to 80 linked nucleosides in length. In certain embodiments, the modified oligonucleotide consists of 10 to 30 linked nucleosides. In certain embodiments disclosed herein.

Certain embodiments disclosed herein provide uses of the compounds or compositions described herein comprising a DYRK1B modulator. In certain embodiments, the DYRK1B modulator is a DYRK1B-specific inhibitor. In certain embodiments, the DYRK1B-specific inhibitor is a nucleic acid, polypeptide, antibody, small molecules, or other agent capable of inhibiting the expression of DYRK1B. In certain embodiments, the nucleic acid is a compound or composition targeting DYRK1B. In certain embodiments, the compound or composition is single stranded. In certain embodiments, the compound or composition is double stranded. In certain embodiments, the compound is an antisense compound. In any of the foregoing embodiments, the compound can be an oligomeric compound. In certain embodiments, the compound or composition targeting DYRK1B comprises an oligonucleotide. In certain embodiments, the oligonucleotide is single stranded. In certain embodiments, the compound comprises deoxyribonucleotides. In certain embodiments, the compound is double-stranded and comprises ribonucleotides. In certain embodiments, the oligonucleotide is a modified oligonucleotide. In certain embodiments, the modified oligonucleotide is single stranded.

In any of the foregoing embodiments provide uses of compounds or compositions described herein, wherein the compound can consist of 8 to 80, 10 to 30, 12 to 50, 13 to 30, 13 to 50, 14 to 30, 14 to 50, 15 to 30, 15 to 50, 16 to 30, 16 to 50, 17 to 30, 17 to 50, 18 to 22, 18 to 24, 18 to 30, 18 to 50, 19 to 22, 19 to 30, 19 to 50, or 20 to 30 linked nucleosides. In certain embodiments, these compounds are oligonucleotides.

In certain embodiments, at least one internucleoside linkage of said modified oligonucleotide is a modified internucleoside linkage. In certain embodiments, each internucleoside linkage is a phosphorothioate internucleoside linkage.

In certain embodiments, any of the foregoing oligonucleotides comprises at least one modified sugar. In certain embodiments, at least one modified sugar comprises a 2'-O-methoxyethyl group. In certain embodiments, at least one modified sugar is a bicyclic sugar, such as a 4'-CH(CH$_3$)—O-2' group, a 4'-CH$_2$—O-2' group, or a 4'-(CH$_2$)$_2$—O-2'group.

In certain embodiments, at least one nucleoside of said modified oligonucleotide comprises a modified nucleobase. In certain embodiments, the modified nucleobase is a 5-methylcytosine.

Certain embodiments disclosed herein provide used of a compound or composition comprising a modified oligonucleotide with: a) a gap segment consisting of linked deoxynucleosides; b) a 5' wing segment consisting of linked nucleosides; and c) a 3' wing segment consisting of linked nucleosides. The gap segment is positioned between the 5' wing segment and the 3' wing segment and each nucleoside of each wing segment comprises a modified sugar. In certain embodiments, at least one internucleoside linkage is a phosphorothioate linkage. In certain embodiments, and at least one cytosine is a 5-methylcytosine.

In certain embodiments, the compounds or compositions disclosed herein further comprise a pharmaceutically acceptable carrier or diluent.

In certain embodiments, the animal is a human.

In certain embodiments, administration comprises parenteral administration. In certain embodiments, parenteral administration comprises subcutaneous administration. In certain embodiments, parenteral administration comprises intravenous administration.

In certain embodiments, the compounds or compositions disclosed herein are designated as a first agent and the methods or uses disclosed herein further comprise administering a second agent. In certain embodiments, the first agent and the second agent are co-administered. In certain embodiments, the first agent and the second agent are co-administered sequentially or concomitantly.

Certain Indications

Certain embodiments provided herein relate to methods of inhibiting DYRK1B expression or activity, which can be useful for treating, preventing, or ameliorating a disease associated with DYRK1B in an individual, by administration of a compound or composition that targets DYRK1B. In certain embodiments, the compound or composition does not target DYRK1A. In certain embodiments, such a compound comprises a DYRK1B-specific inhibitor. In certain embodiments, such a compound does not inhibit DYRK1A. In certain embodiments, the compound comprises an antisense compound or an oligomeric compound targeted to DYRK1B. In certain embodiments, the compound comprises a modified oligonucleotide targeted to DYRK1B. In certain embodiments, the antisense compound, oligomeric compound, or modified oligonucleotide does not target DYRK1A.

Examples of diseases associated with a DYRK1B treatable, preventable, and/or ameliorable with the methods provided herein include diabetes mellitus, hyperglycemia, obesity, metabolic syndrome, essential hypertension, disorders of lipid metabolism, hypertensive heart disease, myocardial infarction, pulmonary heart disease, heart failure, and other symptoms involving the cardiovascular system.

Certain embodiments disclose a method of inhibiting expression or activity of DYRK1B in a cell comprising contacting the cell with a compound or composition comprising a DYRK1B-specific inhibitor, thereby inhibiting expression or activity of DYRK1B in the cell. Certain embodiments disclose a method of inhibiting expression or activity of DYRK1B but not of DYRK1A in a cell, comprising contacting the cell with a compound or composition comprising a DYRK1B-specific inhibitor, thereby inhibiting expression or activity of DYRK1B but not of DYRK1A in the cell. In certain embodiments, the cell is in an individual who has, or is at risk of having a disease, disorder, condition, symptom, or physiological marker associated with a metabolic disease or disorder. In certain embodiments, the metabolic disease or disorder is diabetes mellitus. In certain embodiments, the metabolic disease or disorder is hyperglycemia. In certain embodiments, the metabolic disease or disorder is obesity. In certain embodiments, the metabolic disease or disorder is metabolic syndrome. In certain embodiments, the metabolic disease or disorder is essential hypertension. In certain embodiments, the metabolic disease or disorder is disorders of lipid metabolism. In certain embodiments, the metabolic disease or disorder is hypertensive heart disease. In certain embodiments, the metabolic disease or disorder is myocardial infarction. In certain embodiments, the metabolic disease or disorder is pulmonary heart disease. In certain embodiments, the metabolic disease or disorder is heart failure, and other symptoms involving the cardiovascular system. In certain embodiments, the DYRK1B-specific inhibitor is a nucleic acid, peptide, antibody, small molecule or other agent capable of inhibiting the expression or activity of the DYRK1B. In certain embodiments, the the DYRK1B-specific inhibitor is a nucleic acid, peptide, antibody, small molecule or other agent capable of inhibiting the expression or activity of the DYRK1B but does not inhibit the expression or activity of DYRK1A. In certain embodiments, the DYRK1B-specific inhibitor is an antisense compound or an oligomeric compound targeted to DYRK1B. In certain embodiments, the DYRK1B-specific inhibitor is oligonucleotide targeted to DYRK1B. In certain embodiments, the antisense compound, oligomeric compound, or modified oligonucleotide does not target DYRK1A. In certain embodiments, the compound or composition comprises a modified oligonucleotide 8 to 80 linked nucleosides in length. In certain embodiments, the compound or composition comprises a modified oligonucleotide 10 to 30 linked nucleosides in length. In certain embodiments, the compound comprising a modified oligonucleotide can be single-stranded. In certain embodiments, the compound comprising a modified oligonucleotide can be double-stranded.

In certain embodiments, a method of treating, preventing, delaying the onset, slowing progression, or ameliorating one of more diseases, disorders, conditions, symptoms, or physiologic markers associated with a metabolic disease or disorder in an individual comprises administering to the individual a compound or composition comprising a specific inhibitor of DYRK1B, thereby treating, preventing, delaying the onset, slowing the progression, or ameliorating the disease, disorder, symptom, or physiological marker associated with the metabolic disease or disorder. In certain embodiments, the compound or composition does not inhibit DYRK1A. In some embodiments, the individual is identified as having, or at risk of having, the disease, disorder, condition, symptom, or physiological marker. In certain embodiments, the metabolic disease or disorder is diabetes mellitus. In certain embodiments, the metabolic disease or disorder is hyperglycemia. In certain embodiments, the metabolic disease or disorder is obesity. In certain embodiments, the metabolic disease or disorder is metabolic syndrome. In certain embodiments, the metabolic disease or disorder is essential hypertension. In certain embodiments, the metabolic disease or disorder is disorders of lipid metabolism. In certain embodiments, the metabolic disease or disorder is hypertensive heart disease. In certain embodiments, the metabolic disease or disorder is myocardial infarction. In certain embodiments, the metabolic disease or disorder is pulmonary heart disease. In certain embodiments, the metabolic disease or disorder is heart failure, and other symptoms involving the cardiovascular system. In certain embodiments, the DYRK1B-specific inhibitor is a compound targeted to DYRK1B, such as an oligonucleotide targeted to DYRK1B. In certain embodiments, the DYRK1B-specific inhibitor is a compound comprising a modified oligonucleotide consisting of 8 to 80 linked nucleosides. In any of the foregoing embodiments, the compound can be single-stranded. In any of the foregoing embodiments, the compound can be an antisense compound or oligomeric compound. In certain embodiments, the compound is administered to the individual parenterally. In certain embodiments, administering the compound treats, ameliorates, or prevents a metabolic disease or disorder. In certain embodiments, the compound or composition comprises a modified oligonucleotide 8 to 80 linked nucleosides in length. In certain embodiments, the modified oligonucleotide consists of 10 to 30 linked nucleosides. In certain embodiments, the animal is human.

Certain embodiments disclosed herein provide a method of reducing blood glucose levels in an animal comprising administering to the animal a therapeutically effective amount of a compound or composition comprising a DYRK1B-specific inhibitor. In certain embodiments, the compound or composition does not inhibit DYRK1A. In certain embodiments, the DYRK1B-specific inhibitor is a nucleic acid, peptide, antibody, small molecule or other agent capable of inhibiting the expression of the DYRK1B. In certain embodiments, the DYRK1B-specific inhibitor comprises a compound described herein. In certain embodiments, the DYRK1B-specific inhibitor comprises an antisense compound or an oligomeric compound. In certain embodiments, the compound comprises a modified oligonucleotide. In certain embodiments, the antisense compound, oligomeric compound, or modified oligonucleotide does not target DYRK1A. In certain embodiments, the therapeutically effective amount of the compound or composition administered to the animal reduces glucose levels in the animal. In certain embodiments, the compound or composition comprises a modified oligonucleotide 8 to 80 linked nucleosides in length. In certain embodiments, the modified oligonucleotide consists of 10 to 30 linked nucleosides. In certain embodiments, the animal is human.

Certain embodiments disclosed herein provide a method of regulates insulin levels in an animal comprising administering to the animal a therapeutically effective amount of a compound or composition comprising a DYRK1B-specific inhibitor. In certain embodiments, the compound or composition does not inhibit DYRK1A. In certain embodiments, the DYRK1B-specific inhibitor is a nucleic acid, peptide, antibody, small molecule or other agent capable of inhibiting the expression of the DYRK1B. In certain embodiments, the DYRK1B-specific inhibitor comprises a compound described herein. In certain embodiments, the DYRK1B-specific inhibitor comprises an antisense compound or an oligomeric compound. In certain embodiments, the compound comprises a modified oligonucleotide. In certain embodiments, the antisense compound, oligomeric compound, or modified oligonucleotide does not target DYRK1A. In certain embodiments, the therapeutically effective amount of the compound or composition administered to the animal reduces regulates insulin levels in the animal. In certain embodiments, the compound or composition comprises a modified oligonucleotide 8 to 80 linked nucleosides in length. In certain embodiments, the modified oligonucleotide consists of 10 to 30 linked nucleosides. In certain embodiments, the animal is human.

Certain embodiments disclosed herein provide a method of increasing glucose tolerance in an animal comprising administering to the animal a therapeutically effective amount of a compound or composition comprising a DYRK1B-specific inhibitor. In certain embodiments, the compound or composition does not inhibit DYRK1A. In certain embodiments, the DYRK1B-specific inhibitor is a nucleic acid, peptide, antibody, small molecule or other agent capable of inhibiting the expression of the DYRK1B. In certain embodiments, the DYRK1B-specific inhibitor comprises a compound described herein. In certain embodiments, the DYRK1B-specific inhibitor comprises an antisense compound or an oligomeric compound. In certain embodiments, the compound comprises a modified oligonucleotide. In certain embodiments, the antisense compound, oligomeric compound, or modified oligonucleotide does not target DYRK1A. In certain embodiments, the therapeutically effective amount of the compound or composition administered to the animal increases glucose tolerance in the animal. In certain embodiments, the compound or composition comprises a modified oligonucleotide 8 to 80 linked nucleosides in length. In certain embodiments, the modified oligonucleotide consists of 10 to 30 linked nucleosides. In certain embodiments, the animal is human.

Certain embodiments disclosed herein provide a method of increasing insulin sensitivity in an animal comprising administering to the animal a therapeutically effective amount of a compound or composition comprising a DYRK1B-specific inhibitor. In certain embodiments, the compound or composition does not inhibit DYRK1A. In certain embodiments, the DYRK1B-specific inhibitor is a nucleic acid, peptide, antibody, small molecule or other agent capable of inhibiting the expression of the DYRK1B. In certain embodiments, the DYRK1B-specific inhibitor comprises a compound described herein. In certain embodiments, the DYRK1B-specific inhibitor comprises an antisense compound or an oligomeric compound. In certain embodiments, the compound comprises a modified oligonucleotide. In certain embodiments, the antisense compound, oligomeric compound, or modified oligonucleotide does not target DYRK1A. In certain embodiments, the therapeutically effective amount of the compound or composition administered to the animal increases insulin sensitivity in the animal. In certain embodiments, the compound or composition comprises a modified oligonucleotide 8 to 80 linked nucleosides in length. In certain embodiments, the modified oligonucleotide consists of 10 to 30 linked nucleosides. In certain embodiments, the animal is human.

Certain embodiments disclosed herein provide a method of reduces LDL cholesterol levels in an animal comprising administering to the animal a therapeutically effective amount of a compound or composition comprising a DYRK1B-specific inhibitor. In certain embodiments, the compound or composition does not inhibit DYRK1A. In certain embodiments, the DYRK1B-specific inhibitor is a nucleic acid, peptide, antibody, small molecule or other agent capable of inhibiting the expression of the DYRK1B. In certain embodiments, the DYRK1B-specific inhibitor comprises a compound described herein. In certain embodiments, the DYRK1B-specific inhibitor comprises an antisense compound or an oligomeric compound. In certain embodiments, the compound comprises a modified oligonucleotide. In certain embodiments, the antisense compound, oligomeric compound, or modified oligonucleotide does not target DYRK1A. In certain embodiments, the therapeutically effective amount of the compound or composition administered to the animal reduces LDL cholesterol in the animal. In certain embodiments, the compound or composition comprises a modified oligonucleotide 8 to 80 linked nucleosides in length. In certain embodiments, the modified oligonucleotide consists of 10 to 30 linked nucleosides. In certain embodiments, the animal is human.

Certain embodiments disclosed herein provide a method of reduces triglyceride levels in an animal comprising administering to the animal a therapeutically effective amount of a compound or composition comprising a DYRK1B-specific inhibitor. In certain embodiments, the compound or composition does not inhibit DYRK1A. In certain embodiments, the DYRK1B-specific inhibitor is a nucleic acid, peptide, antibody, small molecule or other agent capable of inhibiting the expression of the DYRK1B. In certain embodiments, the DYRK1B-specific inhibitor comprises a compound described herein. In certain embodiments, the DYRK1B-specific inhibitor comprises an antisense compound or an oligomeric compound. In certain embodiments, the compound comprises a modified oligonucleotide. In certain embodiments, the antisense compound, oligomeric compound, or modified oligonucleotide does not target DYRK1A. In certain embodiments, the therapeutically effective amount of the compound or composition administered to the animal reduces triglyceride levels in the animal. In certain embodiments, the compound or composition comprises a modified oligonucleotide 8 to 80 linked nucleosides in length. In certain embodiments, the modified oligonucleotide consists of 10 to 30 linked nucleosides. In certain embodiments, the animal is human.

Certain embodiments disclosed herein provide a method of reduces blood pressure in an animal comprising administering to the animal a therapeutically effective amount of a compound or composition comprising a DYRK1B-specific inhibitor. In certain embodiments, the compound or composition does not inhibit DYRK1A. In certain embodiments, the DYRK1B-specific inhibitor is a nucleic acid, peptide, antibody, small molecule or other agent capable of inhibiting the expression of the DYRK1B. In certain embodiments, the DYRK1B-specific inhibitor comprises a compound described herein. In certain embodiments, the DYRK1B-specific inhibitor comprises an antisense compound or an oligomeric compound. In certain embodiments, the compound comprises a modified oligonucleotide. In certain embodiments, the antisense compound, oligomeric compound, or modified oligonucleotide does not target DYRK1A. In certain embodiments, the therapeutically effective amount of the compound or composition administered to the animal reduces blood pressure in the animal. In certain embodiments, the compound or composition comprises a modified oligonucleotide 8 to 80 linked nucleosides in length. In certain embodiments, the modified oligonucleotide consists of 10 to 30 linked nucleosides. In certain embodiments, the animal is human.

Certain embodiments disclosed herein provide a method of reduces body-mass index in an animal comprising administering to the animal a therapeutically effective amount of a compound or composition comprising a DYRK1B-specific inhibitor. In certain embodiments, the compound or composition does not inhibit DYRK1A. In certain embodiments, the DYRK1B-specific inhibitor is a nucleic acid, peptide, antibody, small molecule or other agent capable of inhibiting the expression of the DYRK1B. In certain embodiments, the DYRK1B-specific inhibitor comprises a compound described herein. In certain embodiments, the DYRK1B-specific inhibitor comprises an antisense compound or an oligomeric compound. In certain embodiments, the compound comprises a modified oligonucleotide. In certain embodiments, the antisense compound, oligomeric compound, or modified oligonucleotide does not target DYRK1A. In certain embodiments, the therapeutically effective amount of the compound or composition administered to the animal reduces body-mass index in the animal. In certain embodiments, the compound or composition comprises a modified oligonucleotide 8 to 80 linked nucleosides in length. In certain embodiments, the modified oligonucleotide consists of 10 to 30 linked nucleosides. In certain embodiments, the animal is human.

In certain embodiments, administering the compound or composition disclosed herein decreases blood glucose levels, regulates insulin levels, increases glucose tolerance, increases insulin sensitivity, reduces LDL cholesterol levels, decreases triglyceride levels, reduces blood pressure and reduces body-mass index, or a combination thereof. In certain embodiments, blood glucose levels were independently reduced by at least 5%, at least 10%, at least 20%, at least 30%, at least 35%, at least 40%, at least 45% or at least 50%. In certain embodiments, insulin sensitivity was independently increased by at least 5%, at least 10%, at least 20%, at least 30%, at least 35%, at least 40%, at least 45% or at least 50%. In certain embodiments, glucose tolerance was independently increased by at least 5%, at least 10%, at least 20%, at least 30%, at least 35%, at least 40%, at least 45% or at least 50%. In certain embodiments, LDL cholesterol levels were independently decreased by at least 5%, at least 10%, at least 20%, at least 30%, at least 35%, at least 40%, at least 45% or at least 50%. In certain embodiments, triglyceride levels were independently decreased by at least 5%, at least 10%, at least 20%, at least 30%, at least 35%, at least 40%, at least 45% or at least 50%. In certain embodiments, blood pressure levels were independently decreased by at least 5%, at least 10%, at least 20%, at least 30%, at least 35%, at least 40%, at least 45% or at least 50%. In certain embodiments, body-mass index was independently decreased by at least 5%, at least 10%, at least 20%, at least 30%, at least 35%, at least 40%, at least 45% or at least 50%.

Cetrtain embodiments are drawn to compounds or compositions described herein for use in therapy. Certain embodiments are drawn to a compound or composition comprising a DYRK1B-specific inhibitor for use in treating a metabolic disease or disorder. In certain embodiments, the compound or composition does not inhibit DYRK1A. In certain embodiments, the metabolic disease or disorder may be one or more of diabetes mellitus, hyperglycemia, obesity, metabolic syndrome, essential hypertension, disorders of lipid metabolism, hypertensive heart disease, myocardial infarction, pulmonary heart disease, heart failure, and other symptoms involving the cardiovascular system. In certain embodiments, the DYRK1B-specific inhibitor is a compound targeted to DYRK1B, such as an oligonucleotide targeted to a DYRK1B. In certain embodiments, the DYRK1B-specific inhibitor is a compound comprising a modified oligonucleotide consisting of 8 to 80 linked nucleosides. In any of the foregoing embodiments, the compound can be an antisense compound or oligomeric compound. In certain embodiments, the antisense compound, oligomeric compound, or modified oligonucleotide does not target DYRK1A. In any of the foregoing embodiments, the compound can be single-stranded or double-stranded. In certain embodiments, the modified oligonucleotide consists of 10 to 30 linked nucleosides.

In certain embodiments, use of a compound or composition disclosed herein results in blood glucose levels independently reduced by at least 5%, at least 10%, at least 20%, at least 30%, at least 35%, at least 40%, at least 45% or at least 50%. In certain embodiments, use of a compound or composition disclosed herein results in insulin sensitivity independently increased by at least 5%, at least 10%, at least 20%, at least 30%, at least 35%, at least 40%, at least 45% or at least 50%. In certain embodiments, use of a compound or composition disclosed herein results in glucose tolerance independently increased by at least 5%, at least 10%, at least 20%, at least 30%, at least 35%, at least 40%, at least 45% or at least 50%. In certain embodiments, use of a compound or composition disclosed herein results in LDL cholesterol levels independently decreased by at least 5%, at least 10%, at least 20%, at least 30%, at least 35%, at least 40%, at least 45% or at least 50%. In certain embodiments, use of a compound or composition disclosed herein results in triglyceride levels independently decreased by at least 5%, at least 10%, at least 20%, at least 30%, at least 35%, at least 40%, at least 45% or at least 50%. In certain embodiments, use of a compound or composition disclosed herein results in blood pressure levels independently decreased by at least 5%, at least 10%, at least 20%, at least 30%, at least 35%, at least 40%, at least 45% or at least 50%. In certain embodiments, use of a compound or composition disclosed herein results in body-mass index independently decreased by at least 5%, at least 10%, at least 20%, at least 30%, at least 35%, at least 40%, at least 45% or at least 50%.

Certain embodiments provide the use of a compound or composition as described herein in the manufacture or preparation of a medicament for treating, ameliorating, delaying or preventing one or more diseases, disorders, conditions, symptoms or physiological markers associated with DYRK1B. In certain embodiments, the use of the compound or composition does not inhibit DYRK1A. In certain embodiments, the compound or composition as described herein is used in the manufacture of a medicament for treating, ameliorating, delaying or preventing a metabolic disease or disorder, or a symptom or physiological marker thereof. In certain embodiments, the disease is a metabolic disease or disorder. In certain embodiments, the disease is a cardiovascular disease or disorder. In certain embodiments, the metabolic disease or disorder is diabetes mellitus. In certain embodiments, the metabolic disease or disorder is hyperglycemia. In certain embodiments, the metabolic disease or disorder is obesity. In certain embodiments, the metabolic disease or disorder is metabolic syndrome. In certain embodiments, the metabolic disease or disorder is essential hypertension. In certain embodiments, the metabolic disease or disorder is disorders of lipid metabolism. In certain embodiments, the metabolic disease or disorder is hypertensive heart disease. In certain embodiments, the metabolic disease or disorder is myocardial infarction. In certain embodiments, the metabolic disease or disorder is pulmonary heart disease. In certain embodiments, the metabolic disease or disorder is heart failure. In certain embodiments, the compound or composition comprises a modified oligonucleotide 8 to 80 linked nucleosides in length. In certain embodiments, the modified oligonucleotide consists of 10 to 30 linked nucleosides. In certain embodiments, the modified oligonucleotide does not target DYRK1A. In certain embodiments disclosed herein, the animal is human.

Certain embodiments are drawn to use of a DYRK1B-specific inhibitor for the manufacture or preparation of a medicament for treating a metabolic disease or disorder. In certain embodiments, the use of the compound or composition does not inhibit DYRK1A. Examples of such metabolic diseases or disorders are diabetes mellitus, hyperglycemia, obesity, metabolic syndrome, essential hypertension, disorders of lipid metabolism, hypertensive heart disease, myocardial infarction, pulmonary heart disease, heart failure, and other symptoms involving the cardiovascular system. In certain embodiments, the DYRK1B-specific inhibitor is a compound targeted to DYRK1B, such as an oligonucleotide targeted to DYRK1B. In certain embodiments, the DYRK1B-specific inhibitor is a compound comprising a modified oligonucleotide consisting of 8 to 80 linked nucleosides. In any of the foregoing embodiments, the compound can be an antisense compound or oligomeric compound. In certain embodiments, the antisense compound, oligomeric compound, or modified oligonucleotide does not target DYRK1A. In any of the foregoing embodiments, the compound can be single-stranded or double-stranded. In certain embodiments, the modified oligonucleotide consists of 10 to 30 linked nucleosides.

Certain embodiments are drawn to use of a DYRK1B-specific inhibitor for the manufacture of a medicament for decreasing blood glucose levels, regulating insulin levels, increasing glucose tolerance, increasing insulin sensitivity, reducing LDL cholesterol levels, decreasing triglyceride levels, reducing blood pressure and reducing body-mass index, or a combination thereof in an individual having or at risk of having a metabolic disease or disorder. In certain embodiments, the disease is a cardiovascular disease or disorder. In certain embodiments, the metabolic disease or disorder is diabetes mellitus. In certain embodiments, the metabolic disease or disorder is hyperglycemia. In certain embodiments, the metabolic disease or disorder is obesity. In certain embodiments, the metabolic disease or disorder is metabolic syndrome. In certain embodiments, the metabolic disease or disorder is essential hypertension. In certain embodiments, the metabolic disease or disorder is disorders of lipid metabolism. In certain embodiments, the metabolic disease or disorder is hypertensive heart disease. In certain embodiments, the metabolic disease or disorder is myocardial infarction. In certain embodiments, the metabolic disease or disorder is pulmonary heart disease. In certain embodiments, the metabolic disease or disorder is heart failure. In certain embodiments, the DYRK1B-specific inhibitor is a compound targeted to DYRK1B, such as an oligonucleotide targeted to DYRK1B. In certain embodiments, the DYRK1B-specific inhibitor is a compound comprising a modified oligonucleotide consisting of 8 to 80 linked nucleosides. In any of the foregoing embodiments, the compound can be an antisense compound or oligomeric compound. In certain embodiments, the antisense compound, oligomeric compound, or modified oligonucleotide does not target DYRK1A. In any of the foregoing embodiments, the compound can be single-stranded or double-stranded. In certain embodiments, the modified oligonucleotide consists of 10 to 30 linked nucleosides.

In any of the foregoing methods or uses, the compound can be an antisense compound targeted to DYRK1B. In certain embodiments, the compound comprises an oligonucleotide, for example an oligonucleotide consisting of 8 to 80 linked nucleosides, 10 to 30 linked nucleosides, 12 to 30 linked nucleosides, or 20 linked nucleosides. In certain embodiments, the oligonucleotide comprises at least one modified internucleoside linkage, at least one modified sugar and/or at least one modified nucleobase. In certain embodiments, the modified internucleoside linkage is a phosphorothioate internucleoside linkage, the modified sugar is a bicyclic sugar or a 2'-O-methoxyethyl, and the modified nucleobase is a 5-methylcytosine. In certain embodiments, the modified oligonucleotide comprises a gap segment consisting of linked deoxynucleosides; a 5' wing segment consisting of linked nucleosides; and a 3' wing segment consisting of linked nucleosides, wherein the gap segment is positioned immediately adjacent to and between the 5' wing segment and the 3' wing segment and wherein each nucleoside of each wing segment comprises a modified sugar.

In any of the foregoing methods or uses, the compound comprises or consists of a modified oligonucleotide 12 to 30 linked nucleosides in length, wherein the modified oligonucleotide comprises:

a gap segment consisting of linked 2'-deoxynucleosides;
a 5' wing segment consisting of linked nucleosides; and
a 3' wing segment consisting of linked nucleosides;

wherein the gap segment is positioned between the 5' wing segment and the 3' wing segment and wherein each nucleoside of each wing segment comprises a modified sugar.

In any of the foregoing methods or uses, the compound can be administered parenterally. For example, in certain embodiments the compound can be administered through injection or infusion. Parenteral administration includes subcutaneous administration, intravenous administration, intramuscular administration, intraarterial administration, intraperitoneal administration, or intracranial administration.

Certain Compounds

In certain embodiments, compounds described herein are antisense compounds. In certain embodiments, the antisense compound comprises or consists of an oligomeric compound. In certain embodiments, the oligomeric compound comprises a modified oligonucleotide. In certain embodiments, the modified oligonucleotide has a nucleobase sequence complementary to that of a target nucleic acid.

In certain embodiments, a compound described herein comprises or consists of a modified oligonucleotide. In certain embodiments, the modified oligonucleotide has a nucleobase sequence complementary to that of a target nucleic acid.

In certain embodiments, a compound or antisense compound is single-stranded. Such a single-stranded compound or antisense compound comprises or consists of an oligomeric compound. In certain embodiments, such an oligomeric compound comprises or consists of an oligonucleotide. In certain embodiments, the oligonucleotide is an antisense oligonucleotide. In certain embodiments, the oligonucleotide is modified. In certain embodiments, the oligonucleotide of a single-stranded antisense compound or oligomeric compound comprises a self-complementary nucleobase sequence.

In certain embodiments, compounds are double-stranded. Such double-stranded compounds comprise a first modified oligonucleotide having a region complementary to a target nucleic acid and a second modified oligonucleotide having a region complementary to the first modified oligonucleotide. In certain embodiments, the modified oligonucleotide is an RNA oligonucleotide. In such embodiments, the thymine nucleobase in the modified oligonucleotide is replaced by a uracil nucleobase. In certain embodiments, compound comprises a conjugate group. In certain embodiments, each modified oligonucleotide is 12-30 linked nucleosides in length.

In certain embodiments, compounds are double-stranded. Such double-stranded compounds comprise a first oligomeric compound having a region complementary to a target nucleic acid and a second oligomeric compound having a region complementary to the first oligomeric compound. The first oligomeric compound of such double stranded compounds typically comprises or consists of a modified oligonucleotide. The oligonucleotide of the second oligomeric compound of such double-stranded compound may be modified or unmodified. The oligomeric compounds of double-stranded compounds may include non-complementary overhanging nucleosides.

Examples of single-stranded and double-stranded compounds include but are not limited to oligonucleotides, siRNAs, microRNA targeting oligonucleotides, and single-stranded RNAi compounds, such as small hairpin RNAs (shRNAs), single-stranded siRNAs (ssRNAs), and microRNA mimics.

In certain embodiments, a compound described herein has a nucleobase sequence that, when written in the 5' to 3' direction, comprises the reverse complement of the target segment of a target nucleic acid to which it is targeted.

In certain embodiments, a compound described herein comprises an oligonucleotide 10 to 30 linked subunits in length. In certain embodiments, compound described herein comprises an oligonucleotide is 12 to 30 linked subunits in length. In certain embodiments, compound described herein comprises an oligonucleotide is 12 to 22 linked subunits in length. In certain embodiments, compound described herein comprises an oligonucleotide is 14 to 30 linked subunits in length. In certain embodiments, compound described herein comprises an oligonucleotide is 14 to 20 linked subunits in length. In certain embodiments, compound described herein comprises an oligonucleotide is 15 to 30 linked subunits in length. In certain embodiments, compound described herein comprises an oligonucleotide is 15 to 20 linked subunits in length. In certain embodiments, compound described herein comprises an oligonucleotide is 16 to 30 linked subunits in length. In certain embodiments, compound described herein comprises an oligonucleotide is 16 to 20 linked subunits in length. In certain embodiments, compound described herein comprises an oligonucleotide is 17 to 30 linked subunits in length. In certain embodiments, compound described herein comprises an oligonucleotide is 17 to 20 linked subunits in length. In certain embodiments, compound described herein comprises an oligonucleotide is 18 to 30 linked subunits in length. In certain embodiments, compound described herein comprises an oligonucleotide is 18 to 21 linked subunits in length. In certain embodiments, compound described herein comprises an oligonucleotide is 18 to 20 linked subunits in length. In certain embodiments, compound described herein comprises an oligonucleotide is 20 to 30 linked subunits in length. In other words, such oligonucleotides are from 12 to 30 linked subunits, 14 to 30 linked subunits, 14 to 20 subunits, 15 to 30 subunits, 15 to 20 subunits, 16 to 30 subunits, 16 to 20 subunits, 17 to 30 subunits, 17 to 20 subunits, 18 to 30 subunits, 18 to 20 subunits, 18 to 21 subunits, 20 to 30 subunits, or 12 to 22 linked subunits, respectively. In certain embodiments, a compound described herein comprises an oligonucleotide 14 linked subunits in length. In certain embodiments, a compound described herein comprises an oligonucleotide 16 linked subunits in length. In certain embodiments, a compound described herein comprises an oligonucleotide 17 linked subunits in length. In certain embodiments, compound described herein comprises an oligonucleotide 18 linked subunits in length. In certain embodiments, a compound described herein comprises an oligonucleotide 19 linked subunits in length. In certain embodiments, a compound described herein comprises an oligonucleotide 20 linked subunits in length. In other embodiments, a compound described herein comprises an oligonucleotide 8 to 80, 12 to 50, 13 to 30, 13 to 50, 14 to 30, 14 to 50, 15 to 30, 15 to 50, 16 to 30, 16 to 50, 17 to 30, 17 to 50, 18 to 22, 18 to 24, 18 to 30, 18 to 50, 19 to 22, 19 to 30, 19 to 50, or 20 to 30 linked subunits. In certain such embodiments, the compound described herein comprises an oligonucleotide 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked subunits in length, or a range defined by any two of the above values. In some embodiments the linked subunits are nucleotides, nucleosides, or nucleobases.

In certain embodiments, compounds may be shortened or truncated. For example, a single subunit may be deleted from the 5' end (5' truncation), or alternatively from the 3' end (3' truncation). A shortened or truncated compound targeted to a DYRK1B nucleic acid may have two subunits deleted from the 5' end, or alternatively may have two subunits deleted from the 3' end, of the compound. Alternatively, the deleted nucleosides may be dispersed throughout the compound.

When a single additional subunit is present in a lengthened compound, the additional subunit may be located at the 5' or 3' end of the compound. When two or more additional subunits are present, the added subunits may be adjacent to each other, for example, in a compound having two subunits added to the 5' end (5' addition), or alternatively to the 3' end (3' addition), of the compound. Alternatively, the added subunits may be dispersed throughout the compound.

It is possible to increase or decrease the length of a compound, such as an oligonucleotide, and/or introduce mismatch bases without eliminating activity (Woolf et al. (Proc. Natl. Acad. Sci. USA 89:7305-7309, 1992; Gautschi et al. *J. Natl. Cancer Inst.* 93:463-471, March 2001; Maher and Dolnick *Nuc. Acid. Res.* 16:3341-3358, 1988). However, seemingly small changes in oligonucleotide sequence, chemistry and motif can make large differences in one or more of the many properties required for clinical development (Seth et al. *J. Med. Chem.* 2009, 52, 10; Egli et al. *J. Am. Chem. Soc.* 2011, 133, 16642).

In certain embodiments, compounds described herein are interfering RNA compounds (RNAi), which include double-stranded RNA compounds (also referred to as short-interfering RNA or siRNA) and single-stranded RNAi compounds (or ssRNA). Such compounds work at least in part through the RISC pathway to degrade and/or sequester a target nucleic acid (thus, include microRNA/microRNA-mimic compounds). As used herein, the term siRNA is meant to be equivalent to other terms used to describe nucleic acid molecules that are capable of mediating sequence specific RNAi, for example short interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically modified siRNA, post-transcriptional gene silencing RNA (ptgsRNA), and others. In addition, as used herein, the term RNAi is meant to be equivalent to other terms used to describe sequence specific RNA interference, such as post transcriptional gene silencing, translational inhibition, or epigenetics.

In certain embodiments, a double-stranded compound comprises a first strand comprising the nucleobase sequence complementary to a target region of a DYRK1B nucleic acid and a second strand. In certain embodiments, the double-stranded compound comprises ribonucleotides in which the first strand has uracil (U) in place of thymine (T) and is complementary to a target region. In certain embodiments, a double-stranded compound comprises (i) a first strand comprising a nucleobase sequence complementary to a target region of a DYRK1B nucleic acid, and (ii) a second strand. In certain embodiments, the double-stranded compound comprises one or more modified nucleotides in which the 2' position in the sugar contains a halogen (such as fluorine group; 2'-F) or contains an alkoxy group (such as a methoxy group; 2'-OMe). In certain embodiments, the double-stranded compound comprises at least one 2'-F sugar modification and at least one 2'-OMe sugar modification. In certain embodiments, the at least one 2'-F sugar modification and at least one 2'-OMe sugar modification are arranged in an alternating pattern for at least 2, 3, 4, 5, 6, 7, 8, 9, 10, 11, 12, 13, 14, 15, 16, 17, 18, 19, or 20 contiguous nucleobases along a strand of the dsRNA compound. In certain embodiments, the double-stranded compound comprises one or more linkages between adjacent nucleotides other than a naturally-occurring phosphodiester linkage. Examples of such linkages include phosphoramide, phosphorothioate, and phosphorodithioate linkages. The double-stranded compounds may also be chemically modified nucleic acid molecules as taught in U.S. Pat. No. 6,673,661. In other embodiments, the dsRNA contains one or two capped strands, as disclosed, for example, by WO 00/63364, filed Apr. 19, 2000. In certain embodiments, the first strand of the double-stranded compound is an siRNA guide strand and the second strand of the double-stranded compound is an siRNA passenger strand. In certain embodiments, the second strand of the double-stranded compound is complementary to the first strand. In certain embodiments, each strand of the double-stranded compound consists of 16, 17, 18, 19, 20, 21, 22, or 23 linked nucleosides.

In certain embodiments, a single-stranded compound described herein can comprise any of the oligonucleotide sequences targeted to a DYRK1B described herein. In certain embodiments, such a single-stranded compound is a single-stranded RNAi (ssRNAi) compound. In certain embodiments, a ssRNAi compound comprises the nucleobase sequence complementary to a target region of a DYRK1B nucleic acid. In certain embodiments, the ssRNAi compound comprises ribonucleotides in which uracil (U) is in place of thymine (T). In certain embodiments, ssRNAi compound comprises a nucleobase sequence complementary to a target region of a DYRK1B nucleic acid. In certain embodiments, a ssRNAi compound comprises one or more modified nucleotides in which the 2' position in the sugar contains a halogen (such as fluorine group; 2'-F) or contains an alkoxy group (such as a methoxy group; 2'-OMe). In certain embodiments, a ssRNAi compound comprises at least one 2'-F sugar modification and at least one 2'-OMe sugar modification. In certain embodiments, the at least one 2'-F sugar modification and at least one 2'-OMe sugar modification are arranged in an alternating pattern for at least 2, 3, 4, 5, 6, 7, 8, 9, 10, 11, 12, 13, 14, 15, 16, 17, 18, 19, or 20 contiguous nucleobases along a strand of the ssRNAi compound. In certain embodiments, the ssRNAi compound comprises one or more linkages between adjacent nucleotides other than a naturally-occurring phosphodiester linkage. Examples of such linkages include phosphoramide, phosphorothioate, and phosphorodithioate linkages. The ssRNAi compounds may also be chemically modified nucleic acid molecules as taught in U.S. Pat. No. 6,673,661. In other embodiments, the ssRNAi contains a capped strand, as disclosed, for example, by WO 00/63364, filed Apr. 19, 2000. In certain embodiments, the ssRNAi compound consists of 16, 17, 18, 19, 20, 21, 22, or 23 linked nucleosides.

In certain embodiments, compounds described herein comprise modified oligonucleotides. Certain modified oligonucleotides have one or more asymmetric center and thus give rise to enantiomers, diastereomers, and other stereoisomeric configurations that may be defined, in terms of absolute stereochemistry, as (R) or (S), as α or β, such as for sugar anomers, or as (D) or (L) such as for amino acids etc. Included in the modified oligonucleotides provided herein are all such possible isomers, including their racemic and optically pure forms, unless specified otherwise. Likewise, all cis- and trans-isomers and tautomeric forms are also included.

Certain Mechanisms

In certain embodiments, compounds described herein comprise or consist of modified oligonucleotides. In certain embodiments, compounds described herein are antisense compounds. In certain embodiments, such antisense compounds comprise oligomeric compounds. In certain embodiments, compounds described herein are capable of hybridizing to a target nucleic acid, resulting in at least one antisense activity. In certain embodiments, compounds described herein selectively affect one or more target nucleic acid. Such selective compounds comprise a nucleobase sequence that hybridizes to one or more target nucleic acid, resulting in one or more desired antisense activity and does not hybridize to one or more non-target nucleic acid or does not hybridize to one or more non-target nucleic acid in such a way that results in a significant undesired antisense activity.

In certain antisense activities, hybridization of a compound described herein to a target nucleic acid results in recruitment of a protein that cleaves the target nucleic acid. For example, certain compounds described herein result in RNase H mediated cleavage of the target nucleic acid. RNase H is a cellular endonuclease that cleaves the RNA strand of an RNA:DNA duplex. The DNA in such an RNA:DNA duplex need not be unmodified DNA. In certain embodiments, compounds described herein are sufficiently "DNA-like" to elicit RNase H activity. Further, in certain embodiments, one or more non-DNA-like nucleoside in the gap of a gapmer is tolerated.

In certain antisense activities, compounds described herein or a portion of the compound is loaded into an RNA-induced silencing complex (RISC), ultimately resulting in cleavage of the target nucleic acid. For example, certain compounds described herein result in cleavage of the target nucleic acid by Argonaute. Compounds that are loaded into RISC are RNAi compounds. RNAi compounds may be double-stranded (siRNA) or single-stranded (ssRNA).

In certain embodiments, hybridization of compounds described herein to a target nucleic acid does not result in recruitment of a protein that cleaves that target nucleic acid. In certain such embodiments, hybridization of the compound to the target nucleic acid results in alteration of splicing of the target nucleic acid. In certain embodiments, hybridization of the compound to a target nucleic acid results in inhibition of a binding interaction between the target nucleic acid and a protein or other nucleic acid. In certain such embodiments, hybridization of the compound to a target nucleic acid results in alteration of translation of the target nucleic acid.

Antisense activities may be observed directly or indirectly. In certain embodiments, observation or detection of an antisense activity involves observation or detection of a change in an amount of a target nucleic acid or protein encoded by such target nucleic acid, a change in the ratio of splice variants of a nucleic acid or protein, and/or a phenotypic change in a cell or animal.

Target Nucleic Acids, Target Regions and Nucleotide Sequences

In certain embodiments, compounds described herein comprise or consist of an oligonucleotide comprising a region that is complementary to a target nucleic acid. In certain embodiments, the target nucleic acid is an endogenous RNA molecule. In certain such embodiments, the target nucleic acid is selected from:

an mRNA and a pre-mRNA, including intronic, exonic and untranslated regions. In certain embodiments, the target nucleic acid is a pre-mRNA. In certain such embodiments, the target region is entirely within an intron. In certain embodiments, the target region spans an intron/exon junction. In certain embodiments, the target region is at least 50% within an intron. In certain embodiments, the target region is an lncRNA. Human gene sequences that encode a DYRK1B include, without limitation, the following gene sequences: the complement of RefSeqNo. NT_011109.17 truncated from nucleotides 12584000 to 12594000 (SEQ ID NO: 2); RefSeqNo. NM_004714.2 (SEQ ID NO: 3); RefSeqNo. NM_006483.2 (SEQ ID NO: 4); and RefSeqNo. NM_006484.2 (SEQ ID NO: 5). Murine sequences that encode a DYRK1B include, without limitation, the following gene sequences: RefSeqNo. NT_187034.1 truncated from nucleotides 25178000 to 25189000 (SEQ ID NO: 6); RefSeqNo. NM_001037957.3 (SEQ ID NO: 7); RefSeqNo. NM_001271370.1 (SEQ ID NO: 8); and RefSeqNo. NM_010092.2 (SEQ ID NO: 9).

Hybridization

In some embodiments, hybridization occurs between a compound disclosed herein and a DYRK1B nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Hybridization conditions are sequence-dependent and are determined by the nature and composition of the nucleic acid molecules to be hybridized.

Methods of determining whether a sequence is specifically hybridizable to a target nucleic acid are well known in the art. In certain embodiments, the compounds provided herein are specifically hybridizable with a DYRK1B nucleic acid.

Complementarity

An oligonucleotide is said to be complementary to another nucleic acid when the nucleobase sequence of such oligonucleotide or one or more regions thereof matches the nucleobase sequence of another oligonucleotide or nucleic acid or one or more regions thereof when the two nucleobase sequences are aligned in opposing directions. Nucleobase matches or complementary nucleobases, as described herein, are limited to adenine (A) and thymine (T), adenine (A) and uracil (U), cytosine (C) and guanine (G), and 5-methyl cytosine (mC) and guanine (G) unless otherwise specified. Complementary oligonucleotides and/or nucleic acids need not have nucleobase complementarity at each nucleoside and may include one or more nucleobase mismatches. An oligonucleotide is fully complementary or 100% complementary when such oligonucleotides have nucleobase matches at each nucleoside without any nucleobase mismatches.

In certain embodiments, compounds described herein comprise or consist of modified oligonucleotides. In certain embodiments, compounds described herein are antisense compounds. In certain embodiments, compounds comprise oligomeric compounds. Non-complementary nucleobases between a compound and a DYRK1B nucleic acid may be tolerated provided that the compound remains able to specifically hybridize to a target nucleic acid. Moreover, a compound may hybridize over one or more segments of a DYRK1B nucleic acid such that intervening or adjacent segments are not involved in the hybridization event (e.g., a loop structure, mismatch or hairpin structure).

In certain embodiments, the compounds provided herein, or a specified portion thereof, are, or are at least, 70%, 80%, 85%, 86%, 87%, 88%, 89%, 90%, 91%, 92%, 93%, 94%, 95%, 96%, 97%, 98%, 99%, or 100% complementary to a DYRK1B nucleic acid, a target region, target segment, or specified portion thereof. Percent complementarity of a compound with a target nucleic acid can be determined using routine methods.

For example, a compound in which 18 of 20 nucleobases of the compound are complementary to a target region, and would therefore specifically hybridize, would represent 90 percent complementarity. In this example, the remaining non-complementary nucleobases may be clustered or interspersed with complementary nucleobases and need not be contiguous to each other or to complementary nucleobases. As such, a compound which is 18 nucleobases in length having four non-complementary nucleobases which are flanked by two regions of complete complementarity with the target nucleic acid would have 77.8% overall complementarity with the target nucleic acid and would thus fall within the scope of the present invention. Percent complementarity of a compound with a region of a target nucleic acid can be determined routinely using BLAST programs (basic local alignment search tools) and PowerBLAST programs known in the art (Altschul et al., J. Mol. Biol., 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, compounds described herein, or specified portions thereof, are fully complementary (i.e. 100% complementary) to a target nucleic acid, or specified portion thereof. For example, a compound may be fully complementary to a DYRK1B nucleic acid, or a target region, or a target segment or target sequence thereof. As used herein, "fully complementary" means each nucleobase of a compound is capable of precise base pairing with the corresponding nucleobases of a target nucleic acid. For example, a 20 nucleobase compound is fully complementary to a target sequence that is 400 nucleobases long, so long as there is a corresponding 20 nucleobase portion of the target nucleic acid that is fully complementary to the compound. Fully complementary can also be used in reference to a specified portion of the first and/or the second nucleic acid. For example, a 20 nucleobase portion of a 30 nucleobase compound can be "fully complementary" to a target sequence that is 400 nucleobases long. The 20 nucleobase portion of the 30 nucleobase compound is fully complementary to the target sequence if the target sequence has a corresponding 20 nucleobase portion wherein each nucleobase is complementary to the 20 nucleobase portion of the compound. At the same time, the entire 30 nucleobase compound may or may not be fully complementary to the target sequence, depending on whether the remaining 10 nucleobases of the compound are also complementary to the target sequence.

In certain embodiments, compounds described herein comprise one or more mismatched nucleobases relative to the target nucleic acid. In certain such embodiments, antisense activity against the target is reduced by such mismatch, but activity against a non-target is reduced by a greater amount. Thus, in certain such embodiments selectivity of the compound is improved. In certain embodiments, the mismatch is specifically positioned within an oligonucleotide having a gapmer motif. In certain such embodiments, the mismatch is at position 1, 2, 3, 4, 5, 6, 7, or 8 from the 5'-end of the gap region. In certain such embodiments, the mismatch is at position 9, 8, 7, 6, 5, 4, 3, 2, 1 from the 3'-end of the gap region. In certain such embodiments, the mismatch is at position 1, 2, 3, or 4 from the 5'-end of the wing region. In certain such embodiments, the mismatch is at position 4, 3, 2, or 1 from the 3'-end of the wing region. In certain embodiments, the mismatch is specifically positioned within an oligonucleotide not having a gapmer motif. In certain such embodiments, the mismatch is at position 1, 2, 3, 4, 5, 6, 7, 8, 9, 10, 11, or 12 from the 5'-end of the oligonucleotide. In certain such embodiments, the mismatch is at position, 2, 3, 4, 5, 6, 7, 8, 9, 10, 11, or 12 from the 3'-end of the oligonucleotide.

The location of a non-complementary nucleobase may be at the 5' end or 3' end of the compound. Alternatively, the non-complementary nucleobase or nucleobases may be at an internal position of the compound. When two or more non-complementary nucleobases are present, they may be contiguous (i.e. linked) or non-contiguous. In one embodiment, a non-complementary nucleobase is located in the wing segment of a gapmer oligonucleotide.

In certain embodiments, compounds described herein that are, or are up to 11, 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as a DYRK1B nucleic acid, or specified portion thereof.

In certain embodiments, compounds described herein that are, or are up to 11, 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as a DYRK1B nucleic acid, or specified portion thereof.

In certain embodiments, compounds described herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of a compound. In certain embodiments, the compounds are complementary to at least an 8 nucleobase portion of a target segment. In certain embodiments, the compounds are complementary to at least a 9 nucleobase portion of a target segment. In certain embodiments, the compounds are complementary to at least a 10 nucleobase portion of a target segment. In certain embodiments, the compounds are complementary to at least an 11 nucleobase portion of a target segment. In certain embodiments, the compounds are complementary to at least a 12 nucleobase portion of a target segment. In certain embodiments, the compounds are complementary to at least a 13 nucleobase portion of a target segment. In certain embodiments, the compounds are complementary to at least a 14 nucleobase portion of a target segment. In certain embodiments, the compounds are complementary to at least a 15 nucleobase portion of a target segment. In certain embodiments, the compounds are complementary to at least a 16 nucleobase portion of a target segment. Also contemplated are compounds that are complementary to at least a 9, 10, 11, 12, 13, 14, 15, 16, 17, 18, 19, 20, or more nucleobase portion of a target segment, or a range defined by any two of these values.

Identity

The compounds provided herein may also have a defined percent identity to a particular nucleotide sequence, SEQ ID NO, or compound represented by a specific Isis number, or portion thereof. In certain embodiments, compounds described herein are antisense compounds or oligomeric compounds. In certain embodiments, compounds described herein are modified oligonucleotides. As used herein, a compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the compounds described herein as well as compounds having non-identical bases relative to the compounds provided herein also are contemplated. The non-identical bases may be adjacent to each other or dispersed throughout the compound. Percent identity of a compound is calculated according to the number of bases that have identical base pairing relative to the sequence to which it is being compared.

In certain embodiments, compounds described herein, or portions thereof, are, or are at least, 70%, 75%, 80%, 85%, 90%, 91%, 92%, 93%, 94%, 95%, 96%, 97%, 98%, 99% or 100% identical to one or more of the compounds or SEQ ID NOs, or a portion thereof, disclosed herein. In certain embodiments, compounds described herein are about 70%, 75%, 80%, 85%, 90%, 91%, 92%, 93%, 94%, 95%, 96%, 97%, 98%, or 99% identical, or any percentage between such values, to a particular nucleotide sequence, SEQ ID NO, or compound represented by a specific Isis number, or portion thereof, in which the compounds comprise an oligonucleotide having one or more mismatched nucleobases. In certain such embodiments, the mismatch is at position 1, 2, 3, 4, 5, 6, 7, 8, 9, 10, 11, or 12 from the 5'-end of the oligonucleotide. In certain such embodiments, the mismatch is at position 2, 3, 4, 5, 6, 7, 8, 9, 10, 11, or 12 from the 3'-end of the oligonucleotide.

In certain embodiments, compounds described herein are antisense compounds. In certain embodiments, a portion of the compound is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

In certain embodiments, compounds described herein are oligonucleotides. In certain embodiments, a portion of the oligonucleotide is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

Certain Modified Compounds

In certain embodiments, compounds described herein comprise or consist of oligonucleotides consisting of linked nucleosides. Oligonucleotides may be unmodified oligonucleotides (RNA or DNA) or may be modified oligonucleotides. Modified oligonucleotides comprise at least one modification relative to unmodified RNA or DNA (i.e., comprise at least one modified nucleoside (comprising a modified sugar moiety and/or a modified nucleobase) and/or at least one modified internucleoside linkage).

A. Modified Nucleosides

Modified nucleosides comprise a modified sugar moiety or a modified nucleobase or both a modifed sugar moiety and a modified nucleobase.

1. Modified Sugar Moieties

In certain embodiments, sugar moieties are non-bicyclic modified sugar moieties. In certain embodiments, modified sugar moieties are bicyclic or tricyclic sugar moieties. In certain embodiments, modified sugar moieties are sugar surrogates. Such sugar surrogates may comprise one or more substitutions corresponding to those of other types of modified sugar moieties.

In certain embodiments, modified sugar moieties are non-bicyclic modified sugar moieties comprising a furanosyl ring with one or more acyclic substituent, including but not limited to substituents at the 2', 4', and/or 5' positions. In certain embodiments one or more acyclic substituent of non-bicyclic modified sugar moieties is branched. Examples of 2'-substituent groups suitable for non-bicyclic modified sugar moieties include but are not limited to: 2'-F, 2'-OCH$_3$ ("OMe" or "O-methyl"), and 2'-O(CH$_2$)$_2$OCH$_3$ ("MOE"). In certain embodiments, 2'-substituent groups are selected from among: halo, allyl, amino, azido, SH, CN, OCN, $CF_3$, $OCF_3$, alkoxy, O—$C_1$-$C_{10}$ substituted alkoxy, O—$C_1$-$C_{10}$ alkyl, O—$C_1$-$C_{10}$ substituted alkyl, S-alkyl, N($R_m$)-alkyl, O-alkenyl, S-alkenyl, N($R_m$)-alkenyl, O-alkynyl, S-alkynyl, N($R_m$)-alkynyl, O-alkylenyl-O-alkyl, alkynyl, alkaryl, aralkyl, O-alkaryl, O-aralkyl, $O(CH_2)_2SCH_3$, $O(CH_2)_2ON(R_m)(R_n)$ or $OCH_2C(=O)$—N($R_m$)($R_n$), where each $R_m$ and $R_n$ is, independently, H, an amino protecting group, or substituted or unsubstituted $C_1$-$C_{10}$ alkyl, and the 2'-substituent groups described in Cook et al., U.S. Pat. No. 6,531,584; Cook et al., U.S. Pat. No. 5,859,221; and Cook et al., U.S. Pat. No. 6,005,087. Certain embodiments of these 2'-substituent groups can be further substituted with one or more substituent groups independently selected from among: hydroxyl, amino, alkoxy, carboxy, benzyl, phenyl, nitro ($NO_2$), thiol, thioalkoxy, thioalkyl, halogen, alkyl, aryl, alkenyl and alkynyl. Examples of 4'-substituent groups suitable for linearlynon-bicyclic modified sugar moieties include but are not limited to alkoxy (e.g., methoxy), alkyl, and those described in Manoharan et al., WO 2015/106128. Examples of 5'-substituent groups suitable for non-bicyclic modified sugar moieties include but are not limited to: 5'-methyl (R or S), 5'-vinyl, and 5'-methoxy. In certain embodiments, non-bicyclic modified sugars comprise more than one non-bridging sugar substituent, for example, 2'-F-5'-methyl sugar moieties and the modified sugar moieties and modified nucleosides described in Migawa et al., WO 2008/101157 and Rajeev et al., US2013/0203836.

In certain embodiments, a 2'-substituted nucleoside or 2'-non-bicyclic modified nucleoside comprises a sugar moiety comprising a linear 2'-substituent group selected from: F, $NH_2$, $N_3$, $OCF_3$, $OCH_3$, $O(CH_2)_3NH_2$, $CH_2CH=CH_2$, $OCH_2CH=CH_2$, $OCH_2CH_2OCH_3$, $O(CH_2)_2SCH_3$, $O(CH_2)_2ON(R_m)(R_n)$, $O(CH_2)_2O(CH_2)_2N(CH_3)_2$, and N-substituted acetamide ($OCH_2C(=O)$—N($R_m$)($R_n$)), where each $R_m$ and $R_n$ is, independently, H, an amino protecting group, or substituted or unsubstituted $C_1$-$C_{10}$ alkyl.

In certain embodiments, a 2'-substituted nucleoside or 2'-non-bicyclic modified nucleoside comprises a sugar moiety comprising a linear 2'-substituent group selected from: F, $OCF_3$, $OCH_3$, $OCH_2CH_2OCH_3$, $O(CH_2)_2SCH_3$, $O(CH_2)_2ON(CH_3)_2$, $O(CH_2)_2O(CH_2)_2N(CH_3)_2$, and $OCH_2C(=O)$—N(H)$CH_3$ ("NMA").

In certain embodiments, a 2'-substituted nucleoside or 2'-non-bicyclic modified nucleoside comprises a sugar moiety comprising a linear 2'-substituent group selected from: F, $OCH_3$, and $OCH_2CH_2OCH_3$.

Nucleosides comprising modified sugar moieties, such as non-bicyclic modified sugar moieties, are referred to by the position(s) of the substitution(s) on the sugar moiety of the nucleoside. For example, nucleosides comprising 2'-substituted or 2-modified sugar moieties are referred to as 2'-substituted nucleosides or 2-modified nucleosides.

Certain modifed sugar moieties comprise a bridging sugar substituent that forms a second ring resulting in a bicyclic sugar moiety. In certain such embodiments, the bicyclic sugar moiety comprises a bridge between the 4' and the 2' furanose ring atoms. Examples of such 4' to 2' bridging sugar substituents include but are not limited to: 4'-$CH_2$-2', 4'-$(CH_2)_2$-2', 4'-$(CH_2)_3$-2', 4'-$CH_2$—O-2' ("LNA"), 4'-$CH_2$—S-2', 4'-$(CH_2)_2$—O-2' ("ENA"), 4'-$CH(CH_3)$—O-2' (referred to as "constrained ethyl" or "cEt" when in the S configuration), 4'-$CH_2$—O—$CH_2$-2', 4'-$CH_2$—N(R)-2', 4'-$CH(CH_2OCH_3)$—O-2' ("constrained MOE" or "cMOE") and analogs thereof (see, e.g., Seth et al., U.S. Pat. No. 7,399,845, Bhat et al., U.S. Pat. No. 7,569,686, Swayze et al., U.S. Pat. No. 7,741,457, and Swayze et al., U.S. Pat. No. 8,022,193), 4'-C($CH_3$)($CH_3$)—O-2' and analogs thereof (see, e.g., Seth et al., U.S. Pat. No. 8,278,283), 4'-$CH_2$—N($OCH_3$)-2' and analogs thereof (see, e.g., Prakash et al., U.S. Pat. No. 8,278,425), 4'-$CH_2$—O—N($CH_3$)-2' (see, e.g., Allerson et al., U.S. Pat. No. 7,696,345 and Allerson et al., U.S. Pat. No. 8,124,745), 4'-$CH_2$—C(H)($CH_3$)-2' (see, e.g., Zhou, et al., J. Org. Chem., 2009, 74, 118-134), 4'-$CH_2$—C($=CH_2$)-2' and analogs thereof (see e.g., Seth et al., U.S. Pat. No. 8,278,426), 4'-C($R_aR_b$)—N(R)—O-2', 4'-C($R_aR_b$)—O—N(R)-2', 4'-$CH_2$—O—N(R)-2', and 4'-$CH_2$—N(R)—O-2', wherein each R, $R_a$, and $R_b$ is, independently, H, a protecting group, or $C_1$-$C_{12}$ alkyl (see, e.g. Imanishi et al., U.S. Pat. No. 7,427,672).

In certain embodiments, such 4' to 2' bridges independently comprise from 1 to 4 linked groups independently selected from: —[C($R_a$)($R_b$)]$_n$—, —[C($R_a$)($R_b$)]$_n$—O—, —C($R_a$)=C($R_b$)—, —C($R_a$)=N—, —C($=NR_a$)—, —C($=O$)—, —C($=S$)—, —O—, —Si($R_a$)$_2$—, —S($=O$)$_x$—, and —N($R_a$)—;

wherein:

x is 0, 1, or 2;

n is 1, 2, 3, or 4;

each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C($=O$)—H), substituted acyl, CN, sulfonyl (S($=O$)$_2$-$J_1$), or sulfoxyl (S($=O$)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C($=O$)—H), substituted acyl, a heterocycle radical, a substituted heterocycle radical, $C_1$-$C_{12}$ aminoalkyl, substituted $C_1$-$C_{12}$ aminoalkyl, or a protecting group.

Additional bicyclic sugar moieties are known in the art, see, for example: Freier et al., *Nucleic Acids Research*, 1997, 25(22), 4429-4443, Albaek et al., *J. Org. Chem.*, 2006, 71, 7731-7740, Singh et al., *Chem. Commun.*, 1998, 4, 455-456; Koshkin et al., *Tetrahedron*, 1998, 54, 3607-3630; Wahlestedt et al., *Proc. Natl. Acad. Sci. U S. A.*, 2000, 97, 5633-5638; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 20017, 129, 8362-8379; Elayadi et al., *Curr. Opinion Invens. Drugs*, 2001, 2, 558-561; Braasch et al., *Chem. Biol.*, 2001, 8, 1-7; Orum et al., *Curr. Opinion Mol. Ther.*, 2001, 3, 239-243; Wengel et al., U.S. Pat. No. 7,053,207, Imanishi et al., U.S. Pat. No. 6,268,490, Imanishi et al. U.S. Pat. No. 6,770,748, Imanishi et al., U.S. RE44,779; Wengel et al., U.S. Pat. No. 6,794,499, Wengel et al., U.S. Pat. No. 6,670,461; Wengel et al., U.S. Pat. No. 7,034,133, Wengel et al., U.S. Pat. No. 8,080,644; Wengel et al., U.S. Pat. No. 8,034,909; Wengel et al., U.S. Pat. No. 8,153,365; Wengel et al., U.S. Pat. No. 7,572,582; and Ramasamy et al., U.S. Pat. No. 6,525,191, Torsten et al., WO 2004/106356, Wengel et al., WO 91999/014226; Seth et al., WO 2007/134181; Seth et al., U.S. Pat. No. 7,547,684; Seth et al., U.S. Pat. No. 7,666,854; Seth et al., U.S. Pat. No. 8,088,746; Seth et al., U.S. Pat. No. 7,750,131; Seth et al., U.S. Pat. No. 8,030,467; Seth et al., U.S. Pat. No. 8,268,980; Seth et al., U.S. Pat. No. 8,546,556; Seth et al., U.S. Pat. No. 8,530,640; Migawa et al., U.S. Pat.

No. 9,012,421; Seth et al., U.S. Pat. No. 8,501,805; and U.S. Patent Publication Nos. Allerson et al., US2008/0039618 and Migawa et al., US2015/0191727.

In certain embodiments, bicyclic sugar moieties and nucleosides incorporating such bicyclic sugar moieties are further defined by isomeric configuration. For example, an LNA nucleoside (described herein) may be in the α-L configuration or in the β-D configuration.

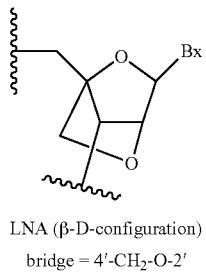

LNA (β-D-configuration)
bridge = 4'-CH$_2$-O-2'

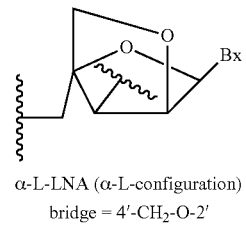

α-L-LNA (α-L-configuration)
bridge = 4'-CH$_2$-O-2'

α-L-methyleneoxy (4'-CH$_2$—O-2') or α-L-LNA bicyclic nucleosides have been incorporated into oligonucleotides that showed antisense activity (Frieden et al., *Nucleic Acids Research*, 2003, 21, 6365-6372). Herein, general descriptions of bicyclic nucleosides include both isomeric configurations. When the positions of specific bicyclic nucleosides (e.g., LNA or cEt) are identified in exemplified embodiments herein, they are in the β-D configuration, unless otherwise specified.

In certain embodiments, modified sugar moieties comprise one or more non-bridging sugar substituent and one or more bridging sugar substituent (e.g., 5'-substituted and 4'-2' bridged sugars).

In certain embodiments, modified sugar moieties are sugar surrogates. In certain such embodiments, the oxygen atom of the sugar moiety is replaced, e.g., with a sulfur, carbon or nitrogen atom. In certain such embodiments, such modified sugar moieties also comprise bridging and/or non-bridging substituents as described herein. For example, certain sugar surrogates comprise a 4'-sulfur atom and a substitution at the 2'-position (see, e.g., Bhat et al., U.S. Pat. No. 7,875,733 and Bhat et al., U.S. Pat. No. 7,939,677) and/or the 5' position.

In certain embodiments, sugar surrogates comprise rings having other than 5 atoms. For example, in certain embodiments, a sugar surrogate comprises a six-membered tetrahydropyran ("THP"). Such tetrahydropyrans may be further modified or substituted. Nucleosides comprising such modified tetrahydropyrans include but are not limited to hexitol nucleic acid ("HNA"), anitol nucleic acid ("ANA"), manitol nucleic acid ("MNA") (see e.g., Leumann, C J. *Bioorg. & Med. Chem.* 2002, 10, 841-854), fluoro HNA:

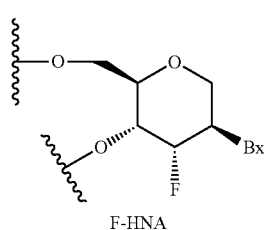

F-HNA ("F-HNA", see e.g., Swayze et al., U.S. Pat. No. 8,088,904; Swayze et al., U.S. Pat. No. 8,440,803; Swayze et al., U.S.; and Swayze et al., U.S. Pat. No. 9,005,906, F-HNA can also be referred to as a F-THP or 3'-fluoro tetrahydropyran), and nucleosides comprising additional modified THP compounds having the formula:

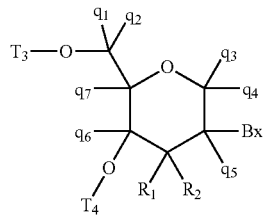

wherein, independently, for each of said modified THP nucleoside: Bx is a nucleobase moiety; $T_3$ and $T_4$ are each, independently, an internucleoside linking group linking the modified THP nucleoside to the remainder of an oligonucleotide or one of $T_3$ and $T_4$ is an internucleoside linking group linking the modified THP nucleoside to the remainder of an oligonucleotide and the other of $T_3$ and $T_4$ is H, a hydroxyl protecting group, a linked conjugate group, or a 5' or 3'-terminal group; $q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and each of $R_1$ and $R_2$ is independently selected from among: hydrogen, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$, and CN, wherein X is O, S or $NJ_1$, and each $J_1$, $J_2$, and $J_3$ is, independently, H or $C_1$-$C_6$ alkyl.

In certain embodiments, modified THP nucleosides are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, modified THP nucleosides are provided wherein one of $R_1$ and $R_2$ is F. In certain embodiments, $R_1$ is F and $R_2$ is H, in certain embodiments, $R_1$ is methoxy and $R_2$ is H, and in certain embodiments, $R_1$ is methoxyethoxy and $R_2$ is H.

In certain embodiments, sugar surrogates comprise rings having more than 5 atoms and more than one heteroatom. For example, nucleosides comprising morpholino sugar moieties and their use in oligonucleotides have been reported (see, e.g., Braasch et al., Biochemistry, 2002, 41, 4503-4510 and Summerton et al., U.S. Pat. No. 5,698,685; Summerton et al., U.S. Pat. No. 5,166,315; Summerton et al., U.S. Pat. No. 5,185,444; and Summerton et al., U.S. Pat. No. 5,034,506). As used here, the term "morpholino" means a sugar surrogate having the following structure:

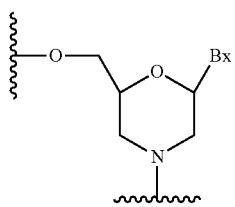

In certain embodiments, morpholinos may be modified, for example by adding or altering various substituent groups from the above morpholino structure. Such sugar surrogates are referred to herein as "modifed morpholinos."

In certain embodiments, sugar surrogates comprise acyclic moieites. Examples of nucleosides and oligonucleotides comprising such acyclic sugar surrogates include but are not limited to: peptide nucleic acid ("PNA"), acyclic butyl nucleic acid (see, e.g., Kumar et al., Org. Biomol. Chem., 2013, 11, 5853-5865), and nucleosides and oligonucleotides described in Manoharan et al., WO2011/133876.

Many other bicyclic and tricyclic sugar and sugar surrogate ring systems are known in the art that can be used in modified nucleosides.

2. Modified Nucleobases

Nucleobase (or base) modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications can impart nuclease stability, binding affinity or some other beneficial biological property to compounds described herein.

In certain embodiments, compounds described herein comprise modified oligonucleotides. In certain embodiments, modified oligonucleotides comprise one or more nucleoside comprising an unmodified nucleobase. In certain embodiments, modified oligonucleotides comprise one or more nucleoside comprising a modified nucleobase. In certain embodiments, modified oligonucleotides comprise one or more nucleoside that does not comprise a nucleobase, referred to as an abasic nucleoside.

In certain embodiments, modified nucleobases are selected from: 5-substituted pyrimidines, 6-azapyrimi¬dines, alkyl or alkynyl substituted pyrimidines, alkyl substituted purines, and N-2, N-6 and O-6 substituted purines. In certain embodiments, modified nucleobases are selected from: 2-aminopropyladenine, 5-hydroxymethyl cytosine, 5-methylcytosine, xanthine, hypoxanthine, 2-aminoadenine, 6-N-methylguanine, 6-N-methyladenine, 2-propyladenine, 2-thiouracil, 2-thiothymine and 2-thiocytosine, 5-propynyl (C≡C—CH3) uracil, 5-propynylcytosine, 6-azouracil, 6-azocytosine, 6-azothymine, 5-ribosyluracil (pseudouracil), 4-thiouracil, 8-halo, 8-amino, 8-thiol, 8-thioalkyl, 8-hydroxyl, 8-aza and other 8-substituted purines, 5-halo, particularly 5-bromo, 5-trifluoromethyl, 5-halouracil, and 5-halocytosine, 7-methylguanine, 7-methyladenine, 2-F-adenine, 2-aminoadenine, 7-deazaguanine, 7-deazaadenine, 3-deazaguanine, 3-deazaadenine, 6-N-benzoyladenine, 2-N-isobutyrylguanine, 4-N-benzoylcytosine, 4-N-benzoyluracil, 5-methyl 4-N-benzoylcytosine, 5-methyl 4-N-benzoyluracil, universal bases, hydrophobic bases, promiscuous bases, size-expanded bases, and fluorinated bases. Further modified nucleobases include tricyclic pyrimidines, such as 1,3-diazaphenoxazine-2-one, 1,3-diazaphenothiazine-2-one and 9-(2-aminoethoxy)-1,3-diazaphenoxazine-2-one (G-clamp). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in Merigan et al., U.S. Pat. No. 3,687,808, those disclosed in The Concise Encyclopedia Of Polymer Science And Engineering, Kroschwitz, J. I., Ed., John Wiley & Sons, 1990, 858-859; Englisch et al., Angewandte Chemie, International Edition, 1991, 30, 613; Sanghvi, Y. S., Chapter 15, Antisense Research and Applications, Crooke, S. T. and Lebleu, B., Eds., CRC Press, 1993, 273-288; and those disclosed in Chapters 6 and 15, Antisense Drug Technology, Crooke S. T., Ed., CRC Press, 2008, 163-166 and 442-443.

Publications that teach the preparation of certain of the above noted modified nucleobases as well as other modified nucleobases include without limitation, Manoharan et al., US2003/0158403, Manoharan et al., US2003/0175906; Dinh et al., U.S. Pat. No. 4,845,205; Spielvogel et al., U.S. Pat. No. 5,130,302; Rogers et al., U.S. Pat. No. 5,134,066; Bischofberger et al., U.S. Pat. No. 5,175,273; Urdea et al., U.S. Pat. No. 5,367,066; Benner et al., U.S. Pat. No. 5,432,272; Matteucci et al., U.S. Pat. No. 5,434,257; Gmeiner et al., U.S. Pat. No. 5,457,187; Cook et al., U.S. Pat. No. 5,459,255; Froehler et al., U.S. Pat. No. 5,484,908; Matteucci et al., U.S. Pat. No. 5,502,177; Hawkins et al., U.S. Pat. No. 5,525,711; Haralambidis et al., U.S. Pat. No. 5,552,540; Cook et al., U.S. Pat. No. 5,587,469; Froehler et al., U.S. Pat. No. 5,594,121; Switzer et al., U.S. Pat. No. 5,596,091; Cook et al., U.S. Pat. No. 5,614,617; Froehler et al., U.S. Pat. No. 5,645,985; Cook et al., U.S. Pat. No. 5,681,941; Cook et al., U.S. Pat. No. 5,811,534; Cook et al., U.S. Pat. No. 5,750,692; Cook et al., U.S. Pat. No. 5,948,903; Cook et al., U.S. Pat. No. 5,587,470; Cook et al., U.S. Pat. No. 5,457,191; Matteucci et al., U.S. Pat. No. 5,763,588; Froehler et al., U.S. Pat. No. 5,830,653; Cook et al., U.S. Pat. No. 5,808,027; Cook et al., U.S. Pat. No. 6,166,199; and Matteucci et al., U.S. Pat. No. 6,005,096.

In certain embodiments, compounds targeted to a DYRK1B nucleic acid comprise one or more modified nucleobases. In certain embodiments, the modified nucleobase is 5-methylcytosine. In certain embodiments, each cytosine is a 5-methylcytosine.

Modified Internucleoside Linkages

The naturally occurring internucleoside linkage of RNA and DNA is a 3' to 5' phosphodiester linkage. In certain embodiments, compounds described herein having one or more modified, i.e. non-naturally occurring, internucleoside linkages are often selected over compounds having naturally occurring internucleoside linkages because of desirable properties such as, for example, enhanced cellular uptake, enhanced affinity for target nucleic acids, and increased stability in the presence of nucleases.

In certain embodiments, compounds targeted to a DYRK1B nucleic acid comprise one or more modified internucleoside linkages. In certain embodiments, the modified internucleoside linkages are phosphorothioate linkages. In certain embodiments, each internucleoside linkage of the compound is a phosphorothioate internucleoside linkage.

In certain embodiments, compounds described herein comprise oligonucleotides. Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, nucleosides of modified oligonucleotides may be linked together using any internucleoside linkage. The two main classes of internucleoside linking groups are defined by the presence or absence of a phosphorus atom. Representative phosphorus-containing internucleoside linkages include but are not limited to phosphates, which contain a phosphodiester bond ("P=O") (also referred to as unmodified or naturally occurring linkages), phosphotriesters, methylphosphonates, phosphoramidates, and phosphorothioates ("P=S"), and phosphorodithioates ("HS—P=S"). Representative non-phosphorus containing internucleoside linking groups include but are not limited to methylenemethylimino (—CH2-N(CH3)-O—CH2-), thiodiester, thionocarbamate (—O—C(=O)(NH)—S—); siloxane (—O—SiH2-O—); and N,N'-dimethylhydrazine (—CH2-N(CH3)-N(CH3)-). Modified internucleoside linkages, compared to naturally occurring phosphate linkages, can be used to alter, typically increase, nuclease resistance of the oligonucleotide. In certain embodiments, internucleoside linkages having a chiral atom can be prepared as a racemic mixture, or as separate enantiomers. Representative chiral internucleoside linkages include but are not limited to alkylphosphonates and phosphorothioates. Methods of preparation of phosphorous-containing and non-phosphorous-containing internucleoside linkages are well known to those skilled in the art.

Neutral internucleoside linkages include, without limitation, phosphotriesters, methylphosphonates, MMI (3'-CH2-N(CH3)-O-5'), amide-3 (3'-CH2-C(=O)—N(H)-5'), amide-4 (3'-CH2-N(H)—C(=O)-5'), formacetal (3'-O—CH2-O-5'), methoxypropyl, and thioformacetal (3'-S-CH2-O-5'). Further neutral internucleoside linkages include nonionic linkages comprising siloxane (dialkylsiloxane), carboxylate ester, carboxamide, sulfide, sulfonate ester and amides (See for example: Carbohydrate Modifications in Antisense Research; Y. S. Sanghvi and P. D. Cook, Eds., ACS Symposium Series 580; Chapters 3 and 4, 40-65). Further neutral internucleoside linkages include nonionic linkages comprising mixed N, O, S and CH2 component parts.

In certain embodiments, oligonucleotides comprise modified internucleoside linkages arranged along the oligonucleotide or region thereof in a defined pattern or modified internucleoside linkage motif. In certain embodiments, internucleoside linkages are arranged in a gapped motif. In such embodiments, the internucleoside linkages in each of two wing regions are different from the internucleoside linkages in the gap region. In certain embodiments the internucleoside linkages in the wings are phosphodiester and the internucleoside linkages in the gap are phosphorothioate. The nucleoside motif is independently selected, so such oligonucleotides having a gapped internucleoside linkage motif may or may not have a gapped nucleoside motif and if it does have a gapped nucleoside motif, the wing and gap lengths may or may not be the same.

In certain embodiments, oligonucleotides comprise a region having an alternating internucleoside linkage motif. In certain embodiments, oligonucleotides of the present invention comprise a region of uniformly modified internucleoside linkages. In certain such embodiments, the oligonucleotide comprises a region that is uniformly linked by phosphorothioate internucleoside linkages. In certain embodiments, the oligonucleotide is uniformly linked by phosphorothioate. In certain embodiments, each internucleoside linkage of the oligonucleotide is selected from phosphodiester and phosphorothioate. In certain embodiments, each internucleoside linkage of the oligonucleotide is selected from phosphodiester and phosphorothioate and at least one internucleoside linkage is phosphorothioate.

In certain embodiments, the oligonucleotide comprises at least 6 phosphorothioate internucleoside linkages. In certain embodiments, the oligonucleotide comprises at least 8 phosphorothioate internucleoside linkages. In certain embodiments, the oligonucleotide comprises at least 10 phosphorothioate internucleoside linkages. In certain embodiments, the oligonucleotide comprises at least one block of at least 6 consecutive phosphorothioate internucleoside linkages. In certain embodiments, the oligonucleotide comprises at least one block of at least 8 consecutive phosphorothioate internucleoside linkages. In certain embodiments, the oligonucleotide comprises at least one block of at least 10 consecutive phosphorothioate internucleoside linkages. In certain embodiments, the oligonucleotide comprises at least block of at least one 12 consecutive phosphorothioate internucleoside linkages. In certain such embodiments, at least one such block is located at the 3' end of the oligonucleotide. In certain such embodiments, at least one such block is located within 3 nucleosides of the 3' end of the oligonucleotide.

In certain embodiments, oligonucleotides comprise one or more methylphosphonate linkages. In certain embodiments, oligonucleotides having a gapmer nucleoside motif comprise a linkage motif comprising all phosphorothioate linkages except for one or two methylphosponate linkages. In certain embodiments, one methylphosphonate linkage is in the central gap of an oligonucleotide having a gapmer nucleoside motif.

In certain embodiments, it is desirable to arrange the number of phosphorothioate internucleoside linkages and phosphodiester internucleoside linkages to maintain nuclease resistance. In certain embodiments, it is desirable to arrange the number and position of phosphorothioate internucleoside linkages and the number and position of phosphodiester internucleoside linkages to maintain nuclease resistance. In certain embodiments, the number of phosphorothioate internucleoside linkages may be decreased and the number of phosphodiester internucleoside linkages may be increased. In certain embodiments, the number of phosphorothioate internucleoside linkages may be decreased and the number of phosphodiester internucleoside linkages may be increased while still maintaining nuclease resistance. In certain embodiments it is desirable to decrease the number of phosphorothioate internucleoside linkages while retaining nuclease resistance. In certain embodiments it is desirable to increase the number of phosphodiester internucleoside linkages while retaining nuclease resistance.

B. Certain Motifs

In certain embodiments, compounds described herein comprise oligonucleotides. Oligonucleotides can have a motif, e.g. a pattern of unmodified and/or modified sugar moieties, nucleobases, and/or internucleoside linkages. In certain embodiments, modified oligonucleotides comprise one or more modified nucleoside comprising a modified sugar. In certain embodiments, modified oligonucleotides comprise one or more modified nucleosides comprising a modified nucleobase. In certain embodiments, modified oligonucleotides comprise one or more modified internucleoside linkage. In such embodiments, the modified, unmodified, and differently modified sugar moieties, nucleobases, and/or internucleoside linkages of a modified oligonucleotide define a pattern or motif. In certain embodiments, the patterns of sugar moieties, nucleobases, and internucleoside linkages are each independent of one another. Thus, a modified oligonucleotide may be described by its sugar motif, nucleobase motif and/or internucleoside linkage motif (as used herein, nucleobase motif describes the modifications to the nucleobases independent of the sequence of nucleobases).

1. Certain Sugar Motifs

In certain embodiments, compounds described herein comprise oligonucleotides. In certain embodiments, oligonucleotides comprise one or more type of modified sugar and/or unmodified sugar moiety arranged along the oligonucleotide or region thereof in a defined pattern or sugar motif. In certain instances, such sugar motifs include but are not limited to any of the sugar modifications discussed herein.

In certain embodiments, modified oligonucleotides comprise or consist of a region having a gapmer motif, which comprises two external regions or "wings" and a central or internal region or "gap." The three regions of a gapmer motif (the 5'-wing, the gap, and the 3'-wing) form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap (i.e., the wing/gap junction). In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar motifs of the two wings are the same as one another (symmetric gapmer). In certain embodiments, the sugar motif of the 5'-wing differs from the sugar motif of the 3'-wing (asymmetric gapmer).

In certain embodiments, the wings of a gapmer comprise 1-5 nucleosides. In certain embodiments, the wings of a gapmer comprise 2-5 nucleosides. In certain embodiments, the wings of a gapmer comprise 3-5 nucleosides. In certain embodiments, the nucleosides of a gapmer are all modified nucleosides.

In certain embodiments, the gap of a gapmer comprises 7-12 nucleosides. In certain embodiments, the gap of a gapmer comprises 7-10 nucleosides. In certain embodiments, the gap of a gapmer comprises 8-10 nucleosides. In certain embodiments, the gap of a gapmer comprises 10 nucleosides. In certain embodiment, each nucleoside of the gap of a gapmer is an unmodified 2'-deoxy nucleoside.

In certain embodiments, the gapmer is a deoxy gapmer. In such embodiments, the nucleosides on the gap side of each wing/gap junction are unmodified 2'-deoxy nucleosides and the nucleosides on the wing sides of each wing/gap junction are modified nucleosides. In certain such embodiments, each nucleoside of the gap is an unmodified 2'-deoxy nucleoside. In certain such embodiments, each nucleoside of each wing is a modified nucleoside.

In certain embodiments, a modified oligonucleotide has a fully modified sugar motif wherein each nucleoside of the modified oligonucleotide comprises a modified sugar moiety. In certain embodiments, modified oligonucleotides comprise or consist of a region having a fully modified sugar motif wherein each nucleoside of the region comprises a modified sugar moiety. In certain embodiments, modified oligonucleotides comprise or consist of a region having a fully modified sugar motif, wherein each nucleoside within the fully modified region comprises the same modified sugar moiety, referred to herein as a uniformly modified sugar motif. In certain embodiments, a fully modified oligonucleotide is a uniformly modified oligonucleotide. In certain embodiments, each nucleoside of a uniformly modified comprises the same 2'-modification.

2. Certain Nucleobase Motifs

In certain embodiments, compounds described herein comprise oligonucleotides. In certain embodiments, oligonucleotides comprise modified and/or unmodified nucleobases arranged along the oligonucleotide or region thereof in a defined pattern or motif. In certain embodiments, each nucleobase is modified. In certain embodiments, none of the nucleobases are modified. In certain embodiments, each purine or each pyrimidine is modified. In certain embodiments, each adenine is modified. In certain embodiments, each guanine is modified. In certain embodiments, each thymine is modified. In certain embodiments, each uracil is modified. In certain embodiments, each cytosine is modified. In certain embodiments, some or all of the cytosine nucleobases in a modified oligonucleotide are 5-methylcytosines.

In certain embodiments, modified oligonucleotides comprise a block of modified nucleobases. In certain such embodiments, the block is at the 3'-end of the oligonucleotide. In certain embodiments the block is within 3 nucleosides of the 3'-end of the oligonucleotide. In certain embodiments, the block is at the 5'-end of the oligonucleotide. In certain embodiments the block is within 3 nucleosides of the 5'-end of the oligonucleotide.

In certain embodiments, oligonucleotides having a gapmer motif comprise a nucleoside comprising a modified nucleobase. In certain such embodiments, one nucleoside comprising a modified nucleobase is in the central gap of an oligonucleotide having a gapmer motif. In certain such embodiments, the sugar moiety of said nucleoside is a 2'-deoxyribosyl moiety. In certain embodiments, the modified nucleobase is selected from: a 2-thiopyrimidine and a 5-propynepyrimidine.

3. Certain Internucleoside Linkage Motifs

In certain embodiments, compounds described herein comprise oligonucleotides. In certain embodiments, oligonucleotides comprise modified and/or unmodified internucleoside linkages arranged along the oligonucleotide or region thereof in a defined pattern or motif. In certain embodiments, essentially each internucleoside linking group is a phosphate internucleoside linkage (P=O). In certain embodiments, each internucleoside linking group of a modified oligonucleotide is a phosphorothioate (P=S). In certain embodiments, each internucleoside linking group of a modified oligonucleotide is independently selected from a phosphorothioate and phosphate internucleoside linkage. In certain embodiments, the sugar motif of a modified oligonucleotide is a gapmer and the internucleoside linkages within the gap are all modified. In certain such embodiments, some or all of the internucleoside linkages in the wings are unmodified phosphate linkages. In certain embodiments, the terminal internucleoside linkages are modified.

C. Certain Modified Oligonucleotides

In certain embodiments, compounds described herein comprise modified oligonucleotides. In certain embodiments, the above modifications (sugar, nucleobase, internucleoside linkage) are incorporated into a modified oligonucleotide. In certain embodiments, modified oligonucleotides are characterized by their modification, motifs, and overall lengths. In certain embodiments, such parameters are each independent of one another. Thus, unless otherwise indicated, each internucleoside linkage of an oligonucleotide having a gapmer sugar motif may be modified or unmodified and may or may not follow the gapmer modification pattern of the sugar modifications. For example, the internucleoside linkages within the wing regions of a sugar gapmer may be the same or different from one another and may be the same or different from the internucleoside linkages of the gap region of the sugar motif. Likewise, such gapmer oligonucleotides may comprise one or more modified nucleobase independent of the gapmer pattern of the sugar modifications. Furthermore, in certain instances, an oligonucleotide is described by an overall length or range and by lengths or length ranges of two or more regions (e.g., a regions of nucleosides having specified sugar modifications), in such circumstances it may be possible to select numbers for each range that result in an oligonucleotide having an overall length falling outside the specified range. In such circumstances, both elements must be satisfied. For example, in certain embodiments, a modified oligonucleotide consists of 15-20 linked nucleosides and has a sugar motif consisting of three regions, A, B, and C, wherein region A consists of 2-6 linked nucleosides having a specified sugar motif, region B consists of 6-10 linked nucleosides having a specified sugar motif, and region C consists of 2-6 linked nucleosides having a specified sugar motif. Such embodiments do not include modified oligonucleotides where A and C each consist of 6 linked nucleosides and B consists of 10 linked nucleosides (even though those numbers of nucleosides are permitted within the requirements for A, B, and C) because the overall length of such oligonucleotide is 22, which exceeds the upper limit of the overall length of the modified oligonucleotide (20). Herein, if a description of an oligonucleotide is silent with respect to one or more parameter, such parameter is not limited. Thus, a modified oligonucleotide described only as having a gapmer sugar motif without further description may have any length, internucleoside linkage motif, and nucleobase motif. Unless otherwise indicated, all modifications are independent of nucleobase sequence.

Compositions and Methods for Formulating Pharmaceutical Compositions

Compounds described herein may be admixed with pharmaceutically acceptable active or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

In certain embodiments, the present invention provides pharmaceutical compositions comprising one or more compounds or a salt thereof. In certain embodiments, the compounds are antisense compounds or oligomeric compounds. In certain embodiments, the compounds comprise or consist of a modified oligonucleotide. In certain such embodiments, the pharmaceutical composition comprises a suitable pharmaceutically acceptable diluent or carrier. In certain embodiments, a pharmaceutical composition comprises a sterile saline solution and one or more compound. In certain embodiments, such pharmaceutical composition consists of a sterile saline solution and one or more compound. In certain embodiments, the sterile saline is pharmaceutical grade saline. In certain embodiments, a pharmaceutical composition comprises one or more compound and sterile water. In certain embodiments, a pharmaceutical composition consists of one compound and sterile water. In certain embodiments, the sterile water is pharmaceutical grade water. In certain embodiments, a pharmaceutical composition comprises one or more compound and phosphate-buffered saline (PBS). In certain embodiments, a pharmaceutical composition consists of one or more compound and sterile PBS. In certain embodiments, the sterile PBS is pharmaceutical grade PBS. Compositions and methods for the formulation of pharmaceutical compositions are dependent upon a number of criteria, including, but not limited to, route of administration, extent of disease, or dose to be administered.

A compound described herein targeted to a DYRK1B nucleic acid can be utilized in pharmaceutical compositions by combining the compound with a suitable pharmaceutically acceptable diluent or carrier. In certain embodiments, a pharmaceutically acceptable diluent is water, such as sterile water suitable for injection. Accordingly, in one embodiment, employed in the methods described herein is a pharmaceutical composition comprising a compound targeted to a DYRK1B nucleic acid and a pharmaceutically acceptable diluent. In certain embodiments, the pharmaceutically acceptable diluent is water. In certain embodiments, the compound comprises or consists of a modified oligonucleotide provided herein.

Pharmaceutical compositions comprising compounds provided herein encompass any pharmaceutically acceptable salts, esters, or salts of such esters, or any other oligonucleotide which, upon administration to an animal, including a human, is capable of providing (directly or indirectly) the biologically active metabolite or residue thereof. In certain embodiments, the compounds are antisense compounds or oligomeric compounds. In certain embodiments, the compound comprises or consists of a modified oligonucleotide. Accordingly, for example, the disclosure is also drawn to pharmaceutically acceptable salts of compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of a compound which are cleaved by endogenous nucleases within the body, to form the active compound.

In certain embodiments, the compounds or compositions further comprise a pharmaceutically acceptable carrier or diluent.

Certain Combinations and Combination Therapies

In certain embodiments, a first agent comprising the compound described herein is co-administered with one or more secondary agents. In certain embodiments, such second agents are designed to treat the same disease, disorder, or condition as the first agent described herein. In certain embodiments, such second agents are designed to treat a different disease, disorder, or condition as the first agent described herein. In certain embodiments, a first agent is designed to treat an undesired side effect of a second agent. In certain embodiments, second agents are co-administered with the first agent to treat an undesired effect of the first agent. In certain embodiments, such second agents are designed to treat an undesired side effect of one or more pharmaceutical compositions as described herein. In certain embodiments, second agents are co-administered with the first agent to produce a combinational effect. In certain embodiments, second agents are co-administered with the first agent to produce a synergistic effect. In certain embodiments, the co-administration of the first and second agents permits use of lower dosages than would be required to achieve a therapeutic or prophylactic effect if the agents were administered as independent therapy.

In certain embodiments, one or more compounds or compositions provided herein are co-administered with one or more secondary agents. In certain embodiments, the secondary agent is a glucose-lowering agent. In certain embodiments, one or more compounds or compositions provided herein and one or more glucose-lowering agents are administered at different times. In certain embodiments, one or more compounds or compositions provided herein and one or more glucose-lowering agents are prepared together in a single formulation. In certain embodiments, one or more compounds or compositions provided herein and one or more glucose-lowering agents are prepared separately. In certain embodiments, a glucose-lowering agent is selected from a PPAR agonist, a dipeptidyl peptidase (IV) inhibitor, a GLP-I analog, insulin or an insulin analog, an insulin secretagogue, a SGLT2 inhibitor, a human amylin analog, a biguanide, an alpha-glucosidase inhibitor, or a combination thereof. In certain embodiments, a glucose-lowering agent is selected from metformin, sulfonylurea, rosiglitazone, or a combination thereof. In certain embodiments, a glucose-lowering agent is selected from acetohexamide, chlorpropamide, tolbutamide, tolazamide, glimepiride, a glipizide, a glyburide, or a gliclazide. In certain embodiments, a glucose-lowering agent is selected from a meglitinide selected from nateglinide or repaglinide. In certain embodiments, a glucose-lowering agent is selected from a thiazolidinedione selected from pioglitazone or rosiglitazone. In certain embodiments, a glucose-lowering agent is selected from an alpha-glucosidase inhibitor selected from acarbose or miglitol. In certain embodiments, a glucose-lowering agent is selected from insulin or an insulin-analog.

Certain embodiments are directed to the use of a compound targeted to DYRK1B as described herein in combination with a glucose-lowering agent. In particular embodiments such use is in a method of treating a patient suffering from a metabolic disease or disorder or in the preparation or manufacture of a medicament for treating the metabolic disease or disorder. In certain embodiments the metabolic disease or disorder is selected from: diabetes mellitus, hyperglycemia, obesity, metabolic syndrome, essential hypertension, disorders of lipid metabolism, hypertensive heart disease, myocardial infarction, pulmonary heart disease, heart failure, and other symptoms involving the cardiovascular system. In certain embodiments, a glucose-lowering agent is selected from a PPAR agonist, a dipeptidyl peptidase (IV) inhibitor, a GLP-I analog, insulin or an insulin analog, an insulin secretagogue, a SGLT2 inhibitor, a human amylin analog, a biguanide, an alpha-glucosidase inhibitor, or a combination thereof. In certain embodiments, a glucose-lowering agent is selected from metformin, sulfonylurea, rosiglitazone, or a combination thereof. In certain embodiments, a glucose-lowering agent is selected from acetohexamide, chlorpropamide, tolbutamide, tolazamide, glimepiride, a glipizide, a glyburide, or a gliclazide. In certain embodiments, a glucose-lowering agent is selected from a meglitinide selected from nateglinide or repaglinide. In certain embodiments, a glucose-lowering agent is selected from a thiazolidinedione selected from pioglitazone or rosiglitazone. In certain embodiments, a glucose-lowering agent is selected from an alpha-glucosidase inhibitor selected from acarbose or miglitol. In certain embodiments, a glucose-lowering agent is selected from insulin or an insulin-analog.

Certain embodiments are drawn to a combination of a compound targeted to DYRK1B as described herein and a glucose-lowering agent, such as a glucose-lowering agent is selected from: a PPAR agonist, a dipeptidyl peptidase (IV) inhibitor, a GLP-I analog, insulin or an insulin analog, an insulin secretagogue, a SGLT2 inhibitor, a human amylin analog, a biguanide, an alpha-glucosidase inhibitor, metformin, sulfonylurea, rosiglitazone, acetohexamide, chlorpropamide, tolbutamide, tolazamide, glimepiride, a glipizide, a glyburide, or a gliclazide, nateglinide or repaglinide, a thiazolidinedione selected from pioglitazone or rosiglitazone, an alpha-glucosidase inhibitor selected from acarbose or miglitol, insulin or an insulin-analog. In certain embodiments, such a combination of a compound targeted to DYRK1B as described herein and a glucose-lowering agent, such as a glucose-lowering agent is selected from: a PPAR agonist, a dipeptidyl peptidase (IV) inhibitor, a GLP-I analog, insulin or an insulin analog, an insulin secretagogue, a SGLT2 inhibitor, a human amylin analog, a biguanide, an alpha-glucosidase inhibitor, metformin, sulfonylurea, rosiglitazone, acetohexamide, chlorpropamide, tolbutamide, tolazamide, glimepiride, a glipizide, a glyburide, or a gliclazide, nateglinide or repaglinide, a thiazolidinedione selected from pioglitazone or rosiglitazone, an alpha-glucosidase inhibitor selected from acarbose or miglitol, insulin or an insulin-analog, is useful for decreasing blood glucose levels, regulating insulin levels, increasing glucose tolerance, increasing insulin sensitivity, reducing LDL cholesterol levels, decreasing triglyceride levels, reducing blood pressure and reducing body-mass index, or a combination thereof and/or treating a metabolic disease or disorder.

In certain embodiments the compound targeted to DYRK1B, as described herein and the secondary agent are used in combination treatment by administering the two agents simultaneously, separately or sequentially. In certain embodiments the two agents are formulated as a fixed dose combination product. In other embodiments the two agents are provided to the patient as separate units which can then either be taken simultaneously or serially (sequentially).

Advantages of Certain Embodiments

Provided herein, for the first time, are methods and compositions for the modulation of a DYRK1B nucleic acid that can treat, delay, prevent and/or ameliorate a metabolic didease, disorder or condition, or a physiological marker thereof. In a particular embodiment, for the first time, DYRK1B inhibitors (e.g., oligonucleotides targeting a nucleic acid encoding DYRK1B) are provided for decreases blood glucose levels, regulates insulin levels, increases glucose tolerance, increases insulin sensitivity, reduces LDL cholesterol levels, decreases triglyceride levels, reduces blood pressure and reduces body-mass index, or a combination thereof in an animal.

EXAMPLES

Non-limiting Disclosure and Incorporation by Reference

While certain compounds, compositions and methods described herein have been described with specificity in accordance with certain embodiments, the following examples serve only to illustrate the compounds described herein and are not intended to limit the same. Each of the references recited in the present application is incorporated herein by reference in its entirety.

Example 1: Antisense Inhibition of Mouse DYRK1B in TCMK-1 Cells

Three hundred antisense oligonucleotides were screened in TCMK-1 and HEPA1-6 cells and the top 10 oligonucleotides were evaluated in vivo. The studies described below are a representative of these extensive experiments.

Antisense oligonucleotides were designed targeting a DYRK1B nucleic acid and were tested for their effects on DYRK1B mRNA in vitro. Cultured TCMK-1 cells at a density of 20,000 cells per well were transfected using electroporation with 7,000 nM antisense oligonucleotide. After a treatment period of approximately 24 hours, RNA was isolated from the cells and DYRK1B mRNA levels were measured by quantitative real-time PCR. Mouse primer probe set RTS34826 (forward sequence GATGAAC-CAGCATGATACAGAGA, designated herein as SEQ ID NO: 10; reverse sequence CGTACAGGTTGTAG-GACAGC, designated herein as SEQ ID NO: 11; probe sequence CACCTTAAGCGGCACTTCATGTTCC, designated herein as SEQ ID NO: 12) was used to measure mRNA levels. DYRK1B mRNA levels were adjusted according to total RNA content, as measured by RIBOGREEN®. Results are presented as percent inhibition of DYRK1B, relative to untreated control cells.

The chimeric antisense oligonucleotides in the Table below were designed as 5-10-5 MOE gapmers. The gapmers are 20 nucleosides in length, wherein the central gap segment comprises of ten 2'-deoxynucleosides and is flanked by wing segments on the 5' direction and the 3' direction comprising five nucleosides each. Each nucleoside in the 5' wing segment and each nucleoside in the 3' wing segment has a 2'-MOE modification. The internucleoside linkages throughout each gapmer are phosphorothioate (P=S) linkages. All cytosine residues throughout each gapmer are 5-methylcytosines.

"Start site" indicates the 5'-most nucleoside to which the gapmer is targeted in the mouse gene sequence. "Stop site" indicates the 3'-most nucleoside to which the gapmer is targeted mouse gene sequence. Each gapmer listed in the Tables below is targeted to the mouse DYRK1B genomic sequence, designated herein as SEQ ID NO: 1 (RefSeq No. NT_187034.1 truncated from nucleotides 25178000 to 25189000).

TABLE 1

Inhibition of mouse DYRK1B mRNA by 5-10-5 MOE gapmers targeting SEQ ID NO: 1

| ISIS NO | SEQ ID NO: 1 Start Site | SEQ ID NO: 1 Stop Site | Sequence | % inhibition | SEQ ID NO |
|---|---|---|---|---|---|
| 793673 | 8385 | 8404 | ATCGGTAGGCTCTGTTGTCG | 0 | 13 |
| 793684 | 9066 | 9085 | CCTCTCCCTTGACCCCTGC | 0 | 14 |
| 793686 | 9180 | 9199 | AATCTCCCCTCTACCGGACC | 23 | 15 |
| 793688 | 2317 | 2336 | GGTGGCGGCGGCGATGAGGA | 0 | 16 |
| 793691 | 1789 | 1808 | CCCTCGGGCTCAGCCTCTTC | 8 | 17 |
| 793693 | 2314 | 2333 | GGCGGCGGCGATGAGGAGGT | 0 | 18 |
| 793694 | 2534 | 2553 | CTTGTCAGATCCCCTTCTAT | 0 | 19 |
| 793695 | 2664 | 2683 | CTACGCTGGGTCATTCCACA | 40 | 20 |
| 793696 | 2921 | 2940 | CTATAGATGTTTCAACCACC | 15 | 21 |
| 793697 | 3154 | 3173 | AGGCAGAAACCGTGTAGAGT | 0 | 22 |
| 793698 | 3697 | 3716 | CCCTTCAATCCTCAGGCAGG | 10 | 23 |
| 793762 | 9073 | 9092 | CCAAACTCCTCTCCCTTGAC | 12 | 24 |
| 793771 | 2475 | 2494 | CACAGATAAACAACCTCTTC | 3 | 25 |
| 793773 | 2704 | 2723 | TTTCTTCTTTACCCTGAGGT | 29 | 26 |
| 793774 | 2972 | 2991 | ATGGACCTCCCAGCAAACCC | 41 | 27 |
| 793775 | 3247 | 3266 | GGAGCCATCAGAGCCAGACA | 20 | 28 |
| 793704 | 4967 | 4986 | TCACATCCCTTATACTGGAT | 35 | 29 |
| 793705 | 5375 | 5394 | CGTCCCTCACCAGCTGCGGG | 0 | 30 |
| 793706 | 5633 | 5652 | AAGCAAAACCTCCAAAAGTA | 0 | 31 |
| 793707 | 5892 | 5911 | GTCAAAACAGCTCCACATTT | 2 | 32 |
| 793777 | 3903 | 3922 | TGTTGTGAACCTTCAGACCT | 13 | 33 |
| 793778 | 4151 | 4170 | TTCCATTCTGCCCCAGGTCA | 18 | 34 |
| 793710 | 6693 | 6712 | TCAGCTTCATCCTTTCTCTT | 4 | 35 |
| 793783 | 5532 | 5551 | TGTCCTCTACAGAGTCCCTT | 30 | 36 |
| 793712 | 8483 | 8502 | CCACCCTCTTCCAAAATTTC | 0 | 37 |

Example 2: Dose-dependent Antisense Inhibition of Mouse DYRK1B in HEPA1-6 Cells Gapmers from Example 1 exhibiting significant in vitro inhibition of DYRK1B mRNA were selected and tested at various doses in HEPA1-6 cells. Cells were plated at a density of 20,000 cells per well and transfected using electroporation with 0.7 µM, 2.2 µM, 6.7 µM, and 20.0 µM concentrations of antisense oligonucleotide. After a treatment period of approximately 16 hours, RNA was isolated from the cells and DYRK1B mRNA levels were measured by quantitative real-time PCR. Mouse primer probe set RTS34826 was used to measure mRNA levels. DYRK1B mRNA levels were adjusted according to total RNA content, as measured by RIBOGREEN®. The half maximal inhibitory concentration ($IC_{50}$) of each oligonucleotide is presented. DYRK1B mRNA levels were significantly reduced in a dose-dependent manner in antisense oligonucleotide treated cells.

TABLE 2

Efficacy of mouse oligonucleotides targeting DYRK1B

| IsisNo | $IC_{50}$ (µM) |
| --- | --- |
| 793686 | <0.7 |
| 793695 | 0.7 |
| 793696 | 3.8 |
| 793704 | 3.8 |

Example 3: Effect Antisense Inhibition of DRYK1B in the Ob/Ob Mouse Model of Obesity Leptin is a hormone produced by fat that regulates appetite. Deficiency of this hormone in both humans and in non-human animals, leads to obesity. ob/ob mice have a mutation in the leptin gene which results in obesity and hyperglycemia. As such, these mice are a useful model for the investigation of obesity and diabetes and related conditions provided herein. These mice models are also useful for testing compounds, compositions and methods designed to treat, prevent or ameliorate such conditions.

Treatment

In accordance with the present invention, the effects of antisense inhibition of DYRK1B were investigated in the ob/ob mouse model of obesity. C57Bl/6J-Lep$^{ob}$/Lep$^{ob}$ (ob/ob) mice at 4 weeks of age were purchased from Jackson Laboratories (Bar Harbor, Me.). During a 1 week acclimation period and throughout the study, mice were fed a diet with added cocoa butter, cholesterol, and sodium cholate and a fat content of 10-15% (Labdiets #5015, Purina, St. Louis, Mo.).

The mice were divided into 4 groups of 6 mice each based on body weight and body fat content. Two groups of mice was treated with 25 mg/kg or 50 mg/kg of ISIS 793695 administered subcutaneously weekly for 5 weeks. The third group of mice was treated with 50 mg/kg control oligonucleotide, ISIS 141923 (CCTTCCCTGAAGGTTCCTCC, 5-10-5 MOE gapmer with no known murine target; SEQ ID NO: 38) administered subcutaneously weekly for 5 weeks. A control group of mice was treated with PBS administered subcutaneously weekly for 5 weeks.

RNA Analysis

RNA was extracted from the liver, white adipose tissue (WAT), and quadricep muscle (Quad) for RT-PCR analysis of murine DYRK1B expression. The data was normalized to the housekeeping gene, cyclophilin. The results are presented in the Table below and demonstrate the in vivo inhibition of DYRK1B by antisense oligonucleotide.

TABLE 3

Dose-dependent in vivo inhibition (%) of mouse DYRK1B

| Dose (mg/kg) | Liver | WAT | Quad |
| --- | --- | --- | --- |
| 25 | 75 | 66 | 21 |
| 50 | 82 | 77 | 32 |

Effect on Glucose Tolerance

Glucose tolerance was measured via the intraperitoneal glucose tolerance test at week 3. The mice were fasted overnight and then an intraperitoneal administration of glucose at 0.50 g/kg was given. Blood glucose levels were measured before the glucose challenge and at different time points after challenge up to 120 min. The results for the area under the curve (AUC values) are also presented below and are found to be statistically different for mice treated with ISIS 793695 at 50 mg/dl compared to the PBS control as well as the oligo control.

As presented in the Tables below, in antisense oligonucleotide treated mice, initial glucose levels were lower and the increase in glucose levels during the IPGTT assay was less than in the saline control. Therefore, antisense oligonucleotide treated mice had better glucose tolerance as compared to the saline controls.

TABLE 4

Glucose (mg/dL) in ob/ob mice

| | Dose (mg/kg) | 0 min | 15 min | 30 min | 60 min | 90 min | 120 min |
| --- | --- | --- | --- | --- | --- | --- | --- |
| PBS | | 219 | 388 | 392 | 340 | 305 | 331 |
| ISIS 141923 | 50 | 231 | 447 | 433 | 346 | 314 | 334 |
| ISIS 793695 | 25 | 224 | 354 | 395 | 278 | 246 | 278 |
| | 50 | 192 | 394 | 350 | 287 | 294 | 277 |

TABLE 5

AUC values in ob/ob mice

| PBS | 43932 |
| --- | --- |
| ISIS 141923 | 44639 |
| ISIS 793695 | 35149 |

Fed Glucose Level Analysis

Plasma levels of glucose were measured using an automated clinical chemistry analyzer (Olympus Clinical Analyzer). The results are presented in the Table below, expressed in mg/d/L. Treatment with ISIS oligonucleotide resulted in lowering of fed glucose levels in the plasma over the PBS control at weeks 2 and 5. Therefore, antisense inhibition of DRK1B resulted in significant reduction of fed glucose levels in mice compared to the control.

TABLE 6

Fed glucose levels (mg/dL) in ob/ob mice

| | Dose (mg/kg) | Week 2 | Week 5 |
|---|---|---|---|
| PBS | | 523 | 503 |
| ISIS 141923 | 50 | 438 | 500 |
| ISIS 793695 | 25 | 364 | 416 |
| | 50 | 335 | 330 |

Body Weight

Weekly body weights were measured and are presented in the Table below. The data indicates that antisense inhibition of DYRK1B had no adverse effects on body weight outside outside the expected range for antisense oligonucleotides.

TABLE 7

Weekly body weights (g)

| | Dose (mg/kg) | Week 0 | Week 1 | Week 2 | Week 3 | Week 4 |
|---|---|---|---|---|---|---|
| PBS | | 39 | 43 | 47 | 51 | 53 |
| ISIS 141923 | 50 | 39 | 44 | 48 | 53 | 54 |
| ISIS 793695 | 25 | 38 | 44 | 47 | 52 | 53 |
| | 50 | 38 | 43 | 47 | 52 | 53 |

In addition, plasma levels of transaminases, bilirubin, triglycerides, and cholesterol were measured. The data indicates that antisense inhibition of DYRK1B had no adverse effects on these plasma chemistry markers outside outside the expected range for antisense oligonucleotides.

Example 4: Antisense Inhibition of DYRKIB in the Diet-Induced Model of Obesity (DIO)

The C57BL/6 mouse strain is reported to be prone to diet-induced obesity and is accepted as a model for diet-induced obesity for human (C. Gallou-Kabani et al, *Obesity* (2007) 15, 1996-2005). To induce obesity, these mice were fed a high-fat diet and used in the following studies to evaluate the effect of antisense inhibition of DRK1B.

Treatment

C57BL/6 mice were fed for a 60% high fat diet for 16 weeks. The start weights of the mice were 32-40 g. The mice were then divided into 3 groups of 3 mice each based on body weight and body fat content. One group of mice was treated with 37.5 mg/kg of ISIS 793695 administered subcutaneously twice weekly (75 mg/kg/week) for 7 weeks. Another group of mice was treated with 37.5 mg/kg of control oligonucleotide, ISIS 141923 administered subcutaneously twice weekly (75 mg/kg/week) for 7 weeks. A control group of mice was treated with PBS administered subcutaneously twice weekly for 7 weeks.

Fed Glucose Level Analysis

After 2 weeks of treatment, plasma levels of glucose were measured using an automated clinical chemistry analyzer (Olympus Clinical Analyzer). The results are presented in the Table below, expressed in mg/d/L. Treatment with ISIS oligonucleotide resulted in lowering of fed glucose levels in the plasma over the PBS control. Therefore, antisense inhibition of DRK1B resulted in significant reduction of fed glucose levels in mice compared to the control.

TABLE 8

Fed glucose levels (mg/dL) in DIO mice

| | Glucose |
|---|---|
| PBS | 214 |
| ISIS 141923 | 191 |
| ISIS 793695 | 179 |

Insulin Sensitivity Analysis

After 7 weeks of treatment, insulin sensititivy in the mice was measured by the intraperitoneal insulin tolerance test (IPITT). The mice were fasted overnight, injected intraperitoneally with human recombinant insulin at 0.75 U/kg and tested for blood glucose levels over a period of 2 hours. The blood glucose levels (mg/dL) are shown below in the Table below. The glucose levels in mice treated with ISIS 793695 were significantly lower than controls during ITT. The results for the area under the curve (AUC values) are also presented below and are found to be statistically different for mice treated with ISIS 793695 at 50 mg/dl compared to the PBS control as well as the oligo control.

TABLE 9

Glucose levels (mg/dL) in DIO mice

| | 0 min | 15 min | 30 min | 60 min | 90 min | 120 min |
|---|---|---|---|---|---|---|
| PBS | 72 | 89 | 61 | 41 | 42 | 54 |
| ISIS 141923 | 76 | 87 | 62 | 45 | 46 | 59 |
| ISIS 793695 | 68 | 76 | 53 | 37 | 32 | 44 |

TABLE 10

AUC values in DIO mice

| PBS | 6650 |
|---|---|
| ISIS 141923 | 6993 |
| ISIS 793695 | 5580 |

In addition, plasma levels of transaminases, bilirubin, triglycerides, and cholesterol were measured. The data indicates that antisense inhibition of DYRK1B had no adverse effects on these plasma chemistry markers outside outside the expected range for antisense oligonucleotides.

These data support the role of DYRK1B in glucose homeostasis and suggest that antisense inhibition of DYRK1B may be a novel approach for treating hyperglycemia and metabolic diseases.

Example 5: Specificity of Inhibition of DYRK1B but not of DYRK1A In Vivo

In order to demonstrate the specificity of Ionis oligonucleotides to DYRK1B, C57BL/6 mice were dosed with oligonucleotides targeting DYRK1B, and the expression levels of DYRK1B and DYRK1A were evaluated.

Additional antisense oligonucleotides were designed targeting a DYRK1B nucleic acid. The chimeric antisense oligonucleotides in the Table below were designed as 3-10-3 cEt gapmers. The gapmers are 16 nucleosides in length, wherein the central gap segment comprises of ten 2'-deoxynucleosides and is flanked by wing segments on the 5' direction and the 3' direction comprising three nucleosides each. Each nucleoside in the 5' wing segment and each nucleoside in the 3' wing segment has a cEt sugar modification. The internucleoside linkages throughout each gapmer are phosphorothioate (P=S) linkages. All cytosine residues throughout each gapmer are 5-methylcytosines.

"Start site" indicates the 5'-most nucleoside to which the gapmer is targeted in the mouse gene sequence. "Stop site" indicates the 3'-most nucleoside to which the gapmer is targeted mouse gene sequence. Each gapmer listed in the Table below is targeted to the mouse DYRK1B genomic sequence, designated herein as SEQ ID NO: 1 (RefSeq No. NT_187034.1 truncated from nucleotides 25178000 to 25189000).

TABLE 11

3-10-3 cEt gapmers targeting SEQ ID NO: 1

| ISIS No | Start Site | Stop Site | Sequence | SEQ ID NO |
|---|---|---|---|---|
| 860464 | 2584 | 2599 | CTAAAAGTGTCCTTCG | 39 |
| 860466 | 2601 | 2616 | GCACAAGACTTCACTC | 40 |
| 860471 | 2613 | 2628 | TCCCTAAATATCGCAC | 41 |
| 860491 | 2726 | 2741 | TCTAAGAGTCACGGTC | 42 |
| 860492 | 2728 | 2743 | CATCTAAGAGTCACGG | 43 |
| 860493 | 2729 | 2744 | ACATCTAAGAGTCACG | 44 |
| 860521 | 2923 | 2938 | ATAGATGTTTCAACCA | 45 |
| 860597 | 4011 | 4026 | AGTTACAAAGCTCCTG | 46 |

Treatment

Groups of C57BL/6 mice were treated with 50 mg/kg of ISIS 860464, ISIS 860466, ISIS 860471, ISIS 860491, ISIS 860492, ISIS 860493, ISIS 860521, or ISIS 860597, administered subcutaneously weekly for 4 weeks. Another group of mice was treated with 50 mg/kg of control oligonucleotide, ISIS 549144 (GGCCAATACGCCGTCA; SEQ ID NO: 47; 3-10-3 cEt apmer with no known target) administered subcutaneously weekly for 4 weeks. A control group of mice was treated with PBS administered subcutaneously weekly for 4 weeks. DYRK1B and DYRK1A expressions were measured and normalized to RIBOGREEN®. The results are presented in the Table below and demonstrate that most Ionis oligonucleotides inhibit DYRK1B expression levels in a number of tissues, but not DYRK1A expression levels. Hence, Ionis oligonucleotides are highly specific in inhibiting DYRK1B mRNA expression.

TABLE 12

% inhibition in the liver compared to PBS control

| ISIS No | DYRK1B | DYRK1A |
|---|---|---|
| 549144 | 28 | 21 |
| 860464 | 48 | 0 |
| 860466 | 74 | 1 |
| 860471 | 52 | 0 |
| 860491 | 53 | 0 |
| 860492 | 64 | 0 |
| 860493 | 72 | 27 |
| 860521 | 61 | 0 |
| 860597 | 4 | 0 |

TABLE 13

% inhibition in the quadricep muscle compared to PBS control

| ISIS No | DYRK1B | DYRK1A |
|---|---|---|
| 549144 | 0 | 5 |
| 860464 | 31 | 0 |
| 860466 | 35 | 0 |
| 860471 | 32 | 0 |
| 860491 | 31 | 0 |
| 860492 | 35 | 0 |
| 860493 | 47 | 0 |
| 860521 | 46 | 1 |
| 860597 | 19 | 14 |

TABLE 14

% inhibition in the white adipose tissue compared to PBS control

| ISIS No | DYRK1B | DYRK1A |
|---|---|---|
| 549144 | 30 | 0 |
| 860464 | 33 | 0 |
| 860466 | 45 | 0 |
| 860471 | 55 | 0 |
| 860491 | 44 | 0 |
| 860492 | 64 | 0 |
| 860493 | 71 | 0 |
| 860521 | 70 | 0 |
| 860597 | 41 | 0 |

What is claimed is:

1. A method of treating a metabolic disease or disorder in an individual having, or at risk of having, a metabolic disease or disorder comprising administering to the individual a therapeutically effective amount of a compound comprising a modified oligonucleotide, wherein the modified oligonucleotide consists of 12 to 30 linked nucleosides and is complementary to a DYRK1B nucleic acid thereby treating the metabolic disease or disorder in the individual.

2. The method of claim 1, wherein the metabolic disease or disorder is diabetes, obesity, hypertension, hyperglycemia, or metabolic syndrome.

3. The method of claim 2, wherein the diabetes is Type 2 diabetes.

4. The method of claim 1, wherein the metabolic disease or disorder is disorders of lipid metabolism.

5. The method of claim 1, wherein plasma glucose levels are reduced.

6. The method of claim 1, wherein insulin levels are regulated.

7. The method of claim 1, wherein the compound is single-stranded.

8. The method of claim 1, wherein the modified oligonucleotide comprises at least one modified internucleoside linkage, at least one modified sugar moiety, or at least one modified nucleobase.

9. The method of claim 8, wherein the at least one modified internucleoside linkage of the modified oligonucleotide is a phosphorothioate internucleoside linkage, the at least one modified sugar is a bicyclic sugar or 2'-O-methyoxyethyl and the at least one modified nucleobase is a 5-methylcytosine.

10. The method of claim 8, wherein at least one modified sugar comprises a 4'-CH(CH$_3$)—O-2' bridge or a 4'-(CH$_2$)$_n$—O-2' bridge, wherein n is 1 or 2.

11. The method of claim 1, wherein the modified oligonucleotide comprises:
- a gap segment consisting of linked deoxynucleosides;
- a 5' wing segment consisting of linked nucleosides;
- a 3' wing segment consisting linked nucleosides;
- wherein the gap segment is positioned immediately adjacent to and between the 5' wing segment and the 3' wing segment and wherein each nucleoside of each wing segment comprises a modified sugar.

12. The method of claim 1, wherein compound is administered parenterally.

13. The method of claim 12, wherein the compound is administered by subcutaneous or intravenous administration.

* * * * *

UNITED STATES PATENT AND TRADEMARK OFFICE
CERTIFICATE OF CORRECTION

PATENT NO. : 10,577,607 B2
APPLICATION NO. : 16/085140
DATED : March 3, 2020
INVENTOR(S) : Brett P. Monia et al.

Page 1 of 1

It is certified that error appears in the above-identified patent and that said Letters Patent is hereby corrected as shown below:

In the Claims

Column 107
Claim 1 delete:
"a DYRK1B nucleic acid"

And insert:
-- SEQ ID NOS:2-5 --

Signed and Sealed this
Fifth Day of May, 2020

Andrei Iancu
*Director of the United States Patent and Trademark Office*

SEQUENCE LISTING

<160> NUMBER OF SEQ ID NOS: 47

<210> SEQ ID NO 1
<211> LENGTH: 11001
<212> TYPE: DNA
<213> ORGANISM: Mus musculus

<400> SEQUENCE: 1
acaacaggag tggatgagtg atgtgacttt cgtgttctgg atccaccttt ggggtgcttt      60
ggagggaggc tgtgtggtgg ggggtaagac tggaggcaag agagtcccag gaacctggtg     120
gtgaaggagc acaggccctg ttgggaggct ctggggagct ctctgctgcc ttgtttgtag     180
taaccgctgt ccctttttc cttagcaatg gtggatgtca tctttgccga tgtggcccag      240
ccagaccaaa cccgaattgt ggccctgaac gcccacacct tcctgcggaa tggaggacac     300

```
tttgtgattt ccattaaggt atgggtcttg ccatgtaagg ttgagtaacc ctagagtgtg    360
gtgtgggtgc tttgtctctg tggctgagca ggttatggcg ccttagccta tctgacttgt    420
ttattagtcc tccttatggc tgaaataaag actgatagct gctaagcatt tggagcagat    480
tgtggggtac aatattaact gcagcaggta catttttcaa aacattttaa ttttaaatag    540
ggaaaactct cgcgcatcct caccatgttc aaaactggcc aacctattgc tacacttgtt    600
tttgggtttt ttttttgttt tgttttgttt ttgttttttc aagacagagt tttctctgta    660
tagccctggc tgtcctggaa ctcaactctg tagaccaggc tgctattgct acatttgttc    720
tgttttttgcc agctgggctt ccaggatatg aagaaaatt cctgacctta aacactgcct    780
tagataaatg aaataacctg tttccaatgt gagccaaatt aaaacttctt taatgaagtt    840
agaaaattgg aaagcctggg tctccaaat ctgtaactta gtcctgactc ctttctaggc    900
caactgcatt gactccactg cgtcagcaga ggctgtgttt gcatctgaag tgaagaagat    960
gcagcaggag aacatgaagc cgcaggagca gctgacgcta gagccttatg agcgagacca   1020
cgccgtggtt gtcggtgtgt acaggtgagt gtcacaacag acctctccct tacctgtggc   1080
cctgagaagc caaagtggt tacaactcga cccctctga tttcctcaca ggccacctcc    1140
caaggtgaag aactgaaact cagagctgtc tggattgaag agatgtgtgt tgttactgtt   1200
gcacgtgtgg cttgtgattt tttggggcg ggggagttgt tttgttttc tattaaaaga    1260
ctcatctgtc tccctgtct ggtgccatt gctaagtggc ctcgagacgc atgcgccctt    1320
gatcaactttt gtgtgcttcg ggggtggtg cctggaaagt ttcatccggt cacatggtgc    1380
atgctccatt ggtggctgct ccgcacgtgc gcggctcagc accccttaagg cgcaggcgca   1440
ctgtgctccg ctaggtcacg tgaatgatgt gggggcggag ccggggcagg ggggccggtt   1500
tgttgtggtc gccatttttgc tggttgcatt actgggtaat cggggccctg gctcgccgcg    1560
tccaccggac ccctcagcc agtgggcagg tctgagctcg gctccccga gcagtttgaa    1620
tccccttacc cacgccctca ggtaagggtg ctgcgacggg cggggcggca cgcttgggtg   1680
gggggcaggc cgggaaccgc cctgcccgtc cccgcgagat ttagcaaggg aaaggagggg   1740
gctttgggcc gttgcagcgg agtccggctc ttcatagctg gattcctgga agaggctgag   1800
cccgagggag ccgtcctgag agggagtcgg ggaggggca gccaggcccc actcccgccc    1860
tttgtttggg ctcggctgcg ctggccgctt cgctgtcgcc tagcaacagc tgccctgagt   1920
gctaattggt taagctcttg gcagcaacaa ccaatggcgc ggttgttgcc atgggaggtg   1980
cggcctgccg ggctctcttg ggccccgccc gccgggactc cactggccgg ggcgggcctg   2040
ccgggtgggg ggcgggacgc cagggtccct ggggggcgggt ggccacgcgg ggcggggctg   2100
ggccgtaggg cgagggttaa cccgcccctc ccccgtccac ctgctgtccc cttccccgc    2160
gtgccctggt ctgaccctcg tcccctcctt tccccgcccc tccccctcgg tggcagtggc   2220
ggcggctgct gttgtcaccc accgggccgc ctgtcccgct tgccctcacc gccgcgggc    2280
tggctaggct agccgggccg gggacaggcg gccacctcct catcgccgcc gccaccacca   2340
ccgccgccat gctggccgct cgcccaccgc actgggtcc ccatcgcgct ccagccccc    2400
gtgggcccag cgccatccct gacccgggta ggggtgggag ctgtaagagc tggtcctagt   2460
gtgggagggc tcgggaagag gttgtttatc tgtgaagccc caataaaggg gacctggagt   2520
ggcaagacat agcatagaag gggatctgac aagggggagg ctcctaagaa ggggattttg   2580
ttccgaagga cacttttagt gagtgaagtc ttgtgcgata tttagggatt tggctgtcag   2640
gcccttctag gaataggctc aattgtggaa tgacccagcg tagaaataga ggagctagca   2700
```

```
aggacctcag ggtaaagaag aaaaagaccg tgactcttag atgttgaaaa atgacacctc    2760
tcccttgttt tcctgaggag tagggtctt ggagtaatgg gggaatccta gtgggataaa    2820
tatagactgc ttaaaagaag gatctctggt tccagagacc tcatataggg agcagggagc    2880
ggtcttggag tatggagtcg gtcccagggg aaagtgccga ggtggttgaa acatctatag    2940
cttgcatgta aaggagttct cagataacct tgggtttgct gggaggtcca taaggactgc    3000
tatgttcttt agaatagaaa gaaactagtg ggtagactgg gcttgaaatt gggcccttgg    3060
tgttgaggga agacggtgtg agggcgggc cttatctgag ggactcaggc tggccaccag    3120
taaaattttg aaggactgag ttctactgcc cagactctac acggtttctg ccttcttttg    3180
ctctcctaat tcctggcctc tttctatccc tcctgccctg gccttgtacc caccctctcc    3240 caccccgtc tggctctgat ggctcccttt tacatctctg gatgtgatgc ttcattcatt    3300 tttttggct cctcatttgt tgagagacac gctgtgctaa cccacttgct accctttctg    3360
tttgtacatg gctacctggt gctggtgctc tgccctgtcc cctgtctccc ctggtcctg    3420 cccctaactc atacccacct cttctgactg accctgacct acatgccttc ttgttccatg    3480
ttgtcttccc acttcctacc tgctctcagg tctcagcggc ggtggcagcc gaggtgcagg    3540
atgcgagaag gcgccccccg gccgggctcc cgctccaggc ctcacgcccc tgcggccctc    3600
tgagcccacc atggccgtcc caccaggcca tggtcctttc tctggctttc cggggcccca    3660
ggaacacaca caggtaggca ttcagctggc ttctcacctg cctgaggatt aagggtctc    3720 cagacaagag catgattgtt ggaggatctc tggggacttt ggaggcctca cagtccaccc    3780
tcattcctgc tgaggacgga atccttgagc ttctccgtgg cctgccctct cacagcatgg    3840
ttttgaagtg taatgtgtgt cttgggtcag aactgtcact ggcacagagc agacaggaac    3900
acaggtctga aggttcacaa caagaacgag gtctggagta aggggcatga gagagatgtc    3960 gagggggtg gaaatgagaa taagctgaga ccagggagac taacccagtc caggagcttt    4020
gtaactgggc agaaacactc acttgagagt gaggacatgg atacagggaa ttcattggca    4080
tggttcccca taatggtggt ctcaggtgca aagattcagg ggtaaacacc cagatatgga    4140
gcaaaagagc tgacctgggg cagaatggaa ggccagaggt aaatcactca tttcacataa    4200
tgaacagatg aatggggagc ccacacagtg tgcttgtgct ctacaggtgg gatcggagct    4260
agagaaatgt aggcatggtc agtgagtcgt cagctttccc attctctccc tggaagttga    4320
ggtgaaggct tgtgctcagc atctgctccg ctctaccaca ggtactacct gatgtgcggc    4380
tcctgccccg gagactgccc ctggccttcc gggatgcggc ctcagccccg ctgcgcaagc    4440
tctcggtgga cctcatcaag acctacaagc acatcaatga ggtaaagcgg ggaatggact    4500
tccctggttg ggtgttgcaa agggtcctgg cttcttgccc gggtcactta agggtccggt    4560
ttcctggctg cctgagcagg tatactatgc gaagaagaag cggcgggccc aacaggcgcc    4620
accccaggac tcgagcacca aaaggagaa gaaggtcctg aaccacggtt atgatgacga    4680
caaccacgac tacattgtgc gcagtggcga gcgctggcta gagcgctatg agattgactc    4740
tcttattggc aaaggctcct ttggccaggt gtgggactcc ccactcatcc agtatctgga    4800
tgcagacaac cactaacatt cccaacattc cctcctcccc gagtggttca ctggttcact    4860
tgctgcaagt tctgtcctgg accagccagt caagccactt agtttccctc ttagttctgt    4920
atgagtataa atcacaaggc ttcttgtaag aaaactgtta ttttgtatcc agtataaggg    4980
atgtgagcac tgggctgtga gttgttagaa aggtgtggct ggtgggcctc ccaccttccc    5040
```

```
aggtaactct ccttgtctcg acaggtggtg aaagcctatg atcaccagac tcaggagctg    5100
gtggccatca agatcatcaa gaacaaaaag gccttcctga accaggcaca gattgagcta    5160
cggctgttgg agctgatgaa ccagcatgat acagagatga agtactacat aggtgaggcc    5220
tgggcttggg caggtgcagg gtgcctgtgg gagagagacc tccacgaggg tctttgggct    5280
tctcatcctt tgattctcct gctgtgctca ggatttctct cttgtgctca ctgagggcca    5340
gattgtgttg caaacccttg ctttgaatta cctccccgca gctggtgagg acggggcag    5400
ctctgagtac atgttggaga gactgaggca ctcagtgctc tcacatcaga ctcaacagct    5460
gaggatgtga aaagcagtgg cctctagagc tctggctctt gagatatgtc ccagtcttca    5520
gttcctctgg aaagggactc tgtagaggac agccagtatc ccttggcaca tgggtagaca    5580
cagcaaagac gagagcaggc tcttttggta gttcgggttt tggtgatggt gatacttttg    5640
gaggttttgc tttgctattc tggggatcga gcccagtgct ttatatgtaa taggcaaaca    5700
ggtcctcccc tcaaccatcc ccaccccaga acatctccag accttttgtt acttgactat    5760
tttgagatag ggtctcagta aatatatcca gatgaacctt gagctaacag tcttcgtgca    5820
tcagtgtaca aagacctggg tctccatgcc tacaccccag gcctgattca gtgttgtcaa    5880
atgaagtgag taaatgtgga gctgttttga cgctttatta ggagggaaca gtacctttta    5940
tttccctttg cagtgctggg gcctgaaccc tgggccttgt gcttgctagg caagcgtgct    6000
gctgcccttt ggtcatccca taatctacgc tagagtaacc ctagattata tcatcctttg    6060
gggttttgga actggaaggt gtgagagacg caagagaatt aacatgcctt ggaagtccag    6120
tgagttggtg tagaaacacc tgagggctca ctgcaggtta ccagaggtgg tcactgtgaa    6180
gtcccaagcc acctgccatc agtgtgtcta acctgttccc cactgtcacc gttgcccgca    6240
gtacaccttc agcggcactt catgttccgg aatcacctgt gcctggtgtt tgagctgctg    6300
tcctacaacc tgtacgacct cctccgcaac acacactttc ggggtgtctc actgaacctg    6360
acgaggaagc tggcacagca gctctgcaca gctctgctct ttctggccac ccccgagctc    6420
agcatcatcc actgcgacct caagcctgag aacatcctgc tctgcaaccc caagcgcagt    6480
gccatcaaga tcgtggactt cggcagttcc tgccagcttg ccagcgggt gcggttctga    6540
ctgtgggcag ggccgatgtc tttggtggga tggggtggga tggcttcatt ttggccctgg    6600
aagctgatgg ccaagggatg atattgttca taggaaggcc cacctggaga gaggtggtgg    6660
gaggtgaagg ggcaaagatg acccaagcaa ggaagagaaa ggatgaagct gatggccagg    6720
ccatctcaga ggagtggagt tgtgatctga gcctcaggct gctttgctga tgctcacagg    6780
gagagtgccc tgaagcctgt ggttatactc atatagtacg gtgcatgatg ccagcctct    6840
cttaaacaag aagggccaga gctgggaatg gaggcgggtt aaggcagaaa ggccattgaa    6900
gactggaggc tcatgggcag acagtgttg gtggcttgtg caacattgct cagagcctcc    6960
cgacctagag gttccatcct gttttcaggc ggggctttg tcttcagttg attctcccag    7020
tggaaccagc agggagctg gtgccctgac tactgtcccc tcccccagat ctaccagtat    7080
atccagagcc gcttctaccg ctcacccgag gtgctcctgg gtacacccta tgacctggcc    7140
attgacatgt ggtccctggg ctgcatcctc gtggagatgc acaccggaga gcccctcttc    7200
agtggctcta atgaggtgtg ccctggaag gggtgtactg gaggtggagg ggtggagccc    7260
ggccacctgg ctcccctgac cgccgcctgc ccgtaggtgg accagatgag ccgtattgtg    7320
gaggtgttga gcatccctcc cgcacccatg ctggaacagg cacccaaggc tcgaaagtac    7380
tttgagcggc tgcctggggg tggctggacc ctacgaagga caaaggaact caggaaggtg    7440
```

```
cggcccctgc cctgtgccac ttctccctcc ctgggtgtcc cctcactcac acttggggct    7500
cccctctccc ggtgtcattc cctgtcttcc tctccccctt gtctgtcctt tccttcctcc    7560
cctgcccacc ccatcgccct cctacccac agctcttgct agctttctct ccctctctct    7620
ttcttgtgcc tctgtttccc cgtgtgtgtc tccctgcccc tcctgcccac tgacggccac    7680
tctcttgccc ccctcccac cccctccctg ccaggattac cagggccctg ggacacggcg    7740
gctgcaggag gtgctgggcg tgcagacggg cgggcccggg ggccggcggg cggggagcc    7800 cggccacagc cccgccgact acctccgctt ccaggacctg gtgctgcgca tgctggaata    7860
tgagcccgcc gccgcatca gccctctggg cgctctgcag catggcttct tccgccgcac    7920
ggccgacgag gccaccaaca cgggcccggc aggcagcagt gcctccacct cgccggcgcc    7980
ccttgacacc tgcccctcct ctagcaccgc cagctccatc tccagctctg gtgggtgccc    8040
catgtcacat gtgtaccaca gggcccagcc tgggtggcct aaccactggg cctctgtcat    8100
agagccccta gaactaccag attctgaggt ggggtgggac agtcctacat gacccaacag    8160
gttctcagaa ttggggcagg agactcggtc cctagatctg actccaccct cccacacaac    8220
tctgacccta gatttcaaac ttgggctgtt gacagccgtc attcacactt gctctggtct    8280
caaagcctaa gcttggggtg gaggacagac ttgcccccat cttaccactt atgtcctctt    8340
ttctccttcc tggtgcttct aggaggttcc agtggctcct ccaacgacaa cagagcctac    8400
cgatacagca accgatattg tggggcccca gggcccccca tcactgactg tgagatgaac    8460 agccccagg tactggagct gtgaaatttt ggaagagggt ggtaggtgcc taggacttga    8520
tctcactgct catgactcct ttgccttttt aggtcctacc ctcccagcct ctgcgcccct    8580 gggcagggg tgatgtgccc cacaagacac atcaagcccc tatctctgcc tcaacattgc    8640
cggggactgg ggctcagtta ccccccattgc ccgttgcct tggacgaccc ccatcaccaa    8700
catcaccacc accccagag ttgatggatg tgagcctggt gggcagccct ccagactgct    8760
ctccacctcc tccagcacct gcccccagc accggctgc ctcagccctc cggactcgga    8820
tgacaggagg tcgaccacct ctcccacccc ctgatgaccc tgccactctg ggcctcgcc    8880 tgggtctcca tggtgtaccc cagagcacag cagccagctc atgaccctgc cccctccctg    8940
gggcccctcc tgaagccata ccccccata tgggggccct gggctcccat cctcatctct    9000
ccccttgact ggacttgctg ctacccagct ggggtgggtg aggcctgcac tgactggggc    9060
ccagggcagg gggtcaaggg agaggagttt ggccgcaccc tccccactaa gactggaccc    9120
ttggcccctc tcttccccct cccccttgt tttctattta ttgtaccaaa gacagtggtg    9180
gtccggtaga ggggagattc ccccttaccc agggccctag gaggggtgg gggcaggtag    9240 ggggagatgg ccttgctcct cctcgctgta cccccagta aaaagctttc tcacatgcct    9300
gcctgagcgt ttgcagggcc ttggctccct cccctgaccc tcagaggcat ggtggggaag    9360
gttgtgtggg gaagggggtgc tttgtggtgt gggtatatcc cttctgggga catcatagtt    9420
cttggtgcag gcatggggca gcaggagatt ggtgggctga gaagcctgga tacaagaatc    9480
ctggcctgtt gctaggaaat gtgatggtct gccctcatcg gtcagggctt ccacagagtc    9540
cacgcagaag tggcttttt tctttttttt tttttttttt tcctgtcagg caggcattcg    9600
gtaggttgtg ggtatattca gcaggctgcc ttaggtacca tcggggagc agacagacag    9660 tgggtacaga ttttacccaa cccgtttcca gccccactct gcagtcattt cgagtattga    9720
gattctcgag caaaaagacg ctccctgacc tccaggtaag tgattttttt gtttccatgg    9780
```

-continued

```
caatttggaa ccaactgtct cccaaccagt ttgtaagact cacttggctc tcccacaagg    9840
gagggtgtgg tgactcctgg gagatggagt tctacaaggc cagctctttg ctcacttttc    9900
tttgggaact acaaagccca gaagtctctg cacacatggc tggggactgg tgttcaataa    9960
gctgtagggc attattgctt agatgttgga ggatccatag tacaggttga ttggatgctg   10020
ctggtgccca ggagtaggat gggtagggag agagagtagt cagccagcct tacagggcca   10080
agcagtggag gctccatgta gagaactctg gtgagcaaga gcctgttgtg gaaactgatg   10140
gcagtggtca ttttgagaat gccatttaag atttatcaga gatcttttgt tatctagaaa   10200
gctggacttt ttcacaggga ctgagacacc atgagaggaa ggtgcacagc ccagttttgc   10260
cacaacatgg aagtatgttg ccaggaaaag gtagcttgta gcaggcccct aggcaagatg   10320
tgacggccat gggttggggg gggtgctaag aagaccagga aagggcaggt gttttccaga   10380
cacctgaggt gaaggaagag acggagacaa gcagaggagg ggagggctcc agtatataga   10440 gcacccagc ccctattaac agagtcttgg ttagtgtttt gttttttaat tatgtgttct   10500
cttggtgctg gggatggaat ccaggaaatc ccagatgcta acaagtatt ctgcgtactc   10560 agcctcccag taaaaggatt ttgaatgaac agttttagaa gacaggaact gcagtgacct   10620
ttccaaattt ggggataatg tgggcaaata aagttacttt tctaaggtca cacaactagg   10680
aagtaggctc aggttgctgt gcatgtgtgc gtgcattcgt gtgtgtgtgt gtgtgtgtgt   10740
gtgtgtgtgt gtgtgtgtgt gtgtgtgtgt gtgtgtgaga gagagagaga gagagagaga   10800
gagagagaga gagagagaga gagagagaga tctagttgtc aattgaacaa ggtgtatttg   10860
agcctggagg catgagcagg gctggttcct gcggaccctg tgaggactgt gggatgggca   10920
tgggtgttgt ctatactgtg gttgagcacc agtgcccagc gccaggctga ctgactagct   10980
gatacctcct tggtatttgc a                                             11001

<210> SEQ ID NO 2
<211> LENGTH: 10001
<212> TYPE: DNA
<213> ORGANISM: Homo sapiens

<400> SEQUENCE: 2
gcacacaaga gaaaacagc ccaaagccct gttgtagaca ttagtccttt ctcctcttta     60
ggccaactgc attgactcca cagcctcagc cgaggccgtg tttgcctccg aagtgaaaaa    120
gatgcaacag gagaacatga agccgcagga gcagttgacc cttgagccat atgaaagaga    180
ccatgccgtg gtcgtgggag tgtacaggtg agcaggggcc cagcaataca ccaagacaga    240
catctctgtc ccttgcaccc cgagtgccat gatcctgggg accctccttc atcacctatc    300
ttcctctcac aggccacccc ccaaggtgaa gaactgaagt tcagcgctgt caggattgcg    360
agagatgtgt gttgatactg ttgcacgtgt gttttttctat taaaagactc atccgtctcc    420
catgtctgct gctcattcct cccttgacc tgctgacaca gggagcacgc acccttggtc     480
aattttgcgg ggttgggtaa attctcactc ggtcacagag cgcatgctcc gtttctagct    540
gcctttgcgc agcggcagcc tggatttcgg ttcttgggtg ggattggtag ctcgctgcgc    600
atgcgtgcag gtaagcggcc atctcgcgca ggcgagtgt cagtgtgggt cacgtgaggg     660
gagcggagag ggagggatgg gggcggagtc cagggcgtgg ggggccggt ttgttgtggt     720 cgccattttg ctggttgcat tactgggtaa tcggggccct ggcttgccgc gtccgccgga    780 tacccctcagc cagtgggcag gtctgagctc gggctcccccg agcagtttga gtcccccttgc  840 ccgctccttc aggtaacggc gcggggacgg gtggggcggc aagcggtcgc agggaggtgg    900
```

```
gcaggacggg atccgccctg ctcccgtcgc cgtgagactt agcacgaggc caagggagga    960
gaggaggggg gtggcaggca ggtgcgggcc ctgcctggct attcatagtt gaattcctgg   1020
aaccggccaa gcccgaggaa gcagttgcag gagggaggct gggaggggt agccgggccc    1080
cactcccgcc ctttgtttgg gctcagctcc gcgggccgct tcttcgtcgc ctagcaacag   1140
ctgccctagg ctgtgattgg ctgagctctt ggcaccagcg accaatggta cagttgttgc   1200
catggcaggt gccgattgcc aagctcagtc gggccccgcc ttccggtctc agcaggccca   1260
ggagggcctc ctgggtgggg ggcgggacgc cgggtccta ggggctggtg gtcactcagg    1320
gtggggcgtg tcgcccctcc cccgtccacc tgctctactc ttccccgcg tgccctgggc    1380
tgacccttgt ccctcctct cccgcccc ggtggcagtg gcggctgctg ttgtcaccca      1440
ccgggcctcc tgtcccgctt gcctccccg ccgcggggcc ggcgggcca gagacaggcg     1500
gtcgccttt cagcgccgcc accgccgcca tgctggccgc tcgcccaccc cactgggggc    1560
cccaccgcgc cccagccccc cgtgggcccc gcgccagccc tgacccgggt aggggtgggg   1620
ggctgggaga gatgatcctg gtgtgggagg ccccggaga agaggtggtt ttttggggga    1680
agctccaagg gtggaggagt cgtggagtgg caaggcatgg aataggagaa agggatttga   1740
catggggag agagtggccc atggggagaa gattttttgct gtagctgaca actctgggag   1800
gagagaaccc tatgtgataa cttggggatt tgactttgag gccctctagg agtggacaca   1860
gttgtggaat gaccctggta taagaggggg tgcctggaga aaggtctgtg gtaggaatat   1920
tagggtgtgt gtgtgtgtgt aggggggcaa ggaagcagtg taggggagaa aaggatgatc   1980
actctaaact gtgggaagag acacctcctc cttctcccat caggaggagt gggccttgat   2040
tgggatggga tattggagta atatgggga gaaccctgtt gtggtagggg gaattgggat    2100
atggtacagg gagactacct ggaaggctgg ttcctaatat ggaggacctg aaataggaa    2160
gcggtcttgg catgatatgg agagggtccc ctaggaaaat cgtgccctgg tggatgagaa   2220
tgctgtagag ataggactct gttctataga ggttctcaga taactttggt gtggttggga   2280
ggtcccaag gacgctgatg tggttttagg gctgcagagg actctgctgt ggtttgggag    2340
gggaagactc atgtggtttg ggaatcctag agttctctgg gttgagggaa tctactgaga   2400
aggatagatc ttaaagtatt ggccctggct gtgctacggg ctgagatcct gatgttcagg   2460
gaagactaca gaaagtggca tcttgtgtta ggggccctgg ggagggccac gagtagtgag   2520
aaaagaatga agcctactcc tctgcatact gtctgtggtt tcttttttct tttcctcctc   2580
tgaattattg gtgtcttcct gtcctccttt ccctgtgatg gctcatatcg acccctgctt   2640
ggcccccaat cattgtcttt tatgtgttct ctttgtgctg ccttaatcat ttacttgatc   2700
attatttgtc gagggactgc tgtgccatcc cccccacct ggctaccact tctctgcccc    2760
ttctcttcat tgctatctgc tgctccgttg tgcccttttc ctcttctctc tgtgccctgt   2820
ctttctcatg tccactcttc cccgcctggc actattcaca tatcccctg ttccatgttg    2880
ttttcccact tcctgtctgc tctcaggtct cagcggcggt ggcagccgag gtgcaggatg   2940
caagaaggcg ccccccggcc gggctcccgc tccaggcctc gctcccctgc ggccctctga   3000
gcccaccatg gccgtcccac cgggccatgg tcccttctct ggcttcccag ggccccagga   3060
gcacacgcag gtacgcgttc agctggctcc tcacctgcgt ggtggtaggg ggaggctggg   3120
gatagaaagg tctccagacc aaaaggtagt gtggttgccc aagacattct tctgggcaca   3180
taatgggtcc catgggattg gaaaataaca gaggagtttt caggcagagt cagggtttgg   3240
```

```
agaggctggg ttcaaatcct gacccagtgg ttaaattcct taggttctcc atacttgagt    3300
tggagaactc aactcattct gtgaaatggg gccaataatg atacctactt cacaggttg     3360 ttgtgaggat taaatgagtt aatggtatgc atgtaaaaca cttagaatgg tgcctggcac    3420
atagtaaata cccaataaat gctactaaga aaagttcaga gtgaaagatc tggattgggt    3480
gaatttggag gggggttgag tctaaagggt cttgaggcca acaggcatgg gtggtgaggg    3540
caaagctctc ccaaggctag aggcagtgaa ggcagtgaca tgcagagctt gaagcaggat    3600
gaagtgggag gtccaggggc cagatccaga tccaagagcc ttggggtgaa agaactgtgc    3660
aaagagttgg tgggagtatg ggttgaggcc caagggatga gggtaaattg agatagaggt    3720
acttcagagg gtacccaaaa tggctggctt caaagtgaag aatggggagg aacagagccc    3780
aggttttcca tatgatctct ccctctgagg ttcagaaagg agtaaaggtg aggggtgaaa    3840
ggtcagagtt cactcattca caccacagat ctctaagagc atccattgtg tgccaggccc    3900
tgctgtaggc actggaggta tagtaagaac aagagaaagt ctcagccctg ggggagtttc    3960
tttcctagac aggtggaaca aatacagaca gcaaccaaat acatgatgtg ccagcagccc    4020
ttacagttct tcctcttgag gtcggaggtg aaggcacgtc ctcagtgccc accctcacc     4080 ctgccctgca ggtattgcct gatgtgcggc tactgcctcg gaggctgccc ctggccttcc    4140
gggatgcaac ctcagccccg ctgcgtaagc tctctgtgga cctcatcaag acctacaagc    4200
acatcaatga ggtgggcagg ggctggggga tcctgggctg ggtgccgagg gtcttgtctg    4260
ctggcatgag tcactcacca gtccccatct cctggctggc tggctgggca ggtatactat    4320
gcgaagaaga agcggcgggc ccagcaggcg ccacccagg attcgagcaa caagaaggag    4380
aagaaggtcc tgaaccatgg ttatgatgac acaaccatg actacatcgt gcgcagtggc    4440
gagcgctggg tggagcgcta cgaaattgac tcgctcattg gcaaaggctc ctttggccag    4500
gtgtgggaca ccccccacca ccctgatcca aggccccact aacattgatc acacacccag    4560
tggttcagtg gcttcaagtc ccatgctggg ccactcaccc tagcccactt agtttccctg    4620
tgcctcagtc gccttttctg taaaacagtt taaataacaa gactcaacat aaggtcgtta    4680
tgttatttca catccagtgt ttacaccagc gcctgactaa tggtgcgcac tcagctgcga    4740
agtatgcata gtgttcttgg tgggtctcct tgcctggagg gagaagaatg gtgcctggct    4800
ctgccctgct cccacccctt tcttcgtgac atgcccctgcc caacaggtg gtgaaagcct    4860 atgatcatca gacccaggag cttgtggcca tcaagatcat caagaacaaa aaggctttcc    4920
tgaaccaggc ccagattgag ctgcggctgc tggagctgat gaaccagcat gacacggaga    4980
tgaagtacta tataggtgag gcctgggact ggcagggctg tgggcacctg ggatagcggg    5040
agctggagcc agtagggatg ggtcacaccc ccgccctact ctcaggagga ggctgatgtc    5100
ttcagagcag ggtttggtct gtgcttctct gacatcagtg attctcctgc tgcttttatg    5160
atttttgtcc tattttcttg gtaatggtca gaggttactg agtgctcacc aagggccagg    5220
ctctcttgga agcacttgga agttaactca ccacagccca taaggggaag gcattatta    5280 acaacatctt gaagataaga aacctgggct tccatcctag tttcttcttc aataaaacaa    5340
acaaaacggg ctgggcacag tggctcacgc ctgtaatccc agcactttg gaggccgagg    5400 tgggcggatc atgatatcaa gagatcgaga ccatcctggc caacatggtg aaaccccgtc    5460
tctactaaaa atgtgaaaaa attagcttga tgtggtggtg cgcgcctgta gtcccagcta    5520
ctcaggaggc tgaggcagga gaatcgcttg aacctgggag gcggaggtta cagtgagctg    5580
ggaccacgcc actgcactcc agcctgatga cagagcgaga ctccatctca aaaaaaaaa    5640
```

```
aacccaaaac aaacaaaaaa ccaaacctaa taacaacaac aacagttaca acaacaacaa      5700
aaaaaaacga agaaggaaa aaagaaactc aggcattcaa gtgctgtcac ttgcatgagg       5760
tggcagtttg tactaattga gctataattt gatgaggtcg tggactccag agctgttact      5820
cttaacatct gtgccagtct ttctcctccc ttaaactgat tcctgctcat ggacataaac      5880
atcacaacat aatcataaac agcaagtgga ttttaaaatg gtttcgtttg aaggaaaac      5940 gtatatcctt aaagtaaacg gaaaccagt gtcctttgcc acaaaatga atacaaggga       6000 gatgaaagca gtgttatgaa attaaatgag gaagtgtaga atgtgttaga gctagtagta     6060
actaatgaaa ctttctcttt ggtttaattg gaggtttga cagagacttg gaaagagcat      6120
taacttcctg tgtgaatcta gttgttagat aaaagatt tgactagcag atggtacccg       6180
tggggacagc acaatgtggc tagtaatcaa agagcgttgt atgacccag gccaccacct      6240 gccctctctg agccgtttct tctctggccc atttcctccc ctccccgca gtacacctga      6300 agcggcactt catgttccgg aaccaccgt gcctggtatt tgagctgctg tcctacaacc      6360
tgtacgacct cctgcgcaac acccacttcc gcggcgtctc gctgaacctg acccggaagc     6420
tggcgcagca gctctgcacg gcactgctct ttctggccac gcctgagctc agcatcattc     6480
actgcgacct caagcccgaa aacatcttgc tgtgcaaccc caagcgcagc gccatcaaga     6540
ttgtggactt cggcagctcc tgccagcttg ccagagggt aggggcggc ccggtcctgg       6600 gagcacggct agtagtttgg gtggggcaga gccaacggga ggcttagggg cggggcttgg     6660
ctgggatggg attattagga gccgtgggaa ctgagggata atgcttgggg tgggtgtg       6720 aatatactgc ccactaggat gggaagggtg aagcctgagg ggcagggccc attttgaagc     6780
tgccagatgt gaacagggtg aagttgggtt gggtttgagc cagggtgct gcctcgctaa      6840 gttttgtct tctctgttct taaagctgag gatggaggtg gaaggcttca actttgcagc      6900
tctgtatgag ctgccactaa aagtgacgat ggtatagggc ttatggaatg tcagcctctg     6960
cctggtgacc cagaagggcc caggatccgg gttggggtg gagatcaggg tctgtctagg      7020
ccagcagact ccccagattg ataaacaaga tggcaccagt ggctcccaga aaattggtgc     7080
tgataatggc aggatttgga gcctcagtcc ccattttgtc agcaagaagc ctgtcctcag     7140
ttgggtcctc ttagctttgg gggtgtcagt gggaccagta ggggaggctg ggtcccttga     7200
cgattaccct tttcccagat ctaccagtat atccagagcc gcttctaccg ctcacctgag     7260
gtgctcctgg gcacacccta cgacctggcc attgacatgt ggtccctggg ctgcatcctt     7320
gtggagatgc acaccggaga gccctcttc agtggctcca atgaggtgtg cccccaggaa     7380
ggggtgtgct ggaggtggag ggggtggagc ctggctggcc tgatgacctt gaccctgcc     7440 tgctcacagg tcgaccagat gaaccgcatt gtggaggtgc tgggcatccc accggccgcc    7500
atgctggacc aggcgcccaa ggctcgcaag tactttgaac ggctgcctgg ggtggctgg     7560 acctacgaa ggacgaaaga actcaggaag gtgcggcccc tgcccatgc cactcctccc     7620 accccgtggc ccctcactca cacttggggc tctctccccc tgctccctct cccttgtgtc    7680
tttcccttcc ttccactccc ccttgtctgt cctttccttc ctccctgcc cacccatct      7740 cccatctctc cttcccaccc cacaactctt cttagctttt ctttccactt tctctcttgt    7800
gcctctgttt cccgtgtgt gtctccctgc cctcctgcc cactgacggc cactctcttg     7860
ccccccctcc cacccctcc ctgccaggat taccagggcc ccgggacacg gcggctgcag    7920
gaggtgctgg gcgtgcagac gggcgggccc ggggccggc gggcggggga gccgggccac    7980
```

```
agccccgccg actacctccg cttccaggac ctggtgctgc gcatgctgga gtatgagccc      8040
gccgcccgca tcagccccct gggggctctg cagcacggct tcttccgccg cacgccgac       8100 gaggccacca cacgggccc ggcaggcagc agtgcctcca cctcgcccgc gcccctcgac       8160
acctgcccct cttccagcac cgccagctcc atctccagtt ctggtgggtg cccaggtgcc      8220
caaatggggt acaacgggtg ggggctgctc aggtttggcc tgtcctgggg gacctggtta     8280
ctgggtcttc acacaaagcg ccgaaactga tcctgaactg taagatgacg tgtgggatgg     8340
gagagctcca actggccctg acacaatcac tgaaattggg ctcagagccc tgaaactggt     8400
tctgactcta aaacccaaaa ctgaattcca acccagaatc tcagaattgg cccggtgct     8460 tcagatgggc tctgctcttg aagcctgaac ctgagcctgg gccgtgacct tccctcagcc     8520
atcccaaaac ccactcgcca ccttctctca ccttatgccc cttcacctct cctccctggc     8580
acttccagga ggctccagtg gctcctccag tgacaaccgg acctaccgct acagcaaccg     8640
atattgtggg ggccctgggc cccctatcac agactgtgag atgaacagcc ccaggtaat     8700 gggggctttgg gggctttgga ggtgggtggt ggtgcctggg gcttagagac cagggtctcc     8760
atcacccatg gctcctttgc tttttttaggt cccaccctcc cagccgctgc ggccctgggc    8820
agggggtgat gtgcccccaca agacacatca agccctgcc tctgcctcgt cactgcctgg     8880
gaccggggcc cagttacccc cccagccccg ataccttggt cgtccccat caccaacctc      8940 accaccaccc ccggagctga tggatgtgag cctggtgggc ggccctgctg actgctcccc    9000
acctcaccca gcgcctgccc ccagcaccc ggctgcctca gccctccgga ctcggatgac     9060
tggaggtcgt ccacccctcc cgcctcctga tgacctgcc actctgggc ctcacctggg      9120 cctccgtggt gtacccccaga gcacagcagc cagctcgtga ccctgccccc tcctggggc    9180 ccctcctgaa gccataccct ccccccatctg ggggccctgg gctcccatcc tcatctctct    9240
ccttgactgg aattgctgct acccagctgg ggtgggtgag gcctgcactg attggggcct    9300
ggggcagggg ggtcaaggag agggttttgg ccgctccctc cccactaagg actgaccct     9360 tgggcccctc tccccctttt tttctatta tgtaccaaa acagtggtg gtccggtgga       9420 gggaagaccc ccctcaccc caggacccta ggagggggtg ggggcaggta gggggagatg      9480
gccttgctcc tcctcgctgt acccccagta aagagcttc tcacatgcct gcctgagcgt     9540
ttgcagggcc tcggctcccc tcacccgacc ctcagaggca tggtgggga ggggttgc     9600 ggagggggtg ctggaggagc tctggtgtgg agacgtctcg tggggaagct gtggcgcgtg    9660
ttgcaggcat gagtctgcag gtctggggca tcagcattct agatagatcg tggacaggat    9720
cctggcctac atttgccttt tcctgggtaa atagaccctg aaagggtaaa ggttcagctc    9780
tggcctgtct ctgggaaaca ggtgcctaa taagccgggg cgtccgcaga cttagcacaa     9840
gagtggctcc tcatgccaag caggcgtcca gtagcagctg agtacactta ggaggctttg    9900
ttggtgccat ctggggaaca ggcagacaat aggtacagac tctgtcccca cgtgtactgt    9960
ccagctcttt ggaatcatcg cgaaacaaag agttttgaga t                         10001
```

<210> SEQ ID NO 3
<211> LENGTH: 2588
<212> TYPE: DNA
<213> ORGANISM: Homo sapiens

<400> SEQUENCE: 3

```
agtgtgggtc acgtgagggg agcggagagg gagggatggg ggcggagtcc agggcgtggg      60
ggggccggtt tgttgtggtc gccatttgc tggttgcatt actgggtaat cggggccctg     120
```

```
gcttgccgcg tccgccggat accctcagcc agtgggcagg tctgagctcg ggctccccga    180
gcagtttgag tccccttgcc cgctccttca ggtctcagcg gcggtggcag ccgaggtgca    240
ggatgcaaga aggcgccccc cggccgggct cccgctccag gcctcgctcc cctgcggccc    300
tctgagccca ccatggccgt cccaccgggc catggtccct tctctggctt cccagggccc    360
caggagcaca cgcaggtatt gcctgatgtg cggctactgc ctcggaggct gcccctggcc    420
ttccgggatg caacctcagc cccgctgcgt aagctctctg tggacctcat caagacctac    480
aagcacatca tgaggtata ctatgcgaag aagaagcggc gggcccagca ggcgccaccc     540
caggattcga gcaacaagaa ggagaagaag gtcctgaacc atggttatga tgacgacaac    600
catgactaca tcgtgcgcag tggcgagcgc tggctggagc gctacgaaat tgactcgctc    660
attggcaaag gctcctttgg ccaggtggtg aaagcctatg atcatcagac ccaggagctt    720
gtggccatca agatcatcaa gaacaaaaag gctttcctga accaggccca gattgagctg    780
cggctgctgg agctgatgaa ccagcatgac acggagatga agtactatat agtacacctg    840
aagcggcact tcatgttccg gaaccacctg tgcctggtat ttgagctgct gtcctacaac    900
ctgtacgacc tcctgcgcaa cacccacttc gcggcgtct cgctgaacct gacccggaag     960
ctggcgcagc agctctgcac ggcactgctc tttctggcca cgcctgagct cagcatcatt   1020
cactgcgacc tcaagcccga aaacatcttg ctgtgcaacc ccaagcgcag cgccatcaag   1080
attgtggact tcggcagctc ctgccagctt ggccagagga tctaccagta tatccagagc   1140
cgcttctacc gctcacctga ggtgctcctg ggcacaccct acgacctggc cattgacatg   1200
tggtccctgg gctgcatcct tgtggagatg cacaccggag agcccctctt cagtggctcc   1260
aatgaggtcg accagatgaa ccgcattgtg gaggtgctgg gcatcccacc ggccgccatg   1320
ctggaccagg cgcccaaggc tcgcaagtac tttgaacggc tgcctggggg tggctggacc   1380
ctacgaagga cgaaagaact caggaaggat taccagggcc ccgggacacg gcggctgcag   1440
gaggtgctgg gcgtgcagac gggcgggccc gggggccggc gggcggggga gccgggccac   1500
agccccgccg actacctccg cttccaggac ctggtgctgc gcatgctgga gtatgagccc   1560
gccgcccgca tcagcccct ggggctctg cagcacggct tcttccgccg cacggccgac    1620
gaggccacca acacgggccc ggcaggcagc agtgcctcca cctcgcccgc gcccctcgac   1680
acctgccccct cttccagcac cgccagctcc atctccagtt ctggaggctc cagtggctcc   1740
tccagtgaca accggaccta ccgctacagc aaccgatatt gtgggggccc tgggcccct    1800
atcacagact gtgagatgaa cagccccag gtcccaccct cccagccgct gcggccctgg   1860
gcaggggtg atgtgccca caagacacat caagcccctg cctctgcctc gtcactgcct   1920
gggaccgggg cccagttacc ccccagccc cgataccttg gtcgtccccc atcaccaacc   1980
tcaccaccac ccccggagct gatggatgtg agcctggtgg gcggccctgc tgactgctcc   2040
ccacctcacc cagcgcctgc cccccagcac ccggctgcct cagccctccg gactcggatg   2100
actggaggtc gtccacccct cccgcctcct gatgaccctg ccactctggg gcctcacctg   2160
ggcctccgtg gtgtacccca gagcacagca gccagctcgt gacctgccc cctccctggg   2220
gcccctcctg aagccatacc ctcccccatc tgggggcccc gggctccat cctcatctct    2280
ctccttgact ggaattgctg ctacccagct ggggtgggtg aggcctgcac tgattgggc    2340
ctggggcagg gggtcaagg agagggttt ggccgctccc tccccactaa ggactggacc    2400
cttgggcccc tctccccctt tttttctatt tattgtacca aagacagtgg tggtccggtg   2460
```

```
gagggaagac cccccctcac cccaggaccc taggaggggg tgggggcagg taggggggaga    2520 tggccttgct cctcctcgct gtaccccccag taaagagctt tctcacatgc aaaaaaaaaa    2580
aaaaaaaa                                                              2588

<210> SEQ ID NO 4
<211> LENGTH: 2468
<212> TYPE: DNA
<213> ORGANISM: Homo sapiens

<400> SEQUENCE: 4
agtgtgggtc acgtgagggg agcggagagg gagggatggg ggcggagtcc agggcgtggg      60
ggggccggtt tgttgtggtc gccattttgc tggttgcatt actgggtaat cggggccctg     120
gcttgccgcg tccgccggat accctcagcc agtgggcagg tctgagctcg ggctccccga     180
gcagtttgag tccccttgcc cgctccttca ggtctcagcg gcggtggcag ccgaggtgca     240
ggatgcaaga aggcgccccc cggccgggct cccgctccag gcctcgctcc cctgcggccc     300
tctgagccca ccatggccgt cccaccgggc catggtccct tctctggctt cccagggccc     360
caggagcaca cgcaggtatt gcctgatgtg cggctactgc ctcggaggct gcccctggcc     420
ttccgggatg caacctcagc cccgctgcgt aagctctctg tggacctcat caagacctac     480
aagcacatca atgaggtata ctatgcgaag aagaagcggc gggcccagca ggcgccaccc     540
caggattcga gcaacaagaa ggagaagaag gtcctgaacc atggttatga tgacgacaac     600
catgactaca tcgtgcgcag tggcgagcgc tggctggagc gctacgaaat tgactcgctc     660
attggcaaag ctcctttgg ccaggtggtg aaagcctatg atcatcagac ccaggagctt     720
gtggccatca agatcatcaa gaacaaaaag ctttcctga ccaggcccca gattgagctg     780
cggctgctgg agctgatgaa ccagcatgac acggagatga agtactatat agtacacctg     840
aagcggcact tcatgttccg gaaccacctg tgcctggtat ttgagctgct gtcctacaac     900
ctgtacgacc tcctgcgcaa cacccacttc cgcggcgtct cgctgaacct gacccggaag     960
ctggcgcagc agctctgcac ggcactgctc tttctggcca cgcctgagct cagcatcatt    1020
cactgcgacc tcaagcccga aaacatcttg ctgtgcaacc ccaagcgcag cgccatcaag    1080
attgtggact tcggcagctc ctgccagctt ggccagagga tctaccagta tatccagagc    1140
cgcttctacc gctcacctga ggtgctcctg ggcacaccct acgacctggc cattgacatg    1200
tggtccctgg gctgcatcct tgtggagatg cacaccggag agcccctctt cagtggctcc    1260
aatgaggtcg accagatgaa ccgcattgtg gaggtgctgg gcatcccacc ggccgccatg    1320
ctggaccagg cgcccaaggc tcgcaagtac tttgaacggc tgcctggggg tggctggacc    1380
ctacgaagga cgaaagaact caggaaggac ctggtgctgc gcatgctgga gtatgagccc    1440
gccgccgcca tcagcccct gggggctctg cagcacggct tcttccgccg cacggccgac    1500
gaggccacca acacgggccc ggcaggcagc agtgcctcca cctcgcccgc gcccctcgac    1560 acctgccccct cttccagcac cgccagctcc atctccagtt ctggaggctc cagtggctcc    1620
tccagtgaca accggaccta ccgctacagc aaccgatatt gtgggggccc tgggcccct     1680 atcacagact gtgagatgaa cagccccccag gtcccaccct cccagccgct gcggccctgg    1740
gcagggggtg atgtgcccca aagacacat caagcccctg cctctgcctc gtcactgcct    1800
ggaccggggg cccagttacc cccccagccc cgatacctty gtcgtccccc atcaccaacc    1860
tcaccaccac ccccggagct gatggatgtg agcctggtgg gcggccctgc tgactgctcc    1920
ccacctcacc cagcgcctgc cccccagcac ccggctgcct cagccctccg gactcggatg    1980
```

| | |
|---|---|
| actggaggtc gtccacccct cccgcctcct gatgaccctg ccactctggg gcctcacctg | 2040 |
| ggcctccgtg gtgtacccca gagcacagca gccagctcgt gaccctgccc cctccctggg | 2100 |
| gcccctcctg aagccatacc ctcccccatc tggggccct gggctccat cctcatctct | 2160 |
| ctccttgact ggaattgctg ctacccagct ggggtgggtg aggcctgcac tgattggggc | 2220 |
| ctggggcagg ggggtcaagg agagggtttt ggccgctccc tccccactaa ggactggacc | 2280 |
| cttgggcccc tctccccctt tttttctatt tattgtacca aagacagtgg tggtccggtg | 2340 |
| gagggaagac cccccctcac cccaggaccc taggaggggg tggggcagg taggggaga | 2400 |
| tggccttgct cctcctcgct gtaccccag taaagagctt tctcacatgc aaaaaaaaaa | 2460 |
| aaaaaaaa | 2468 |

<210> SEQ ID NO 5
<211> LENGTH: 2504
<212> TYPE: DNA
<213> ORGANISM: Homo sapiens

<400> SEQUENCE: 5

| | |
|---|---|
| agtgtgggtc acgtgagggg agcggagagg gagggatggg ggcggagtcc agggcgtggg | 60 |
| ggggccggtt tgttgtggtc gccattttgc tggttgcatt actgggtaat cggggccctg | 120 |
| gcttgccgcg tccgccggat accctcagcc agtgggcagg tctgagctcg gctccccga | 180 |
| gcagtttgag tccccttgcc cgctccttca ggtctcagcg gcggtggcag ccgaggtgca | 240 |
| ggatgcaaga aggcgccccc cggccgggct cccgctccag gcctcgctcc cctgcggccc | 300 |
| tctgagccca ccatggccgt cccaccgggc catggtccct tctctggctt cccagggccc | 360 |
| caggagcaca cgcaggtatt gcctgatgtg cggctactgc ctcggaggct gccctggcc | 420 |
| ttccgggatg caacctcagc cccgctgcgt aagctctctg tggacctcat caagacctac | 480 |
| aagcacatca tgaggtata ctatgcgaag aagaagcggc gggcccagca ggcgccaccc | 540 |
| caggattcga gcaacaagaa ggagaagaag gtcctgaacc atggttatga tgacgacaac | 600 |
| catgactaca tcgtgcgcag tggcgagcgc tggctggagc gctacgaaat tgactcgctc | 660 |
| attggcaaag gctcctttgg ccaggtggtg aaagcctatg atcatcagac caggagctt | 720 |
| gtggccatca agatcatcaa gaacaaaaag gctttcctga accaggccca gattgagctg | 780 |
| cggctgctgg agctgatgaa ccagcatgac acggagatga agtactatat agtacacctg | 840 |
| aagcggcact tcatgttccg gaaccacctg tgcctggtat ttgagctgct gtcctacaac | 900 |
| ctgtacgacc tcctgcgcaa cacccacttc cgcggcgtct cgctgaacct gacccggaag | 960 |
| ctggcgcagc agctctgcac ggcactgctc tttctggcca cgcctgagct cagcatcatt | 1020 |
| cactgcgacc tcaagcccga aaacatcttg ctgtgcaacc caagcgcag cgccatcaag | 1080 |
| attgtggact tcggcagctc ctgccagctt ggccagagga tctaccagta tatccagagc | 1140 |
| cgcttctacc gctcacctga ggtgctcctg ggcacaccct acgacctggc cattgacatg | 1200 |
| tggtccctgg gctgcatcct tgtggagatg cacaccggag agcccctctt cagtggctcc | 1260 |
| aatgaggtcg accagatgaa ccgcattgtg gaggtgctgg catcccacc ggccgccatg | 1320 |
| ctggaccagg cgcccaaggc tcgcaagtac tttgaacggc tgcctgggg tggctggacc | 1380 |
| ctacgaagga cgaaagaact caggaaggat taccagggcc ccgggacacg gcggctgcag | 1440 |
| gaggacctgg tgctgcgcat gctggagtat gagcccgccg cccgcatcag cccccctggg | 1500 |
| gctctgcagc acggcttctt ccgccgcacg gccgacgagg ccaccaacac gggcccggca | 1560 |

| | |
|---|---|
| ggcagcagtg cctccacctc gcccgcgccc ctcgacacct gccctcttc cagcaccgcc | 1620 |
| agctccatct ccagttctgg aggctccagt ggctcctcca gtgacaaccg gacctaccgc | 1680 |
| tacagcaacc gatattgtgg gggccctggg cccctatca cagactgtga gatgaacagc | 1740 |
| ccccaggtcc caccctccca gccgctgcgg ccctgggcag ggggtgatgt gccccacaag | 1800 |
| acacatcaag cccctgcctc tgcctcgtca ctgcctggga ccggggccca gttacccccc | 1860 |
| cagcccgat accttggtcg tccccatca ccaacctcac caccacccc ggagctgatg | 1920 |
| gatgtgagcc tggtgggcgg ccctgctgac tgctccccac ctcacccagc gcctgccccc | 1980 |
| cagcacccgg ctgcctcagc cctccggact cggatgactg gaggtcgtcc acccctcccg | 2040 |
| cctcctgatg accctgccac tctggggcct cacctgggcc tccgtggtgt accccagagc | 2100 |
| acagcagcca gctcgtgacc ctgcccctc cctgggccc ctcctgaagc catacccctcc | 2160 |
| cccatctggg ggccctgggc tcccatcctc atctctctcc ttgactggaa ttgctgctac | 2220 |
| ccagctgggg tgggtgaggc ctgcactgat tggggcctgg ggcagggggg tcaaggagag | 2280 |
| ggttttggcc gctccctccc cactaaggac tggacccttg ggccctctc ccctttttt | 2340 |
| tctatttatt gtaccaaaga cagtggtggt ccggtggagg aagaccccc cctcacccca | 2400 |
| ggaccctagg aggggtggg ggcaggtagg gggagatgc cttgctcctc ctcgctgtac | 2460 |
| ccccagtaaa gagctttctc acatgcaaaa aaaaaaaaa aaaa | 2504 |

<210> SEQ ID NO 6
<211> LENGTH: 11001
<212> TYPE: DNA
<213> ORGANISM: Mus musculus

<400> SEQUENCE: 6

| | |
|---|---|
| acaacaggag tggatgagtg atgtgacttt cgtgttctgg atccaccttt ggggtgcttt | 60 |
| ggagggaggc tgtgtggtgg ggggtaagac tggaggcaag agagtcccag gaacctggtg | 120 |
| gtgaaggagc acaggccctg ttgggaggct ctggggagct ctctgctgcc ttgtttgtag | 180 |
| taaccgctgt cccttttttc cttagcaatg gtggatgtca tctttgccga tgtggcccag | 240 |
| ccagaccaaa cccgaattgt ggccctgaac gcccacacct tcctgcggaa tggaggacac | 300 |
| tttgtgattt ccattaaggt atgggtcttg ccatgtaagg ttgagtaacc ctagagtgtg | 360 |
| gtgtgggtgc tttgtctctg tggctgagca ggttatggcg ccttagccta tctgacttgt | 420 |
| ttattagtcc tccttatggc tgaaataaag actgatagct gctaagcatt tggagcagat | 480 |
| tgtggggtac aatattaact gcagcaggta catttttcaa acatttttaa ttttaaatag | 540 |
| ggaaaactct cgcgcatcct caccatgttc aaaactggcc aacctattgc tacacttgtt | 600 |
| tttgggtttt ttttttgttt tgttttgttt ttgttttttc aagacagagt tttctctgta | 660 |
| tagccctggc tgtcctggaa ctcaactctg tagaccaggc tgctattgct acatttgttc | 720 |
| tgtttttgcc agctgggctt ccaggatatg aagaaaatt cctgacctta aacactgcct | 780 |
| tagataaatg aaataacctg tttccaatgt gagccaaatt aaaacttctt taatgaagtt | 840 |
| agaaaattgg gaaagcctgg gtctccaaat ctgtaactta gtcctgactc ctttctaggc | 900 |
| caactgcatt gactccactg cgtcagcaga ggctgtgttt gcatctgaag tgaagaagat | 960 |
| gcagcaggag aacatgaagc cgcaggagca gctgacgcta gagccttatg agcgagacca | 1020 |
| cgccgtggtt gtcggtgtgt acaggtgagt gtcacaacag acctctccct tacctgtggc | 1080 |
| cctgagaagc caaagtggt tacaactcga ccccctctga tttcctcaca ggccacctcc | 1140 |
| caaggtgaag aactgaaact cagagctgtc tggattgaag agatgtgtgt tgttactgtt | 1200 |

```
gcacgtgtgg cttgtgattt tttgggggcg ggggagttgt tttgttttc tattaaaaga    1260 ctcatctgtc tccctgtct ggtgcctatt gctaagtggc ctcgagacgc atgcgccctt     1320
gatcaacttt gtgtgcttcg gggggtggtg cctggaaagt ttcatccggt cacatggtgc    1380
atgctccatt ggtggctgct ccgcacgtgc gcggctcagc acccttaagg cgcaggcgca    1440
ctgtgctccg ctaggtcacg tgaatgatgt ggggcggag ccggggcagg ggggccggtt     1500
tgttgtggtc gccattttgc tggttgcatt actgggtaat cggggccctg gctcgccgcg    1560
tccaccggac accctcagcc agtgggcagg tctgagctcg ggctccccga gcagtttgaa    1620
tccccttacc cacgccctca ggtaagggtg ctgcgacggg cggggcggca cgcttgggtg    1680 ggggcaggc cggaaccgc cctgcccgtc cccgcgagat ttagcaaggg aaaggagggg      1740
gctttgggcc gttgcagcgg agtccggctc ttcatagctg gattcctgga agaggctgag    1800
cccgagggag ccgtcctgag agggagtcgg ggaggggca gccaggcccc actcccgccc     1860
tttgtttggg ctcggctgcg ctggccgctt cgctgtcgcc tagcaacagc tgccctgagt    1920
gctaattggt taagctcttg gcagcaacaa ccaatggcgc ggttgttgcc atgggaggtg    1980
cggcctgccg ggctctcttg ggcccgccc gcgggactc cactggccgg ggcgggcctg      2040
ccgggtgggg ggcgggacgc cagggtccct ggggcgggt ggccacgcgg ggcggggctg     2100
ggccgtaggc cgagggttaa cccgcccctc ccccgtccac ctgctgtccc cttccccgc     2160 gtgccctggt ctgaccctcg tcccctcctt tccccgcccc tcccctcgg tggcagtggc     2220 ggcggctgct gttgtcaccc accggccgc ctgtcccgct tgccctcacc gccgcgggc      2280 tggctaggct agccgggccg gggacaggcg gccacctcct catcgccgcc gccaccacca    2340
ccgccgccat gctggccgct cgcccaccgc actggggtcc ccatcgcgct ccagccccc     2400 gtgggcccag cgccatccct gacccgggta ggggtgggag ctgtaagagc tggtcctagt    2460
gtgggagggc tcgggaagag gttgtttatc tgtgaagccc caataaaggg gacctggagt    2520
ggcaagacat agcatagaag gggatctgac aaggggagg ctcctaagaa ggggattttg     2580
ttccgaagga cacttttagt gagtgaagtc ttgtgcgata tttagggatt tggctgtcag    2640
gcccttctag gaataggctc aattgtggaa tgacccagcg tagaaataga ggagctagca    2700
aggacctcag ggtaaagaag aaaaagaccg tgactcttag atgttgaaaa atgacacctc    2760
tcccttgttt tcctgaggag taggggtctt ggagtaatgg gggaatccta gtgggataaa    2820
tatagactgc ttaaaagaag gatctctggt tccagagacc tcatataggg agcagggagc    2880
ggtcttggag tatggagtcg gtcccagggg aaagtgccga ggtggttgaa acatctatag    2940
cttgcatgta aaggagttct cagataacct tgggtttgct gggaggtcca taaggactgc    3000
tatgttcttt agaatagaaa gaaactagtg ggtagactgg gcttgaaatt gggcccttgg    3060
tgttgaggga agacggtgtg agggcgggc cttatctgag ggactcaggc tggccaccag     3120
taaaattttg aaggactgag ttctactgcc cagactctac acggtttctg ccttcttttg    3180
ctctcctaat tcctggcctc tttctatccc tcctgccctg gccttgtacc caccctctcc    3240
cacccctgtc tggctctgat ggctcccttt tacatctctg gatgtgatgc ttcattcatt    3300
ttttttggct cctcatttgt tgagagacac gctgtgctaa cccacttgct acccttctg     3360 tttgtacatg gctacctggt gctggtgctc tgccctgtcc cctgtctccc cctggtcctg    3420
cccctaactc atacccacct cttctgactg accctgacct acatgccttc ttgttccatg    3480
ttgtcttccc acttcctacc tgctctcagg tctcagcggc ggtggcagcc gaggtgcagg    3540
```

-continued

```
atgcgagaag gcgcccccg gccgggctcc cgctccaggc ctcacgcccc tgcggccctc      3600
tgagcccacc atggccgtcc caccaggcca tggtcctttc tctggctttc cggggcccca      3660
ggaacacaca caggtaggca ttcagctggc ttctcacctg cctgaggatt gaagggtctc      3720
cagacaagag catgattgtt ggaggatctc tggggacttt ggaggcctca cagtccaccc      3780
tcattcctgc tgaggacgga atccttgagc ttctccgtgg cctgccctct cacagcatgg      3840
ttttgaagtg taatgtgtgt cttgggtcag aactgtcact ggcacagagc agacaggaac      3900
acaggtctga aggttcacaa caagaacgag gtctggagta aggggcatga gagagatgtc      3960 gagggggtg gaaatgagaa taagctgaga ccagggagac taacccagtc caggagcttt      4020
gtaactgggc agaaacactc acttgagagt gaggacatgg atacagggaa ttcattggca      4080
tggttcccca taatggtggt ctcaggtgca aagattcagg ggtaaacacc cagatatgga      4140
gcaaaagagc tgacctgggg cagaatggaa ggccagaggt aaatcactca tttcacataa      4200 tgaacgatg aatggggagc ccacacagtg tgcttgtgct ctacaggtgg gatcggagct      4260
agagaaatgt aggcatggtc agtgagtcgt cagctttccc attctctccc tggaagttga      4320
ggtgaaggct tgtgctcagc atctgctccg ctctaccaca ggtactacct gatgtgcggc      4380
tcctgccccg gagactgccc ctggccttcc gggatgcggc ctcagcccg ctgcgcaagc       4440 tctcggtgga cctcatcaag acctacaagc acatcaatga ggtaaagcgg ggaatggact      4500
tccctggttg ggtgttgcaa agggtcctgg cttcttgccc gggtcactta agggtccggt      4560
ttcctggctg cctgagcagg tatactatgc gaagaagaag cggcgggccc aacaggcgcc      4620
accccaggac tcgagcacca aaaggagaa aaggtcctg aaccacggtt atgatgacga       4680
caaccacgac tacattgtgc gcagtggcga gcgctggcta gagcgctatg agattgactc      4740
tcttattggc aaaggctcct ttggccaggt gtgggactcc ccactcatcc agtatctgga      4800
tgcagacaac cactaacatt cccaacattc cctcctcccc gagtggttca ctggttcact      4860
tgctgcaagt tctgtcctgg accagccagt caagccactt agtttccctc ttagttctgt      4920
atgagtataa atcacaaggc ttcttgtaag aaaactgtta ttttgtatcc agtataaggg      4980
atgtgagcac tgggctgtga gttgttagaa aggtgtggct ggtgggcctc ccaccttccc      5040
aggtaactct ccttgtctcg acaggtggtg aaagcctatg atcaccagac tcaggagctg      5100
gtggccatca agatcatcaa gaacaaaaag gccttcctga accaggcaca gattgagcta      5160
cggctgttgg agctgatgaa ccagcatgat acagagatga agtactacat aggtgaggcc      5220
tgggcttggg caggtgcagg gtgcctgtgg gagagagacc tccacgaggg tctttgggct      5280
tctcatcctt tgattctcct gctgtgctca ggatttctct cttgtgctca ctgagggcca      5340
gattgtgttg caaccccttg ctttgaatta cctccccgca gctggtgagg acggggcag       5400 ctctgagtac atgttggaga gactgaggca ctcagtgctc tcacatcaga ctcaacagct      5460
gaggatgtga aaagcagtgg cctctagagc tctggctctt gagatatgtc ccagtcttca      5520
gttcctctgg aaagggactc tgtagaggac agccagtatc ccttggcaca tgggtagaca      5580
cagcaaagac gagagcaggc tcttttggta gttcgggttt tggtgatggt gatactttg       5640 gaggttttgc tttgctattc tggggatcga gcccagtgct ttatatgtaa taggcaaaca      5700
ggtcctcccc tcaaccatcc ccaccccaga acatctccag accttttgtt acttgactat      5760
tttgagatag ggtctcagta aatatatcca gatgaacctt gagctaacag tcttcgtgca      5820
tcagtgtaca aagacctggg tctccatgcc tacaccccag gctgattcag tgttgtcaa       5880 atgaagtgag taaatgtgga gctgttttga cgctttatta ggagggaaca gtaccttta      5940
```

```
tttcccttttg cagtgctggg gcctgaaccc tgggccttgt gcttgctagg caagcgtgct    6000
gctgcccttt ggtcatccca taatctacgc tagagtaacc ctagattata tcatcctttg    6060
gggttttgga actggaaggt gtgagagacg caagagaatt aacatgcctt ggaagtccag    6120
tgagttggtg tagaaacacc tgagggctca ctgcaggtta ccagaggtgg tcactgtgaa    6180
gtcccaagcc acctgccatc agtgtgtcta acctgttccc cactgtcacc gttgcccgca    6240
gtacacctta agcggcactt catgttccgg aatcacctgt gcctggtgtt tgagctgctg    6300
tcctacaacc tgtacgacct cctccgcaac acacactttc ggggtgtctc actgaacctg    6360
acgaggaagc tggcacagca gctctgcaca gctctgctct ttctggccac ccccgagctc    6420
agcatcatcc actgcgacct caagcctgag aacatcctgc tctgcaaccc caagcgcagt    6480
gccatcaaga tcgtggactt cggcagttcc tgccagcttg ccagcgggt gcggttctga    6540
ctgtgggcag ggccgatgtc tttggtggga tggggtggga tggcttcatt ttggccctgg    6600
aagctgatgg ccaagggatg atattgttca taggaaggcc cacctggaga gaggtggtgg    6660
gaggtgaagg ggcaaagatg acccaagcaa ggaagagaaa ggatgaagct gatggccagg    6720
ccatctcaga ggagtggagt tgtgatctga gcctcaggct gctttgctga tgctcacagg    6780
gagagtgccc tgaagcctgt ggttatactc atatagtacg gtgcatgatg ccagcctct    6840
cttaaacaag aagggccaga gctgggaatg gaggcgggtt aaggcagaaa ggccattgaa    6900
gactggaggc tcatgggcag acagtgttg gtggcttgtg caacattgct cagagcctcc    6960
cgacctagag gttccatcct gttttcaggc ggggctttg tcttcagttg attctcccag    7020
tggaaccagc aggggagctg gtgccctgac tactgtcccc tcccccagat ctaccagtat    7080
atccagagcc gcttctaccg ctcacccgag gtgctcctgg gtacacccta tgacctggcc    7140
attgacatgt ggtccctggg ctgcatcctc gtggagatgc acaccggaga gccctcttc    7200
agtggctcta atgaggtgtg cccctggaag gggtgtactg gaggtggagg ggtgagccc    7260
ggccacctgg ctcccctgac cgccgcctgc ccgtaggtgg accagatgag ccgtattgtg    7320
gaggtgttgg gcatccctcc cgcacccatg ctggaacagg cacccaaggc tcgaaagtac    7380
tttgagcggc tgcctggggg tggctggacc ctacgaagga caaaggaact caggaaggtg    7440
cggcccctgc cctgtgccac ttctccctcc ctgggtgtcc cctcactcac acttggggct    7500
cccctctccc ggtgtcattc cctgtcttcc tctcccccctt gtctgtcctt tccttcctcc    7560
cctgcccacc ccatcgccct cctaccccac agctcttgct agctttctct ccctctctct    7620
ttcttgtgcc tctgtttccc cgtgtgtgtc tccctgcccc tcctgcccac tgacggccac    7680
tctcttgccc cccctcccac cccctccctg ccaggattac cagggccctg ggacacggcg    7740
gctgcaggag gtgctgggcg tgcagacggg cgggcccggg ggccggcggg cggggagcc    7800
cggccacagc cccgccgact acctccgctt ccaggacctg tgctgcgca tgctggaata    7860
tgagcccgcc gcccgcatca gccctctggg cgctctgcag catggcttct tccgccgcac    7920
ggccgacgag gccaccaaca cgggcccggc aggcagcagt gcctccacct cgccggcgcc    7980
ccttgacacc tgcccctcct ctagcaccgc cagctccatc tccagctctg gtgggtgccc    8040
catgtcacat gtgtaccaca gggcccagcc tgggtggcct aaccactggg cctctgtcat    8100
agagccccta gaactaccag attctgaggt ggggtgggac agtcctacat gacccaacag    8160
gttctcagaa ttggggcagg agactcggtc cctagatctg actccaccct cccacacaac    8220
tctgacccta gatttcaaac ttgggctgtt gacagccgtc attcacactt gctctggtct    8280
```

```
caaagcctaa gcttggggtg gaggacagac ttgcccccat cttaccactt atgtcctctt    8340
ttctccttcc tggtgcttct aggaggttcc agtggctcct ccaacgacaa cagagcctac    8400
cgatacagca accgatattg tgggggccca gggccccca tcactgactg tgagatgaac     8460
agccccagg tactggagct gtgaaatttt ggaagagggt ggtaggtgcc taggacttga     8520
tctcactgct catgactcct ttgccttttt aggtcctacc ctcccagcct ctgcgcccct    8580
gggcagggg tgatgtgccc cacaagacac atcaagcccc tatctctgcc tcaacattgc     8640
cggggactgg ggctcagtta ccccattgc cccgttgcct tggacgaccc ccatcaccaa     8700
catcaccacc accccagag ttgatggatg tgagcctggt gggcagccct ccagactgct     8760
ctccacctcc tccagcacct gcccccagc accggctgc ctcagccctc cggactcgga     8820
tgacaggagg tcgaccacct ctcccacccc ctgatgaccc tgccactctg ggcctcgcc     8880
tgggtctcca tggtgtaccc cagagcacag cagccagctc atgaccctgc ccctccctg     8940
gggcccctcc tgaagccata ccccccata tgggggccct gggctcccat cctcatctct     9000
cccccttgact ggacttgctg ctaccagct gggggtgggtg aggcctgcac tgactggggc    9060
ccagggcagg gggtcaaggg agaggagttt ggccgcaccc tccccactaa gactggaccc    9120
ttggcccctc tcttcccct ccccccttgt tttctattta ttgtaccaaa gacagtggtg    9180
gtccggtaga ggggagattc cccccttaccc agggccctag gaggggtgg gggcaggtag    9240
gggagatgg ccttgctcct cctcgctgta ccccccagta aaaagctttc tcacatgcct    9300
gcctgagcgt ttgcagggcc ttggctccct cccctgaccc tcagaggcat ggtggggaag    9360
gttgtgtggg gaagggtgc tttgtggtgt gggtatatcc cttctgggga catcatagtt    9420
cttggtgcag gcatggggca gcaggagatt ggtgggctga gaagcctgga tacaagaatc    9480
ctggcctgtt gctaggaaat tgatggtct gccctcatcg gtcagggctt ccacagagtc    9540
cacgcagaag tggcttttt tcttttttt ttttttttt tcctgtcagg caggcattcg    9600
gtaggttgtg ggtatattca gcaggctgcc ttaggtacca tcgggggagc agacagacag    9660
tgggtacaga ttttacccaa cccgtttcca gccccactct gcagtcattt cgagtattga    9720
gattctcgag caaaaagacg ctccctgacc tccaggtaag tgatttttt gtttccatgg    9780
caatttggaa ccaactgtct cccaaccagt ttgtaagact cacttggctc tcccacaagg    9840
gagggtgtgg tgactcctgg gagatggagt tctacaaggc cagctctttg ctcactttc     9900
tttgggaact acaaagccca gaagtctctg cacacatggc tggggactgg tgttcaataa    9960
gctgtagggc attattgctt agatgttgga ggatccatag tacaggttga ttggatgctg    10020
ctggtgccca ggagtaggat gggtagggag agagagtagt cagccagcct tacagggcca    10080
agcagtggag gctccatgta gagaactctg gtgagcaaga gcctgttgtg gaaactgatg    10140
gcagtggtca tttttgagaat gccattttaag atttatcaga gatctttttgt tatctagaaa    10200
gctggacttt ttcacaggga ctgagacacc atgagaggaa ggtgcacagc ccagttttgc    10260
cacaacatgg aagtatgttg ccaggaaaag gtagcttgta gcaggcccct aggcaagatg    10320
tgacggccat gggttggggg gggtgctaag aagaccagga aagggcaggt gttttccaga    10380
cacctgaggt gaaggaagag acggagacaa gcagaggagg ggagggctcc agtatataga    10440
gcaccccagc ccctattaac agagtcttgg ttagtgtttt gttttttaat tatgtgttct    10500
cttggtgctg gggatggaat ccaggaaatc ccagatgcta gacaagtatt ctgcgtactc    10560
agcctcccag taaaaggatt ttgaatgaac agttttagaa gacaggaact gcagtgacct    10620
ttccaaattt ggggataatg tgggcaaata aagttacttt tctaaggtca cacaactagg    10680
```

```
aagtaggctc aggttgctgt gcatgtgtgc gtgcattcgt gtgtgtgtgt gtgtgtgtgt      10740
gtgtgtgtgt gtgtgtgtgt gtgtgtgtgt gtgtgtgaga gagagagaga gagagagaga      10800
gagagagaga gagagagaga gagagagaga tctagttgtc aattgaacaa ggtgtatttg      10860
agcctggagg catgagcagg gctggttcct gcggaccctg tgaggactgt gggatgggca      10920
tgggtgttgt ctatactgtg gttgagcacc agtgcccagc gccaggctga ctgactagct      10980
gatacctcct tggtatttgc a                                                11001

<210> SEQ ID NO 7
<211> LENGTH: 2524
<212> TYPE: DNA
<213> ORGANISM: Mus musculus

<400> SEQUENCE: 7 gggcagggg gccggtttgt tgtggtcgcc attttgctgg ttgcattact gggtaatcgg        60
ggccctggct cgccgcgtcc accggacacc ctcagccagt gggcaggtct gagctcgggc      120
tccccgagca gtttgaatcc ccttacccac gccctcaggt ctcagcggcg gtggcagccg      180
aggtgcagga tgcgagaagg cgccccccgg ccgggctccc gctccaggcc tcacgcccct      240
gcggccctct gagcccacca tggccgtccc accaggccat ggtcctttct ctggcttttcc     300 ggggccccag gaacacacac aggtactacc tgatgtgcgg ctcctgcccc ggagactgcc      360
cctggccttc cgggatgcgg cctcagcccc gctgcgcaag ctctcggtgg acctcatcaa      420
gacctacaag cacatcaatg aggtatacta tgcgaagaag aagcggcggg cccaacaggc      480 gccacccag gactcgagca ccaaaaagga gaagaaggtc ctgaaccacg gttatgatga        540
cgacaaccac gactacattg tgcgcagtgg cgagcgctgg ctagagcgct atgagattga      600
ctctcttatt ggcaaaggct cctttggcca ggtggtgaaa gcctatgatc accagactca      660
ggagctggtg gccatcaaga tcatcaagaa caaaaaggcc ttcctgaacc aggcacagat      720
tgagctacgg ctgttggagc tgatgaacca gcatgataca gagatgaagt actacatagt      780
acaccttaag cggcacttca tgttccggaa tcacctgtgc ctggtgtttg agctgctgtc      840
ctacaacctg tacgacctcc tccgcaacac acactttcgg ggtgtctcac tgaacctgac      900
gaggaagctg gcacagcagc tctgcacagc tctgctcttt ctggccaccc ccgagctcag      960
catcatccac tgcgacctca gcctgagaa catcctgctc tgcaaccccca gcgcagtgc     1020 catcaagatc gtggacttcg gcagttcctg ccagcttggc cagcggatct accagtatat     1080
ccagagccgc ttctaccgct cacccgaggt gctcctgggt acacccctatg acctggccat    1140 tgacatgtgg tccctgggct gcatcctcgt ggagatgcac accggagagc cctcttcag      1200 tggctctaat gaggtggacc agatgagccg tattgtggag gtgttgggca tccctcccgc     1260
acccatgctg gaacaggcac ccaaggctcg aaagtacttt gagcggctgc ctggggtgg      1320 ctggacccta cgaaggacaa aggaactcag gaaggattac cagggccctg gacacggcg      1380 gctgcaggag gtgctgggcg tgcagacggg cgggcccggg gccggcggg cggggagcc      1440 cggccacagc cccgccgact acctccgctt ccaggacctg gtgctgcgca tgctggaata    1500
tgagcccgcc gccccgcatca gccctctggg cgctctgcag catggcttct tccgccgcac   1560
ggccgacgag gccaccaaca cgggcccggc aggcagcagt gcctccacct cgccggcgcc   1620
ccttgacacc tgccccctcct ctagcaccgc cagctccatc tccagctctg gaggttccag    1680
tggctcctcc aacgacaaca gagcctaccg atacagcaac cgatattgtg ggggcccagg    1740
```

```
gcccccatc actgactgtg agatgaacag cccccaggtc ctaccctccc agcctctgcg    1800
cccctgggca gggggtgatg tgccccacaa gacacatcaa gccctatct ctgcctcaac    1860
attgccgggg actggggctc agttaccccc attgcccgt tgccttggac gaccccatc     1920
accaacatca ccaccacccc cagagttgat ggatgtgagc ctggtgggca gccctccaga   1980
ctgctctcca cctcctccag cacctgcccc ccagcacccg gctgcctcag ccctccggac   2040
tcggatgaca ggaggtcgac cacctctccc accccctgat gaccctgcca ctctggggcc   2100
tcgcctgggt ctccatggtg tacccagag cacagcagcc agctcatgac cctgccccct    2160
ccctgggcc cctcctgaag ccatacccc ccatatgggg gccctgggct cccatcctca     2220
tctctcccct tgactggact tgctgctacc cagctggggt gggtgaggcc tgcactgact   2280
ggggcccagg gcaggggtc aagggagagg agtttggccg cacctccc actaagactg      2340
gaccttggc ccctctcttc cccctccccc cttgttttct atttattgta ccaaagacag    2400
tggtggtccg gtagagggga gattccccct tacccagggc cctaggaggg ggtggggca    2460
ggtagggga gatggccttg ctcctcctcg ctgtaccccc cagtaaaaag ctttctcaca    2520
tgcc                                                                2524

<210> SEQ ID NO 8
<211> LENGTH: 2477
<212> TYPE: DNA
<213> ORGANISM: Mus musculus

<400> SEQUENCE: 8
tcctcatcgc cgccgccacc accaccgccg ccatgctggc cgctcgccca ccgcactggg    60
gtccccatcg cgctccagcc ccccgtgggc ccagcgccat ccctgacccg ggtctcagcg   120
gcggtggcag ccgaggtgca ggatgcgaga aggcgccccc cggccgggct cccgctccag   180
gcctcacgcc cctgcggccc tctgagccca ccatggccgt cccaccaggc catggtcctt   240
tctctggctt tccggggccc caggaacaca cacaggtact acctgatgtg cggctcctgc   300
cccggagact gcccctggcc ttccgggatg cggcctcagc cccgctgcgc aagctctcgg   360
tggacctcat caagacctac aagcacatca atgaggtata ctatgcgaag aagaagcggc   420
gggcccaaca ggcgccaccc caggactcga gcaccaaaaa ggagaagaag gtcctgaacc   480
acggttatga tgacgacaac cacgactaca ttgtgcgcag tggcgagcgc tggctagagc   540
gctatgagat tgactctctt attggcaaag ctccttttgg ccaggtggtg aaagcctatg   600
atcaccagac tcaggagctg gtggccatca agatcatcaa gaacaaaaag gccttcctga   660
accaggcaca gattgagcta cggctgttgg agctgatgaa ccagcatgat acagagatga   720
agtactacat agtacacctt aagcggcact tcatgttccg gaatcacctg tgcctggtgt   780
ttgagctgct gtcctacaac ctgtacgacc tcctccgcaa cacacacttt cggggtgtct   840
cactgaacct gacgaggaag ctggcacagc agctctgcac agctctgctc tttctggcca   900
cccccgagct cagcatcatc cactgcgacc tcaagcctga aacatcctg ctctgcaacc    960
ccaagcgcag tgccatcaag atcgtggact cggcagttc ctgccagctt ggccagcgga   1020
tctaccagta tatccagagc cgcttctacc gctcacccga ggtgctcctg gtacaccct    1080
atgacctggc cattgacatg tggtccctgg gctgcatcct cgtggagatg cacaccggag   1140
agccctctt cagtggctct aatgaggtgg accagatgag ccgtattgtg gaggtgttgg   1200
gcatccctcc cgcaccatg ctggaacagg caccaaggc tcgaaagtac tttgagcggc    1260
tgcctggggg tggctggacc ctacgaagga caaaggaact caggaaggat taccagggcc   1320
```

```
ctgggacacg gcggctgcag gaggtgctgg gcgtgcagac gggcgggccc ggggccggc    1380 gggcggggga gcccggccac agcccgccg actacctccg cttccaggac ctggtgctgc    1440
gcatgctgga atatgagccc gccgcccgca tcagccctct gggcgctctg cagcatggct    1500
tcttccgccg cacggccgac gaggccacca acacgggccc ggcaggcagc agtgcctcca    1560
cctcgccggc gccccttgac acctgcccct cctctagcac cgccagctcc atctccagct    1620
ctggaggttc cagtggctcc tccaacgaca acagagccta ccgatacagc aaccgatatt    1680
gtgggggccc agggccccccc atcactgact gtgagatgaa cagcccccag gtcctaccct    1740
cccagcctct gcgcccctgg gcaggggtg atgtgcccca aagacacat caagcccta    1800 tctctgcctc aacattgccg gggactgggg ctcagttacc cccattgccc cgttgccttg    1860
gacgaccccc atcaccaaca tcaccaccac ccccagagtt gatggatgtg agcctggtgg    1920
gcagccctcc agactgctct ccacctcctc cagcacctgc ccccagcac ccggctgcct    1980 cagccctccg gactcggatg acaggaggtc gaccacctct cccacccct gatgaccctg    2040 ccactctggg gcctcgcctg ggtctccatg gtgtacccca gagcacagca gccagctcat    2100
gaccctgccc cctccctggg gcccctcctg aagccatacc cccccatatg ggggccctgg    2160
gctcccatcc tcatctctcc ccttgactgg acttgctgct acccagctgg ggtgggtgag    2220
gcctgcactg actgggggcc agggcagggg gtcaagggag aggagtttgg ccgcaccctc    2280
cccactaaga ctggaccctt ggcccctctc ttccccctcc ccccttgttt tctatttatt    2340
gtaccaaaga cagtggtggt ccggtagagg ggagattccc ccttacccag ggccctagga    2400
gggggtgggg gcaggtaggg ggagatggcc ttgctcctcc tcgctgtacc ccccagtaaa    2460
aagctttctc acatgcc                                                   2477

<210> SEQ ID NO 9
<211> LENGTH: 2404
<212> TYPE: DNA
<213> ORGANISM: Mus musculus

<400> SEQUENCE: 9 gggcagggg gccggtttgt tgtggtcgcc attttgctgg ttgcattact gggtaatcgg       60
ggccctggct cgccgcgtcc accggacacc ctcagccagt gggcaggtct gagctcgggc     120
tccccgagca gtttgaatcc ccttaccac gccctcaggt ctcagcggcg gtggcagccg     180
aggtgcagga tgcgagaagg cgcccccgg ccgggctccc gctccaggcc tcacgcccct     240
gcggccctct gagcccacca tggccgtccc accaggccat ggtcctttct ctggcttttcc    300 ggggccccag gaacacacac aggtactacc tgatgtgcgg ctcctgcccc ggagactgcc     360
cctggccttc cgggatgcgg cctcagcccc gctgcgcaag ctctcggtgg acctcatcaa    420
gacctacaag cacatcaatg aggtatacta tgcgaagaag aagcggcggg cccaacaggc     480
gccaccccag gactcgagca ccaaaaagga agaaggtc ctgaaccacg gttatgatga      540
cgacaaccac gactacattg tgcgcagtgg cgagcgctgg ctagagcgct atgagattga     600
ctctcttatt ggcaaaggct cctttggcca ggtggtgaaa gcctatgatc accagactca     660
ggagctggtg gccatcaaga tcatcaagaa caaaaaggcc ttcctgaacc aggcacagat     720
tgagctacgg ctgttggagc tgatgaacca gcatgataca gagatgaagt actacatagt     780
acaccttaag cggcacttca tgttccggaa tcacctgtgc ctggtgtttg agctgctgtc     840
ctacaacctg tacgacctcc tccgcaacac acactttcgg ggtgtctcac tgaacctgac     900
```

```
gaggaagctg gcacagcagc tctgcacagc tctgctcttt ctggccaccc ccgagctcag    960
catcatccac tgcgacctca agcctgagaa catcctgctc tgcaaccccca agcgcagtgc   1020 catcaagatc gtggacttcg gcagttcctg ccagcttggc cagcggatct accagtatat   1080
ccagagccgc ttctaccgct cacccgaggt gctcctgggt acaccctatg acctggccat   1140
tgacatgtgg tccctgggct gcatcctcgt ggagatgcac accggagagc ccctcttcag   1200
tggctctaat gaggtggacc agatgagccg tattgtggag gtgttgggca tccctcccgc   1260
acccatgctg gaacaggcac ccaaggctcg aaagtacttt gagcggctgc tgggggtgg    1320 ctggacccta cgaaggacaa aggaactcag gaaggacctg gtgctgcgca tgctggaata   1380
tgagcccgcc gcccgcatca gccctctggg cgctctgcag catggcttct ccgccgcac    1440 ggccgacgag gccaccaaca cgggcccggc aggcagcagt gcctccacct cgccggcgcc   1500
ccttgacacc tgcccctcct ctagcaccgc cagctccatc tccagctctg gaggttccag   1560
tggctcctcc aacgacaaca gagcctaccg atacagcaac cgatattgtg ggggcccagg   1620
gccccccatc actgactgtg agatgaacag ccccaggtc ctaccctccc agcctctgcg    1680
cccctgggca gggggtgatg tgccccacaa gacacatcaa gcccctatct ctgcctcaac   1740
attgccgggg actggggctc agttacccccc attgccccgt tgccttggac gaccccccatc  1800 accaacatca ccaccacccc cagagttgat ggatgtgagc ctggtgggca gccctccaga   1860
ctgctctcca cctcctccag cacctgcccc ccagcacccg gctgcctcag ccctccggac    1920
tcggatgaca ggaggtcgac cacctctccc accccctgat gaccctgcca ctctggggcc    1980
tcgcctgggt ctccatggtg tacccccagag cacagcagcc agctcatgac cctgcccct    2040 ccctgggggcc cctcctgaag ccatacccccc ccatatgggg gccctgggct cccatcctca   2100 tctctccccct tgactggact tgctgctacc cagctggggt gggtgaggcc tgcactgact   2160
ggggcccagg gcaggggggtc aagggagagg agtttggccg caccctcccc actaagactg   2220 gaccccttggc ccctctcttc ccccctcccccc cttgttttct atttattgta ccaaagacag    2280
tggtggtccg gtagagggga gattcccccct tacccagggc cctaggaggg ggtgggggca    2340
ggtaggggga gatggccttg ctcctcctcg ctgtacccccc cagtaaaaag ctttctcaca    2400
tgcc                                                                 2404
```

```
<210> SEQ ID NO 10
<211> LENGTH: 23
<212> TYPE: DNA
<213> ORGANISM: Artificial sequence
<220> FEATURE:
<223> OTHER INFORMATION: Primer

<400> SEQUENCE: 10
gatgaaccag catgatacag aga                                             23

<210> SEQ ID NO 11
<211> LENGTH: 20
<212> TYPE: DNA
<213> ORGANISM: Artificial sequence
<220> FEATURE:
<223> OTHER INFORMATION: Primer

<400> SEQUENCE: 11
cgtacaggtt gtaggacagc                                                 20

<210> SEQ ID NO 12
<211> LENGTH: 25
```

```
<212> TYPE: DNA
<213> ORGANISM: Artificial sequence
<220> FEATURE:
<223> OTHER INFORMATION: Probe

<400> SEQUENCE: 12
caccttaagc ggcacttcat gttcc                                        25

<210> SEQ ID NO 13
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 13
atcggtaggc tctgttgtcg                                              20

<210> SEQ ID NO 14
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 14
cctctccctt gaccccctgc                                              20

<210> SEQ ID NO 15
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 15
aatctcccct ctaccggacc                                              20

<210> SEQ ID NO 16
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 16
ggtggcggcg gcgatgagga                                              20

<210> SEQ ID NO 17
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 17
ccctcgggct cagcctcttc                                              20

<210> SEQ ID NO 18
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 18
```
ggcggcggcg atgaggaggt          20

<210> SEQ ID NO 19
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 19
cttgtcagat cccttctat          20

<210> SEQ ID NO 20
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 20
ctacgctggg tcattccaca          20

<210> SEQ ID NO 21
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 21
ctatagatgt ttcaaccacc          20

<210> SEQ ID NO 22
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 22
aggcagaaac cgtgtagagt          20

<210> SEQ ID NO 23
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 23
cccttcaatc ctcaggcagg          20

<210> SEQ ID NO 24
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 24
ccaaactcct ctcccttgac          20

<210> SEQ ID NO 25
<211> LENGTH: 20
<212> TYPE: DNA
<213> ORGANISM: Artificial sequence

```
<220> FEATURE:
<223> OTHER INFORMATION: Synthetic oligonucleotide

<400> SEQUENCE: 25
cacagataaa caacctcttc                                               20

<210> SEQ ID NO 26
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 26
tttcttcttt accctgaggt                                               20

<210> SEQ ID NO 27
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 27
atggacctcc cagcaaaccc                                               20

<210> SEQ ID NO 28
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 28
ggagccatca gagccagaca                                               20

<210> SEQ ID NO 29
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 29
tcacatccct tatactggat                                               20

<210> SEQ ID NO 30
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 30
cgtccctcac cagctgcggg                                               20

<210> SEQ ID NO 31
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 31
aagcaaaacc tccaaaagta                                               20
```

<210> SEQ ID NO 32
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 32
gtcaaaacag ctccacattt                                               20

<210> SEQ ID NO 33
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 33
tgttgtgaac cttcagacct                                               20

<210> SEQ ID NO 34
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 34
ttccattctg ccccaggtca                                               20

<210> SEQ ID NO 35
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 35
tcagcttcat cctttctctt                                               20

<210> SEQ ID NO 36
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 36
tgtcctctac agagtccctt                                               20

<210> SEQ ID NO 37
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 37
ccaccctctt ccaaaatttc                                               20

<210> SEQ ID NO 38
<211> LENGTH: 20
<212> TYPE: DNA
<213> ORGANISM: Artificial sequence
<220> FEATURE:
<223> OTHER INFORMATION: Synthetic oligonucleotide

```
<400> SEQUENCE: 38
ccttccctga aggttcctcc                                               20

<210> SEQ ID NO 39
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 39
ctaaaagtgt ccttcg                                                   16

<210> SEQ ID NO 40
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 40
gcacaagact tcactc                                                   16

<210> SEQ ID NO 41
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 41
tccctaaata tcgcac                                                   16

<210> SEQ ID NO 42
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 42
tctaagagtc acggtc                                                   16

<210> SEQ ID NO 43
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 43
catctaagag tcacgg                                                   16

<210> SEQ ID NO 44
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 44
acatctaaga gtcacg                                                   16

<210> SEQ ID NO 45
```

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 45
atagatgttt caacca                                                        16

<210> SEQ ID NO 46
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 46
agttacaaag ctcctg                                                        16

<210> SEQ ID NO 47
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 47
ggccaatacg ccgtca                                                        16
```